(12) United States Patent
Ding et al.

(10) Patent No.: US 8,173,805 B2
(45) Date of Patent: *May 8, 2012

(54) SEH INHIBITORS AND THEIR USE

(75) Inventors: Yun Ding, Waltham, MA (US); Reema K. Thalji, Collegeville, PA (US); Joseph P. Marino, Jr., King of Prussia, PA (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/682,073

(22) PCT Filed: Oct. 10, 2008

(86) PCT No.: PCT/US2008/079517
§ 371 (c)(1),
(2), (4) Date: Apr. 8, 2010

(87) PCT Pub. No.: WO2009/049157
PCT Pub. Date: Apr. 16, 2009

(65) Prior Publication Data
US 2010/0210656 A1  Aug. 19, 2010

Related U.S. Application Data

(60) Provisional application No. 60/979,154, filed on Oct. 11, 2007.

(51) Int. Cl.
C07D 251/54 (2006.01)
C07D 403/12 (2006.01)
C07D 403/14 (2006.01)
A61K 31/53 (2006.01)
A61P 9/08 (2006.01)
A61P 9/10 (2006.01)
A61P 9/12 (2006.01)
A61P 11/06 (2006.01)
A61P 11/00 (2006.01)
A61P 13/12 (2006.01)

(52) U.S. Cl. ........ 544/197; 544/198; 544/208; 544/209; 514/245

(58) Field of Classification Search .................. 544/197, 544/198, 208, 209; 514/245
See application file for complete search history.

(56) References Cited

U.S. PATENT DOCUMENTS

| | | | |
|---|---|---|---|
| 5,420,283 | A | 5/1995 | Dugger |
| 6,831,082 | B2 | 12/2004 | Ingraham et al. |
| 6,890,925 | B2 | 5/2005 | Ingraham et al. |
| 2002/0028832 | A1 | 3/2002 | Ashwell |
| 2002/0061899 | A1 | 5/2002 | Diamond et al. |
| 2002/0091133 | A1 | 7/2002 | Taylor |
| 2002/0115854 | A1 | 8/2002 | Lam et al. |
| 2004/0029902 | A1 | 2/2004 | Singh et al. |
| 2004/0167141 | A1 | 8/2004 | Bebbington et al. |
| 2005/0049247 | A1 | 3/2005 | Wilson et al. |
| 2005/0197350 | A1 | 9/2005 | Sckiguchi et al. |
| 2006/0069110 | A1 | 3/2006 | Andersen et al. |
| 2006/0194803 | A1 | 8/2006 | Kubota et al. |
| 2006/0276515 | A1 | 12/2006 | Cywin et al. |
| 2007/0105901 | A1 | 5/2007 | Ohtake et al. |
| 2007/0225283 | A1 | 9/2007 | Hammock et al. |
| 2010/0210628 | A1 | 8/2010 | Ding et al. |
| 2010/0210655 | A1 | 8/2010 | Ding et al. |
| 2010/0249137 | A1 | 9/2010 | Ding et al. |
| 2010/0261743 | A1 | 10/2010 | Londregan et al. |
| 2010/0311775 | A1 | 12/2010 | Marino et al. |
| 2010/0311776 | A1 | 12/2010 | Marino et al. |
| 2010/0324076 | A1 | 12/2010 | Marino et al. |

FOREIGN PATENT DOCUMENTS

EP  1464335  10/2004
(Continued)

OTHER PUBLICATIONS

Dorrance, Phd., et al.: "An Epoxide Hydrolase Inhibitor, 12-(3-Adamantan-1-Y1-Ureido)Dodecanoic Acid (AUDA), Reduces Ischemic Cerebral Infact Size in Stroke-Prone Spontaneously Hypertensive Rats" Journal of Cardiovascular Pharmacology, Dec. 2005, vol. 46, No. 6, pp. 842-848. Fornage, et al.: "The Soluble Epoxide Hydrolase Gene Harbors Sequence Variation Associated With Susceptibility to and Protection From Incident Ischemic Stroke" Human Molecular Genetics, 2005, vol. 14, No. 19, pp. 2829-2837.

Fretland, et al.: "Epoxide Hydrolases: Biochemistry and Molecular Biology", Chemico-Biological Interactions. 2000; vol. 129, pp. 41-59.

Imig, et al.: "Soluble Epoxide Hydrolase Inhibition Lowers Arterial Blood Pressure in Angiotensin II Hypertension" Hypertension. 2002; vol. 39 (Part 2), pp. 690-694.

(Continued)

Primary Examiner — Venkataraman Balasubramanian
(74) Attorney, Agent, or Firm — Linda E. Hall; John L. Lemanowicz

(57) ABSTRACT

The invention is directed to novel sEH inhibitors and their use in the treatment of diseases mediated by the sEH enzyme. Specifically, the invention is directed to compounds according to Formula I:

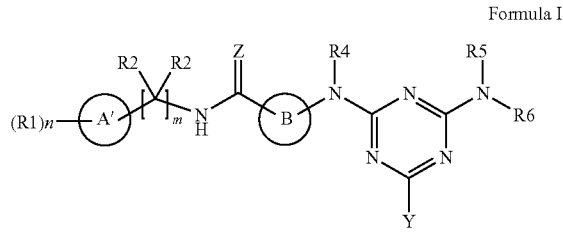

Formula I wherein R1, R2, R4, R5, R6, A, B, Y, Z, n, and m are defined below, and to pharmaceutically-acceptable salts thereof. The compounds of the invention are sEH inhibitors and can be used in the treatment of diseases mediated by the sEH enzyme, such as hypertension. Accordingly, the invention is further directed to pharmaceutical compositions comprising a compound of the invention. The invention is still further directed to methods of inhibiting sEH and treatment of conditions associated therewith using a compound of the invention or a pharmaceutical composition comprising a compound of the invention.

16 Claims, No Drawings

FOREIGN PATENT DOCUMENTS

| WO | WO 02/32872 | 4/2002 |
|---|---|---|
| WO | WO 02/50066 | 6/2002 |
| WO | WO 03/007963 | 1/2003 |
| WO | WO 03/097050 | 11/2003 |
| WO | WO 2005/028467 | 3/2005 |
| WO | WO 2005/070903 | 8/2005 |
| WO | WO 2006/053109 | 5/2006 |
| WO | WO 2006/065820 | 6/2006 |
| WO | WO 2007/106525 A1 | 9/2007 |
| WO | WO 2008/105968 | 9/2008 |
| WO | WO2008/105968 | 9/2008 |
| WO | WO 2009/048154 | 4/2009 |
| WO | WO2009/049154 | 4/2009 |
| WO | WO 2009/049157 A1 | 4/2009 |
| WO | WO 2009/049165 A1 | 4/2009 |
| WO | WO2009049165 A1 | 4/2009 |
| WO | WO2009/070497 | 6/2009 |
| WO | WO2009/073772 | 6/2009 |
| WO | WO2009/097474 | 8/2009 |
| WO | WO2009/097475 | 8/2009 |
| WO | WO2009/097476 | 8/2009 |
| WO | WO2010/011917 | 1/2010 |

OTHER PUBLICATIONS

Imig, et al.: "An Orally Active Epoxide Hydrolase Inhibitor Lowers Blood Pressure and Provides Renal Protection in Salt-Sensitive Hypertension" Hypertension. 2005; vol. 46 (Part 2): pp. 975-981.

Imig, et al.: "Cardiovascular Therapeutic Aspects of Soluble Epoxide Hydrolase Inhibitors" Cardiovascular Drug Reviews. 2006; vol. 24, No. 2, pp. 169-188.

Inceoglu, et al.: "Inhibition of Soluble Epoxide Hydrolase Reduces LPS-Induced Thermal Hyperalgesia and Mechanical Allodynia in a Rat Model of Inflammatory Pain" Life Sciences. 2006; vol. 79, pp. 2311-2319.

Jones, P.D. et al.: "Synthesis and SAR of Conformationally Restricted Inhibitors of Soluble Epoxide Hydrolase" Bioorganic & Medicinal Chemistry Letters, Oct. 1, 2009, vol. 16, No. 19, pp. 5212-5216.

Jung, et al.: "Soluble Epoxide Hydrolase Is a Main Effector of Angiotensin II-Induced Hypertension" Hypertension. 2005; vol. 45 (Part 2), pp. 759-765.

Koerner, et al.: "Polymorphisms in the Human Soluble Epoxide Hydrolase Gene *EPHX2* Linked to Neuronal Survival After Ischemic Injury" The Journal of Neuroscience. Apr. 25, 2007; vol. 27, No. 17, pp. 4642-4649.

Krotz, et al.: "Membrane Potential—Dependent Inhibition of Platelet Adhesion to Endothelial Cells by Epoxyeicosatrienoic Acids" Arterioscler Thrombosis Vascular Biology. 2004; vol. 24, pp. 595-600.

Lee, et al.: "Genetic Variation in Soluble Epoxide Hydrolase (*EPHX2*) and Risk of Coronary Heart Disease: The Atherosclerosis Risk in Communities (ARIC) Study" Human Molecular Genetics. 2006; vol. 15, No. 10, pp. 1640-1649.

Loch, et al.: "Prevention of Hypertension in DOCA-Salt Rats by an Inhibitor of Soluble Epoxide Hydrolase" Cell Biochemistry and Biophysics. 2007; vol. 47, pp. 87-97.

Sato, et al.: "Soluble Epoxide Hydrolase Variant (Glu287Arg) Modifies Plasma Total Cholesterol and Triglyceride Phenotype in Familial Hypercholesterolemia: Intrafamilial Association Study in an Eight-Generation Hyerlipidemic Kindred" Journal of Human Genetics. 2004; vol. 49, pp. 29-34.

Sinal, et al.: "Targeted Disruption of Soluble Epoxide Hydrolase Reveals a Role in Blood Pressure Regulation" The Journal of Biological Chemistry. 2000; vol. 275, No. 51, pp. 40504-40510.

Spector, et al.: "Epoxyeicosatrienoic Acids (Eets): Metabolism and Biochemical Function" Progress in Lipid Research. 2004; vol. 43, pp. 55-90.

Wei, et al.: "Sequence Variation in the Soluble Epoxide Hydrolase Gene and Subclinical Coronary Atherosclerosis: Interaction With Cigarette Smoking" Atherosclerosis. 2007; vol. 190, pp. 26-34.

Xu, et al.: "Prevention and Reversal of Cardiac Hypertrophy by Soluble Epoxide Hydrolase Inhibitors" Proceedings National Academy of Sciences. 2006; vol. 103, No. 49, pp. 18733-18738.

Zhao, et al.: "Soluble Epoxide Hydrolase Inhibition Protects the Kidney from Hypertension-Induced Damage" Journal of the American Society of Nephrology, 2004, vol. 15, pp. 1244-1253.

Andrews, et al., J. Clin Endo Metab 88, 285-291, 2003.

Belanoff, et al., J. Psych Res, 35, 127-145, 2001.

Berthiaume, et al., Am J Physiol Endocrinol Metab, 293, E1045-E1052, 2007.

Chrousos, Proc Nat Acad Sci, 101, 6329-6330, 2004.

Dallman, et al, Endocrino 145, 2633-2638, 2004.

Dorrance, et al. Journal of Cardiovascular Pharmacology, 46(6): 842-848 (2005).

Draper, et al., J. Endocrin 186, 251-271, 2005.

Fornage, et al. Human Molecular Genetics, 14(19): 2829-2837 (2005).

Fretland, et al. Chemico-Biological Interactions, 129: 41-59 (2000).

Gambineri et al., J. Clin Endo Metab, 91, 2295-2302, 2006.

Gomez, et al. Human soluble epoxide hydrolase: Structural basis of inhibitition by 4-(3-cyclohexylureido)-carboxylic acids. Protein Science, 2006, 15:58-64, esp. p. 60, Fig 3.

Hadoke et al., Cell Mol Life Sci, 63, 565-578, 2006.

Hatakeyama et al., Hypertens 33, 1179-1184, 1999.

Hermanowski-Vosatka et al., J Exp Med, 202, 517-527, 2005.

Imig, et al. Cardiovascular Drug Reviews, 24(2): 169-188 (2006).

Imig, et al. Hypertension, 39 (Part 2): 690-694 (2002).

Imig, et al. Hypertension, 46 (Part 2): 975-981 (2005).

Inceoglu, et al. Life Sciences, 79: 2311-2319 (2006).

Jones, et al. Bioorganic & Medicinal Chemistry Letters, 16(19): 5212-5216 (2009).

Jung, et al. Hypertension, 45 (Part 2): 759-765 (2005).

Koerner, et al. The Journal of Neuroscience, 27(17): 4642-4649 (2007).

Krotz, et al. Arterioscler. Thrombosis Vascular Biology, 24: 595-600 (2004).

Krozowski et al. Endo J, 50, 485-498, 2003.

Lee, et al. Human Molecular Genetics, 15(10): 1640-1649 (2006).

Loch, et al. Cell Biochemistry and Biophysics, 47: 87-97 (2007).

Paterson et al., Proc Natl Acad U.S.A., 101, 7088-7093, 2004.

Perez de Prada et al., Athero, 191, 33-339,2007.

Sandeep et al., Proc Natl Acad Sci, 101, 6734-6739, 2004.

Sato, et al. Journal of Human Genetics, 49: 29-34 (2004).

Sinal, et al. The Journal of Biological Chemistry, 275(51): 40504-40510 (2000).

Spector, et al. Progress in Lipid Research, 43: 55-90 (2004).

Stulnig et al., Diabetol 47,1-11, 2004.

Tomlinson et al Nat Clin Prac Endo Metab, 1, 92-99, 2005.

Walker, EurJ Endocrinol, 157, 545-59, 2007.

Wang, Nutrit Metabol 2, 1-14, 2005.

Wei, et al. Atherosclerosis, 190: 26-34 (2007).

White et al., Endocr Rev 18, 135-156, 1997.

Xu, et al. Proceedings National Academy of Sciences, 103(49): 18733-18738 (2006).

Young et al., Clin Sci 112, 467-475, 2007.

Zhao, et al. Journal of the American Society of Nephrology, 15: 1244-1253 (2004).

SEH INHIBITORS AND THEIR USE

This application is a 371 of International Application No. PCT/US2008/079517, filed 10 Oct. 2008, which claims the benefit of U.S. Provisional Application No. 60/979,154, filed 11 Oct. 2007, which are incorporated herein in their entirety.

FIELD OF THE INVENTION

The invention is directed to novel sEH inhibitors and their use in the treatment of diseases mediated by the sEH enzyme.

BACKGROUND OF THE INVENTION

Epoxide functional groups may be found in drugs, xenobiotic materials, and endogenous biomolecules. Epoxide hydrolases, found in both plants and animals, are enzymes that convert epoxides to diols by hydrolysis. In mammals, soluble epoxide hydrolase ("sEH") is primarily responsible for the metabolism of arachidonic acid derivatives known as epoxyeicosatrienoic acids ("EETs"). sEH converts EETs into dihydroxyeicosatrienoic acids ("DHETs"). Several publications have described the beneficial vasodilatory, anti-inflamatory, and anti-thrombotic effects of EETs. See E.g. Spector et al., *Prog. Lipid Res.*, 43, 55-90, 2004; Imig, *Cardiovasc. Drug Rev.*, 24, 169-188, 2006. DHETs are generally inactive and thus do not exhibit the beneficial effects of EETs.

Conversely, microsomal epoxide hydrolase ("mEH") catalyzes the hydrolysis of a broad range of epoxide substrates including carcinogenic polycyclic aromatic hydrocarbons and reactive epoxides, thus it provides an important detoxification pathway. Polymorphisms in mEH may lead to differences in bioactivation of pro-carcinogens and several human epidemiological studies suggest that mEH genotype is associated with altered cancer risk. Fretland & Omiecinski, *Chemico-Biol. Int*, 129, 41-59, 2000.

Pharmacological, knockout mouse phenotype and genetic polymorphism studies suggest that elevated EET levels are protective in numerous cardiovascular disorders including hypertension [Sinal et al., *J. Biol. Chem.*, 275, 40504-40510, 2000; Imig et al., *Hypertension*, 39, 690-694, 2002; Jung et al., *Hypertension*, 45, 759-765, 2005; Loch et al., *Cell Biochem Biophys.*, 47, 87-98, 2007], heart failure [Xu et al., *Proc. Natl. Acad. Sci. U.S.A.* 103, 18733-18738, 2006], renal dysfunction I end organ damage [Zhao et al., *J. Am. Soc. Nephrol.*, 15; 1244-1253, 2004; Imig et al., *Hypertension*, 46; 975-981, 2005], stroke [Dorrance et al., *J. Cardiovasc. Pharmacol.*, 46; 842-848, 2005; Formage et al., *Hum. Mol. Genet.*, 14; 2829-2837, 2005; Koerner et al., *J. Neurosci.*, 27; 4642-4649, 2007], atherosclerosis and thrombosis [Sato et al., *J. Hum. Genet.*, 49; 29-34, 2004; Lee et al., *Hum Mol. Genet.*, 15; 1640-1649, 2006; Wei et al., *Atherosclerosis*, 190; 26-34, 2007; Krotz et al., *Arterioscler. Thromb. Vasc. Biol.*, 24; 595-600, 2004] and inflammation [Inceoglu et al., *Life Sci.*, 79; 2311-2319, 2006].

One approach to the treatment of such conditions designed to take advantage of the beneficial effect of EETs has been to inhibit the action of sEH thereby preventing EET degradation. In light of the role sEH plays in the degradation of EETs, it is desirable to prepare compounds that inhibit its activity. Thus, there is a need to identify compounds that inhibit sEH, which can be used in the treatment of a variety of conditions mediated by the sEH enzyme.

SUMMARY OF THE INVENTION

The invention is directed to novel sEH inhibitors and their use in the treatment of diseases mediated by the sEH enzyme.

Specifically, the invention is directed to compounds according to Formula I:

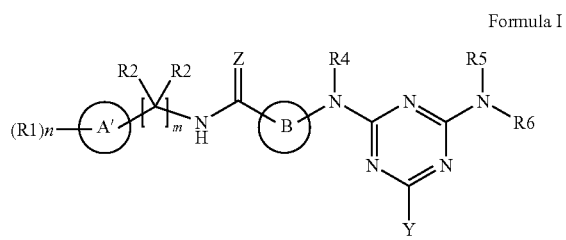

Formula I wherein R1, R2, R4, R5, R6, A, B, Y, n, and m are defined below, and to pharmaceutically-acceptable salts thereof.

The compounds of the invention are sEH inhibitors and can be used in the treatment of diseases mediated by the sEH enzyme, such as hypertension. Accordingly, the invention is further directed to pharmaceutical compositions comprising a compound of the invention. The invention is still further directed to methods of inhibiting sEH and treatment of conditions associated therewith using a compound of the invention or a pharmaceutical composition comprising a compound of the invention.

DETAILED DESCRIPTION OF THE INVENTION

In describing the invention, chemical elements are identified in accordance with the Periodic Table of the Elements. Abbreviations and symbols utilized herein are in accordance with the common usage of such abbreviations and symbols by those skilled in the chemical and biological arts. For example, the following abbreviations are used herein:

"aq" is an abbreviation for aqueous

"BOP" is an abbreviation for (Benzotriazol-1-yloxy)tris (dimethylamino)phosphonium hexafluorophosphate "° C." is an abbreviation for degrees Celsius "DIEA" is an abbreviation for di-isopropylethylamine "DMAP" is an abbreviation for dimethylaminopyridine "DMF" is an abbreviation for dimethylformamide "DMSO" is an abbreviation for Dimethylsulfoxide "EDCl" is an abbreviation for N-(3-Dimethylaminopropyl)-N'-ethylcarbodiimide hydrochloride "equiv" is an abbreviation for equivalent "HPLC" is an abbreviation for High Pressure Liquid Chromatography "g" is an abbreviation for gram or grams "L" is an abbreviation for liter or liters "LC-MS" is an abbreviation for Liquid chromatography-Mass spectrometry "mL" is an abbreviation for milliliter or milliliters "min" is an abbreviation for minute or minutes "mmol" is an abbreviation for millimole or millimolar "N" is an abbreviation for Normal and refers to the number of equivalents of reagent per liter of solution "Ph" is an abbreviation for phenyl "sat" is an abbreviation for saturated "TFA" is an abbreviation for trifluoroacetic acid "THF" is an abbreviation for tetrahydrofuran

TERMS AND DEFINITIONS

"Alkyl" refers to a monovalent saturated hydrocarbon chain having the specified number of member atoms. For example, C1-C8 alkyl refers to an alkyl group having from 1 to 8 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a monovalent saturated or unsaturated hydrocarbon ring having the specified number of member atoms. For example, C3-C6 cycloalkyl refers to a cycloalkyl group having from 3 to 6 member atoms. Unsaturated Cycloalkyl groups have one or more carbon-carbon double bonds within the ring. Cycloalkyl groups are not aromatic. Cycloalkyl groups having from 3 to 7 member atoms or less are monocyclic ring systems. Cycloalkyl groups having at least 7 member atoms may be monocyclic, bridged or fused bicyclic ring systems. Cycloalkyl groups may be optionally substituted with one or more substituents as defined herein. Cycloalkyl includes cyclopropyl, cyclopropenyl, cyclobutyl, cyclobutenyl, cyclopentyl, cyclopentenyl, cyclohexyl, cyclohexenyl, cycloheptanyl, and cycloheptenyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group that is substituted with one or more halo substituents. Haloalkyl includes trifluoromethyl.

"Heteroaryl" refers to a monovalent aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Unless otherwise specified, heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Unless otherwise specified, heterocycloalkyl groups are monocyclic, bridged, or fused ring systems. Monocyclic heterocycloalkyl rings have from 4 to 7 member atoms. Bridged or bicyclic heterocycloalkyl rings have from 7 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl, azabicylo[3.2.1]octyl, azabicylo[3.3.1]nonyl, azabicylo[4.3.0]nonyl, oxabicylo[2.2.1]heptyl, and pthalimidyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Compounds

The invention is directed to compounds according to Formula I:

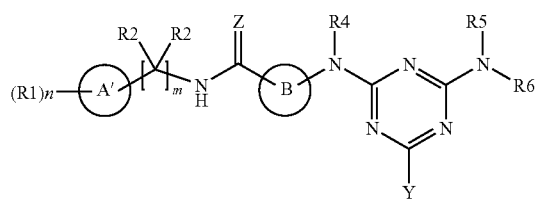

Formula I wherein:
A is phenyl, or monocyclic heteroaryl;
R1 is independently selected from the group consisting of: halo, CN, Ra, ORb, C(O)ORc, C(O)NRcRc, NRcRc, NRcC(O)Rb, NRcS(O₂)Ra, SRb, S(O₂)Ra, and S(O₂)NRcRc;
n is an integer from 0 to 5;
R2 is H or C1-C3 alkyl;
m is 1 or 2;
Z is O or S;
B is C3-C10 cycloalkyl;
R4 is H, or C1-C6 alkyl;
Y is R7, R8, R9, R10, R11, or R12;
R5 is H, R51, R52, R53, R54, R55, —C(O)Rb, —C(O)NRcRc, —S(O₂)Ra, or —S(O₂)NRcRc;
each R51 is C1-C6 alkyl optionally substituted with one or more substituents selected from the group consisting of: halo, ORd, SRk, C(O)ORc, C(O)NReRe, NReRe, Rg, Rh, Ri, Rj;
each R52 is C3-C6 cycloalkyl optionally substituted with one or more substituents selected from the group consisting of: halo, ORd, SRd, C(O)ORc, C(O)NReRe, NReRe, C1-C3 alkyl, and C1-C3 haloalkyl;
R53 is monocyclic heterocycloalkyl optionally substituted with one or more C1-C3 alkyl;
R54 is phenyl optionally substituted with one or more substituents selected from the group consisting of: halo, CN, Ra, ORb, C(O)ORc, C(O)NRcRc, NRcRc, NRcC(O)Rb, NRcS(O₂)Ra, SRb, S(O₂)Ra, and S(O₂)NReRe;
R55 is monocyclic heteroaryl optionally substituted with one or more substituents selected from the group consisting of: halo, —CN, C1-C3 alkyl, C1-C3 haloalkyl, ORd, and NReRe;
R6 is H, R51, or R52; or
R5 and R6 taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;
R7 is C1-C8 alkyl optionally substituted with one or more substituents selected from the group consisting of: halo, ORd, SRd, NReRe, C3-C6 cycloalkyl, R1, and Rj;
R8 is C3-C6 cycloalkyl optionally substituted with one or more substituents selected from the group consisting of: halo, ORd, SRd, NReRe, C1-C3 alkyl, and C1-C3 haloalkyl;
R9 monocyclic heterocycloalkyl optionally substituted with one or more C1-C3 alkyl;
R10 is phenyl optionally substituted with one or more substituents selected from the group consisting of: halo, CN, Ra, ORb, C(O)ORc, C(O)NReRe, NReRe, NRcC(O)Rb, NRcS(O₂)Ra, SRb, S(O₂)Ra, and S(O₂)NRcRc
R11 is heteroaryl optionally substituted with one or more substituents selected from the group consisting of: halo, CN, Ra, ORb, C(O)ORc, C(O)NReRe, NReRe, NRcC(O)Rb, NRcS(O₂)Ra, SRb, S(O₂)Ra, and S(O₂)NRcRc;
R12 is —OR8, —OR9, —OR10, —OR11, —SR7, —SR8, —SR9, —SR10, or SR11;
each Ra is independently C1-C6 alkyl or C1-C6 haloalkyl;
each Rb is independently H, C1-C6 alkyl or C1-C6 haloalkyl;
each Rc is independently H or C1-C6 alkyl;
where there are two Rc groups attached to a nitrogen;
both Rc groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;
each Rd is independently H, C1-C3 alkyl or C1-C3 haloalkyl;
each Re is independently H, C1-C3 alkyl, CH₂—CF₃; or
both Re groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;
each Rf is independently H or C1-C3 alkyl.
each Rg is C3-C6 cycloalkyl optionally substituted with one or more substituents selected from the group consisting of: halo, ORd, SRd, C(O)ORc, C(O)NReRe, NReRe, and C1-C3 alkyl;
each Rh is monocyclic heterocycloalkyl optionally substituted with one or more C1-C3 alkyl;
each Ri is phenyl optionally substituted with one or more substituents selected from the group consisting of: halo, —CN, C1-C3 alkyl, C1-C3 haloalkyl, ORd, and NReRe;
each Rj is monocyclic heteroaryl optionally substituted with one or more substituents selected from the group consisting of: halo, —CN, C1-C3 alkyl, C1-C3 haloalkyl, ORd, and NReRe; and
each Rk is independently H, C1-C3 alkyl, C1-C3 haloalkyl, or benzyl optionally substituted with one or more substituents selected from the group consisting of: halo, —CN, C1-C3 alkyl, C1-C3 haloalkyl, ORd, and NReRe;
or a pharmaceutically acceptable salt thereof.

The meaning of any functional group or substituent thereon at any one occurrence in Formula I, or any subformula thereof, is independent of its meaning, or any other functional group's or substituent's meaning, at any other occurrence, unless stated otherwise.

The compounds according to Formula I may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass any stereoisomer and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzamatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may contain an acidic functional group and are therefore capable of forming pharmaceutically-acceptable base addition salts by treatment with a suitable base. In certain other embodiments, compounds according to Formula I may contain a basic functional group and are therefore capable of forming pharmaceutically-acceptable acid addition salts by treatment with a suitable acid. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts impart greater stability or solubility to the molecule thereby facilitating formulation into a dosage form. Accordingly, the invention is further directed to pharmaceutically-acceptable salts of the compounds according to Formula.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

Because of their potential use in medicine, the salts of the compounds of formula (I) are preferably pharmaceutically acceptable. Suitable pharmaceutically acceptable salts can include acid or base addition salts.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base addition salt can be formed by reaction of a compound of formula (I) with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in the compound of formula (I).

Other non-pharmaceutically acceptable salts, eg. oxalates, may be used, for example in the isolation of compounds of the invention, and are included within the scope of this invention.

The invention includes within its scope all possible stoichiometric and non-stoichiometric forms of the salts of the compounds of formula (I).

As used herein, the term "compounds of the invention" means both the compounds according to Formula I and the pharmaceutically-acceptable salts thereof. The term "a compound of the invention" also appears herein and refers to both a compound according to Formula I and its pharmaceutically-acceptable salts.

In the solid state, compounds of the invention can exist in crystalline, semi-crystalline and amorphous forms, as well as mixtures thereof. The skilled artisan will appreciate that pharmaceutically-acceptable solvates of a compound of the invention may be formed wherein solvent molecules are incorporated into the solid-state structure during crystallization. Solvates may involve water or nonaqueous solvents, or mixtures thereof. In addition, the solvent content of such solvates can vary in response to environment and upon storage. For example, water may displace another solvent over time depending on relative humidity and temperature.

Solvates wherein water is the solvent that is incorporated into the solid-state structure are typically referred to as "hydrates." Solvates wherein more than one solvent is incorporated into the solid-state structure are typically referred to as "mixed solvates". Solvates include "stoichiometric solvates" as well as compositions containing variable amounts of solvent (referred to as "non-stoichiometric solvates"). Stoichiometric solvates wherein water is the solvent that is incorporated into the solid-state structure are typically referred to as "stoichiometric hydrates", and non-stoichiometric solvates wherein water is the solvent that is incorporated into the solid-state structure are typically referred to as "non-stoichiometric hydrates". The invention includes both stoichiometric and non-stoichiometric solvates.

In addition, crystalline forms of a compound of the invention, including solvates thereof, may contain solvent molecules, which are not incorporated into the solid-state structure. For example, solvent molecules may become trapped in the crystals upon isolation. In addition, solvent molecules may be retained on the surface of the crystals. The invention includes such forms.

The skilled artisan will further appreciate that compounds of the invention, including solvates thereof, may exhibit polymorphism (i.e. the capacity to occur in different crystalline packing arrangements). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different IR spectra and X-ray powder diffraction patterns, which may be used for identification. Polymorphs may also exhibit different melting points, which may be used for identification. The skilled artisan will appreciate that different polymorphs may be produced, for example, by changing or adjusting the reaction conditions or reagents, used in making the compound. For example, changes in temperature, pressure, or solvent may result in the production of different

Representative Embodiments

In one embodiment:
A is phenyl, thiophenyl, or pyridyl;
R1 is $CF_3$, halo, $OCF_3$, CN, $OC_1$-$C_6$ alkyl, morpholino, $CO_2H$, or $N(CH_3)_2$;
n is 1, 2, or 3;
B is cyclohexyl;
R4 is hydrogen;
Z is O;
Y is C1-C3 alkyl, phenyl, thiophenyl, or pyridyl; wherein the phenyl, thiophenyl or pyridyl may be substituted by —$CO_2H$, $SO_2Me$, $CF_3$, halo, or CN;
R5 is hydrogen or C1-C6 alkyl; and
R6 is hydrogen or C1-C6 alkyl.

In another embodiment:
A is phenyl;
R1 is $CF_3$, halo, $OCF_3$, CN, $OC_1$-$C_6$ alkyl, or morpholino;
n is 1, or 2;
B is cyclohexyl;
R4 is hydrogen;
Z is O;
Y is methyl;
R5 is hydrogen; and
R6 is methyl.

Specific examples of compounds of the present invention include the following:

cis-4-{[4-(methylamino)-6-(3-pyridinyl)-1,3,5-triazin-2-yl]amino}-N-{[2-(trifluoromethyl)phenyl]methyl}cyclohexanecarboxamide;

cis-4-{[4-(methylamino)-6-phenyl-1,3,5-triazin-2-yl]amino}-N-{[2-(trifluoromethyl)phenyl]methyl}cyclohexanecarboxamide;

cis-4-{[4-(methylamino)-6-(3-thienyl)-1,3,5-triazin-2-yl]amino}-N-{[2-(trifluoromethyl)phenyl]methyl}cyclohexanecarboxamide;

cis-4-{[4-[4-(1,1-dimethylethyl)phenyl]-6-(methylamino)-1,3,5-triazin-2-yl]amino}-N-{[2-(trifluoromethyl)phenyl]methyl}cyclohexanecarboxamide;

cis-4-{[4-(2-fluorophenyl)-6-(methylamino)-1,3,5-triazin-2-yl]amino}-N-{[2-(trifluoromethyl)phenyl]methyl}cyclohexanecarboxamide;

cis-4-{[4-(4-cyanophenyl)-6-(methylamino)-1,3,5-triazin-2-yl]amino}-N-{[2-(trifluoromethyl)phenyl]methyl}cyclohexanecarboxamide;

cis-4-({4-(methylamino)-6-[4-(methylsulfonyl)phenyl]-1,3,5-triazin-2-yl}amino)-N-({2-[(trifluoromethyl)oxy]phenyl}methyl)cyclohexan;

cis-4-{[4-(methylamino)-6-(3-pyridinyl)-1,3,5-triazin-2-yl]amino}-N-({2-[(trifluoromethyl)oxy]phenyl}methyl)cyclohexanecarboxamide;

cis-4-({4-(methylamino)-6-[4-(trifluoromethyl)phenyl]-1,3,5-triazin-2-yl}amino)-N-({2-[(trifluoromethyl)oxy]phenyl}methyl)cyclohexanecarboxamide;

3-{4-(methylamino)-6-[(cis-4-{[({2-[(trifluoromethyl)oxy]phenyl}methyl)amino]carbonyl}cyclohexyl)amino]-1,3,5-triazin-2-yl}benzoic acid;

3-[4-(methylamino)-6-({cis-4-[({[4-(methyloxy)-2-(trifluoromethyl)phenyl]methyl}amino)carbonyl]cyclohexyl}amino)-1,3,5-triazin-2-yl]benzoic acid;

cis-4-({4-(methylamino)-6-[4-(trifluoromethyl)phenyl]-1,3,5-triazin-2-yl}amino)-N-{[4-(methyloxy)-2-(trifluoromethyl)phenyl]methyl}cyclohexanecarboxamide;

cis-4-{[4-(methylamino)-6-(3-pyridinyl)-1,3,5-triazin-2-yl]amino}-N-{[4-(methyloxy)-2-(trifluoromethyl)phenyl]methyl}cyclohexanecarboxamide;

cis-4-({4-(methylamino)-6-[4-(methylsulfonyl)phenyl]-1,3,5-triazin-2-yl}amino)-N-{[4-(methyloxy)-2-(trifluoromethyl)phenyl]methyl}cyclohexanecarboxamide;

3-[4-(methylamino)-6-({cis-4-[({[4-(trifluoromethyl)-3-pyridinyl]methyl}amino)carbonyl]cyclohexyl}amino)-1,3,5-triazin-2-yl]benzoic acid;

cis-4-({4-(methylamino)-6-[4-(trifluoromethyl)phenyl]-1,3,5-triazin-2-yl}amino)-N-{[4-(trifluoromethyl)-3-pyridinyl]methyl}cyclohexanecarboxamide;

cis-4-{[4-(methylamino)-6-(3-pyridinyl)-1,3,5-triazin-2-yl]amino}-N-{[4-(trifluoromethyl)-3-pyridinyl]methyl}cyclohexanecarboxamide;

cis-4-({4-(methylamino)-6-[4-(methylsulfonyl)phenyl]-1,3,5-triazin-2-yl}amino)-N-{[4-(trifluoromethyl)-3-pyridinyl]methyl}cyclohexanecarboxamide;

3-[4-{[cis-4-({[(2-chloro-4-cyanophenyl)methyl]amino}carbonyl)cyclohexyl]amino}-6-(methylamino)-1,3,5-triazin-2-yl]benzoic acid;

cis-N-[(2-chloro-4-cyanophenyl)methyl]-4-{[4-(methylamino)-6-(3-pyridinyl)-1,3,5-triazin-2-yl]amino}cyclohexanecarboxamide;

cis-4-({4-[(2-hydroxyethyl)amino]-6-methyl-1,3,5-triazin-2-yl}amino)-N-{[2-(trifluoromethyl)phenyl]methyl}cyclohexanecarboxamide;

cis-4-{[4-methyl-6-(4-methyl-1-piperazinyl)-1,3,5-triazin-2-yl]amino}-N-{[2-(trifluoromethyl)phenyl]methyl}cyclohexanecarboxamide;

cis-4-({4-methyl-6-[(phenylmethyl)amino]-1,3,5-triazin-2-yl}amino)-N-{[2-(trifluoromethyl)phenyl]methyl}cyclohexanecarboxamide;

cis-4-[(4-methyl-6-{[2-(methyloxy)ethyl]amino}-1,3,5-triazin-2-yl)amino]-N-{[2-(trifluoromethyl)phenyl]methyl}cyclohexanecarboxamide;

cis-4-{[4-(dimethylamino)-6-methyl-1,3,5-triazin-2-yl]amino}-N-{[2-(trifluoromethyl)phenyl]methyl}cyclohexanecarboxamide;

cis-4-{[4-methyl-6-(1-piperidinyl)-1,3,5-triazin-2-yl]amino}-N-{[2-(trifluoromethyl)phenyl]methyl}cyclohexanecarboxamide;

cis-4-[(4-amino-6-methyl-1,3,5-triazin-2-yl)amino]-N-{[2-(trifluoromethyl)phenyl]methyl}cyclohexanecarboxamide;

N-[(2,4-dichlorophenyl)methyl]-3-{[4-methyl-6-(methylamino)-1,3,5-triazin-2-yl]amino}cyclohexanecarboxamide;

cis-3-{[4-methyl-6-(methylamino)-1,3,5-triazin-2-yl]amino}-N-{[2-(trifluoromethyl)phenyl]methyl}cyclohexanecarboxamide;

cis-3-{[4-methyl-6-(methylamino)-1,3,5-triazin-2-yl]amino}-N-({2-[(trifluoromethyl)oxy]phenyl}methyl)cyclohexanecarboxamide;

cis-N-{[4-chloro-2-(trifluoromethyl)phenyl]methyl}-3-{[4-methyl-6-(methylamino)-1,3,5-triazin-2-yl]amino}cyclohexanecarboxamide;

(cis)-N-({2-chloro-4-[(methylsulfonyl)amino]phenyl}methyl)-3-{[4-methyl-6-(methylamino)-1,3,5-triazin-2-yl]amino}cyclohexanecarboxamide;

(cis)-N-{[2-chloro-4-(dimethylamino)phenyl]methyl}-3-{[4-methyl-6-(methylamino)-1,3,5-triazin-2-yl]amino}cyclohexanecarboxamide;

(cis)-N-[(2-chloro-4-cyanophenyl)methyl]-3-{[4-methyl-6-(methylamino)-1,3,5-triazin-2-yl]amino}cyclohexanecarboxamide;

(cis)-N-{[2-chloro-4-(1H-tetrazol-5-yl)phenyl]methyl}-3-{[4-methyl-6-(methylamino)-1,3,5-triazin-2-yl]amino}cyclohexanecarboxamide;
(cis)-3-{[4-methyl-6-(methylamino)-1,3,5-triazin-2-yl]amino}-N-{[3-(trifluoromethyl)-4-pyridinyl]methyl}cyclohexanecarboxamide;
(cis)-3-{[4-(2-fluorophenyl)-6-(methylamino)-1,3,5-triazin-2-yl]amino}-N-{[2-(trifluoromethyl)phenyl]methyl}cyclohexanecarboxamide;
(cis)-3-{[4-(4-fluorophenyl)-6-(methylamino)-1,3,5-triazin-2-yl]amino}-N-{[2-(trifluoromethyl)phenyl]methyl}cyclohexanecarboxamide;
(cis)-3-{[4-(4-cyanophenyl)-6-(methylamino)-1,3,5-triazin-2-yl]amino}-N-{[2-(trifluoromethyl)phenyl]methyl}cyclohexanecarboxamide;
(cis)-4-{[4-methyl-6-(methylamino)-1,3,5-triazin-2-yl]amino}-N-{[2-(trifluoromethyl)phenyl]methyl}cyclohexanecarboxamide;
cis-4-{[4-methyl-6-(methylamino)-1,3,5-triazin-2-yl]amino}-N-({2-[(trifluoromethyl)oxy]phenyl}methyl)cyclohexanecarboxamide;
cis-N-[(2,4-dichlorophenyl)methyl]-4-{[4-methyl-6-(methylamino)-1,3,5-triazin-2-yl]amino}cyclohexanecarboxamide
cis-N-{[4-chloro-2-(trifluoromethyl)phenyl]methyl}-4-{[methyl-6-(methylamino)-1,3,5-triazin-2-yl]amino}cyclohexanecarboxamide;
cis-4-{[4-methyl-6-(methylamino)-1,3,5-triazin-2-yl]amino}-N-({2-[(trifluoromethyl)thio]phenyl}methyl)cyclohexanecarboxamide;
trans-4-{[4-methyl-6-(methylamino)-1,3,5-triazin-2-yl]amino}-N-{[2-(trifluoromethyl)phenyl]methyl}cyclohexanecarboxamide;
trans-4-{[4-methyl-6-(methylamino)-1,3,5-triazin-2-yl]amino}-N-({2-[(trifluoromethyl)oxy]phenyl}methyl)cyclohexanecarboxamide;
cis-4-{methyl[4-methyl-6-(methylamino)-1,3,5-triazin-2-yl]amino}-N-{[2-(trifluoromethyl)phenyl]methyl}cyclohexanecarboxamide;
cis-4-{methyl[4-methyl-6-(methylamino)-1,3,5-triazin-2-yl]amino}-N-({2-[(trifluoromethyl)oxy]phenyl}methyl)cyclohexanecarboxamide;
cis-N-[(2,4-dichlorophenyl)methyl]-4-{methyl[4-methyl-6-(methylamino)-1,3,5-triazin-2-yl]amino}cyclohexanecarboxamide;
cis-N-{[4-chloro-2-(trifluoromethyl)phenyl]methyl}-4-{methyl[4-methyl-6-(methylamino)-1,3,5-triazin-2-yl]amino}cyclohexanecarboxamide;
trans-4-{[4-(methylamino)-6-phenyl-1,3,5-triazin-2-yl]amino}-N-{[2-(trifluoromethyl)phenyl]methyl}cyclohexanecarboxamide;
trans-4-{[4-(methylamino)-6-phenyl-1,3,5-triazin-2-yl]amino}-N-({2-[(trifluoromethyl)oxy]phenyl}methyl)cyclohexanecarboxamide
trans-N-[(2,4-dichlorophenyl)methyl]-4-{[4-(methylamino)-6-phenyl-1,3,5-triazin-2-yl]amino}cyclohexanecarboxamide;
trans-N-{[4-chloro-2-(trifluoromethyl)phenyl]methyl}-4-{[4-(methylamino)-6-phenyl-1,3,5-triazin-2-yl]amino}cyclohexanecarboxamide;
cis-4-{methyl[4-(methylamino)-6-phenyl-1,3,5-triazin-2-yl]amino}-N-{[2-(trifluoromethyl)phenyl]methyl}cyclohexanecarboxamide;
cis-4-{methyl[4-(methylamino)-6-phenyl-1,3,5-triazin-2-yl]amino}-N-({2-[(trifluoromethyl)oxy]phenyl}methyl)cyclohexanecarboxamide;
cis-N-[(2,4-dichlorophenyl)methyl]-4-{methyl[4-(methylamino)-6-phenyl-1,3,5-triazin-2-yl]amino}cyclohexanecarboxamide;
cis-N-{[4-chloro-2-(trifluoromethyl)phenyl]methyl}-4-{methyl[4-(methylamino)-6-phenyl-1,3,5-triazin-2-yl]amino}cyclohexanecarboxamide;
3-{[4-(methylamino)-6-phenyl-1,3,5-triazin-2-yl]amino}-N-[{2-(trifluoromethyl)phenyl]methyl}cyclohexanecarboxamide;
3-{[4-(methylamino)-6-phenyl-1,3,5-triazin-2-yl]amino}-N-({2-[(trifluoromethyl)oxy]phenyl}methyl)cyclohexanecarboxamide;
N-[(2,4-dichlorophenyl)methyl]-3-{[4-(methylamino)-6-phenyl-1,3,5-triazin-2-yl]amino}cyclohexanecarboxamide;
N-{[4-chloro-2-(trifluoromethyl)phenyl]methyl}-3-{[4-methyl-6-(methylamino)-1,3,5-triazin-2-yl]amino}cyclohexanecarboxamide;
cis-N-[(2,4-dichlorophenyl)methyl]-4-{[4-(methylamino)-6-phenyl-1,3,5-triazin-2-yl]amino}cyclohexanecarboxamide;
4-{[({cis-4-[(4-(methylthio)-6-{[(2R)-2-phenylpropyl]amino}-1,3,5-triazin-2-yl)amino]cyclohexyl}carbonyl)amino]methyl}benzoic acid;
cis-N-({4-bromo-2-[(trifluoromethyl)oxy]phenyl}methyl)-3-{[4-methyl-6-(methylamino)-1,3,5-triazin-2-yl]amino}cyclohexanecarboxamide;
cis-3-{[4-methyl-6-(methylamino)-1,3,5-triazin-2-yl]amino}-N-({4-(4-morpholinyl)-2-[(trifluoromethyl)oxy]phenyl}methyl)cyclohexanecarboxamide;
cis-3-{[4-methyl-6-(methylamino)-1,3,5-triazin-2-yl]amino}-N-({4-(1-piperidinyl)-2-[(trifluoromethyl)oxy]phenyl}methyl)cyclohexanecarboxamide;
cis-3-{[4-methyl-6-(methylamino)-1,3,5-triazin-2-yl]amino}-N-({4-(1-pyrrolidinyl)-2-[(trifluoromethyl)oxy]phenyl}methyl)cyclohexanecarboxamide;
cis-N-{[2-chloro-4-(1-piperidinyl)phenyl]methyl}-3-{[4-methyl-6-(methylamino)-1,3,5-triazin-2-yl]amino}cyclohexanecarboxamide;
(cis)-3-{[4-methyl-6-(methylamino)-1,3,5-triazin-2-yl]amino}-N-{[4-(methyloxy)-2-(trifluoromethyl)phenyl]methyl}cyclohexanecarboxamide;
(cis)-N-{[4-fluoro-2-(trifluoromethyl)phenyl]methyl}-3-{[4-methyl-6-(methylamino)-1,3,5-triazin-2-yl]amino}cyclohexanecarboxamide; and
(cis)-N-{[4-cyano-2-(trifluoromethyl)phenyl]methyl}-3-{[4-methyl-6-(methylamino)-1,3,5-triazin-2-yl]amino}cyclohexanecarboxamide.

Compound Preparation

The compounds according to Formula I are prepared using conventional organic syntheses. Suitable synthetic routes are depicted below in the following general reaction schemes. All functional groups are as defined in Formula I unless otherwise defined. Starting materials and reagents depicted below in the general reaction schemes are commercially available or can be made from commercially available starting materials using methods known by those skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and methods for protecting and de-protecting different substituents using such suitable protecting groups are well known to those skilled in the art; examples of which may be found in T.

Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

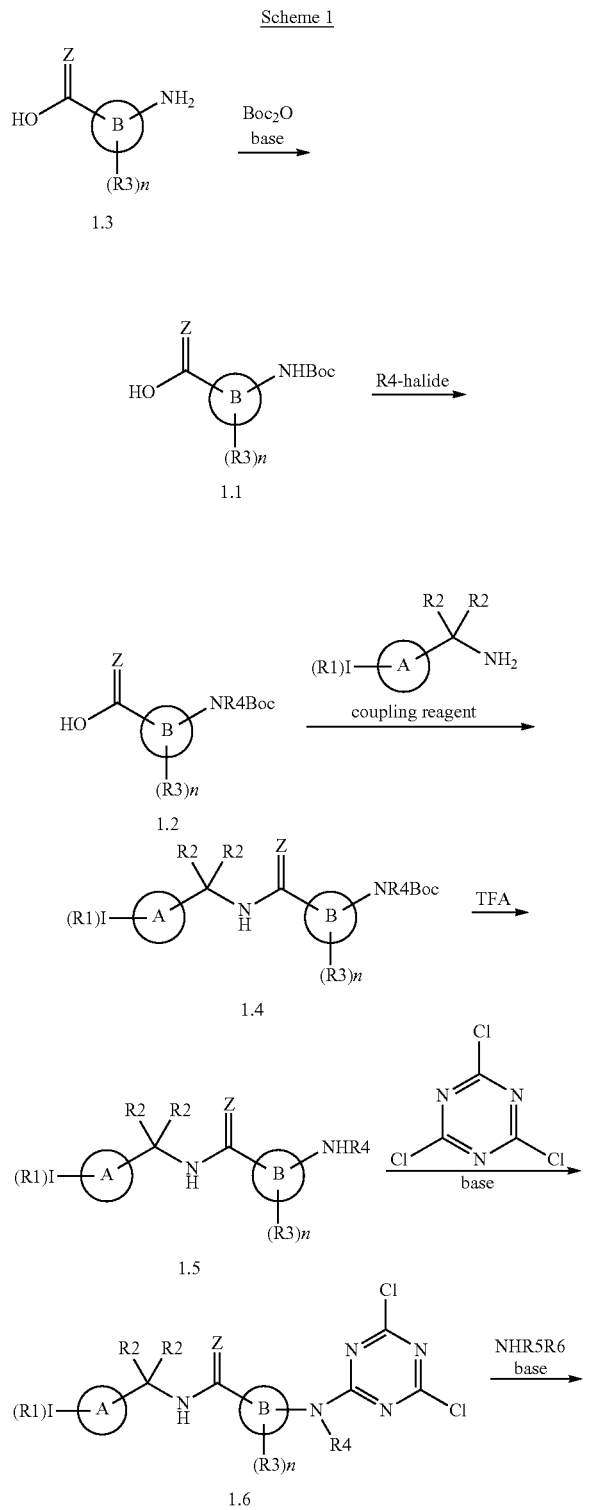

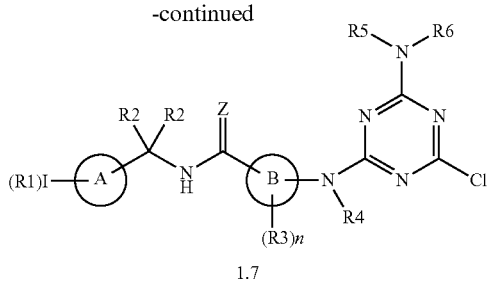

Scheme 1 represents a general reaction scheme for preparing intermediate 1.7. Boc-protected amino acid 1.1 can be obtained by treatment of the corresponding amino acid (commercially available or made from commercially available starting materials using methods known to those skilled in the art) with Boc$_2$O and a base (such as NaOH) in a solvent (such as 1,4-dioxane and water) at temperatures between 0 and 50° C. When R4 is to be R41 or R42, alkylation of the boc-protected amino acid 1.1 using R4-halide (commercially available or made from commercially available starting materials using methods known to those skilled in the art) and a base (such as NaH) in a solvent (such as DMF) at temperatures between 0 and 50° C. provides boc-protected amino acid 1.2. Amide intermediate 1.4 can be prepared by treatment of intermediates 1.1 or 1.2 with amine 1.3 (commercially available or made from commercially available starting materials using methods known to those skilled in the art) and an amide coupling reagent (such as EDCl or BOP) in a solvent (such as DMF) at room temperature. Hydrolysis of the boc-protecting group of intermediate 1.4 can be achieved using TFA to provide intermediate 1.5. Di-chlorotriazine intermediate 1.6 can be synthesized by the treatment of cyanuric chloride (commercially available) with 1 equivalent of intermediate 1.5 and a base (such as NaOH or Hünig's base) in a solvent (such as MeCN and water) at 0° C. Subsequent addition of 1 equivalent of HNR5R6 (commercially available or made from commercially available starting materials using methods known to those skilled in the art) and a base (such as NaOH or Hünig's base) in a solvent (such as MeCN and water) at temperatures between 25 and 50° C. provides mono-chlorotriazine 1.7.

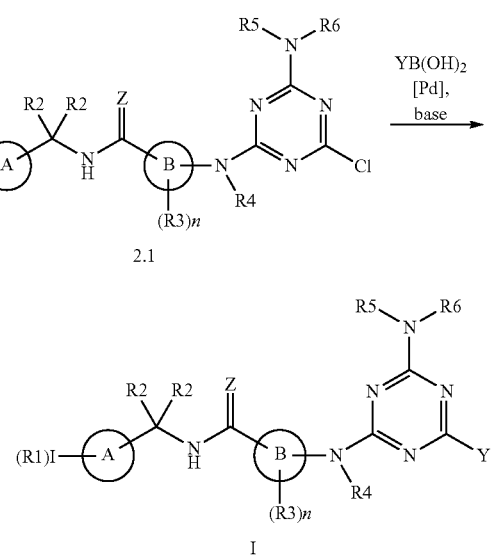

Scheme 2 represents a general reaction scheme for preparing certain compounds according to Formula I. Mono-chlorotriazine 2.1 (depicted above as intermediate 1.7) can be treated with YB(OH)$_2$ (commercially available or made from commercially available starting materials using methods known to those skilled in the art), a palladium source (such as PdCl$_2$(dppf)$_2$), and a base (such as K$_2$CO$_3$) in a solvent (such as THF) at temperatures between 80 and 170° C. (thermal or microwave heat) to provide compounds according to Formula I wherein Y is R7, R8, R9, R10, or R11.

boc-protecting group of intermediate 3.2 can be achieved using TFA providing amino acid 3.3. 2,4-Dichlorotriazine 3.4 can be synthesized by addition of 1 equivalent of the appropriate Grignard reagent (commercially available or made from commercially available starting materials using methods known to those skilled in the art) to cyanuric chloride (commercially available) in a solvent (such as THF) at 0° C. Intermediate 3.4 can be treated with 1 equivalent of HNR5R6 (commercially available or made from commercially available starting materials using methods known to those skilled

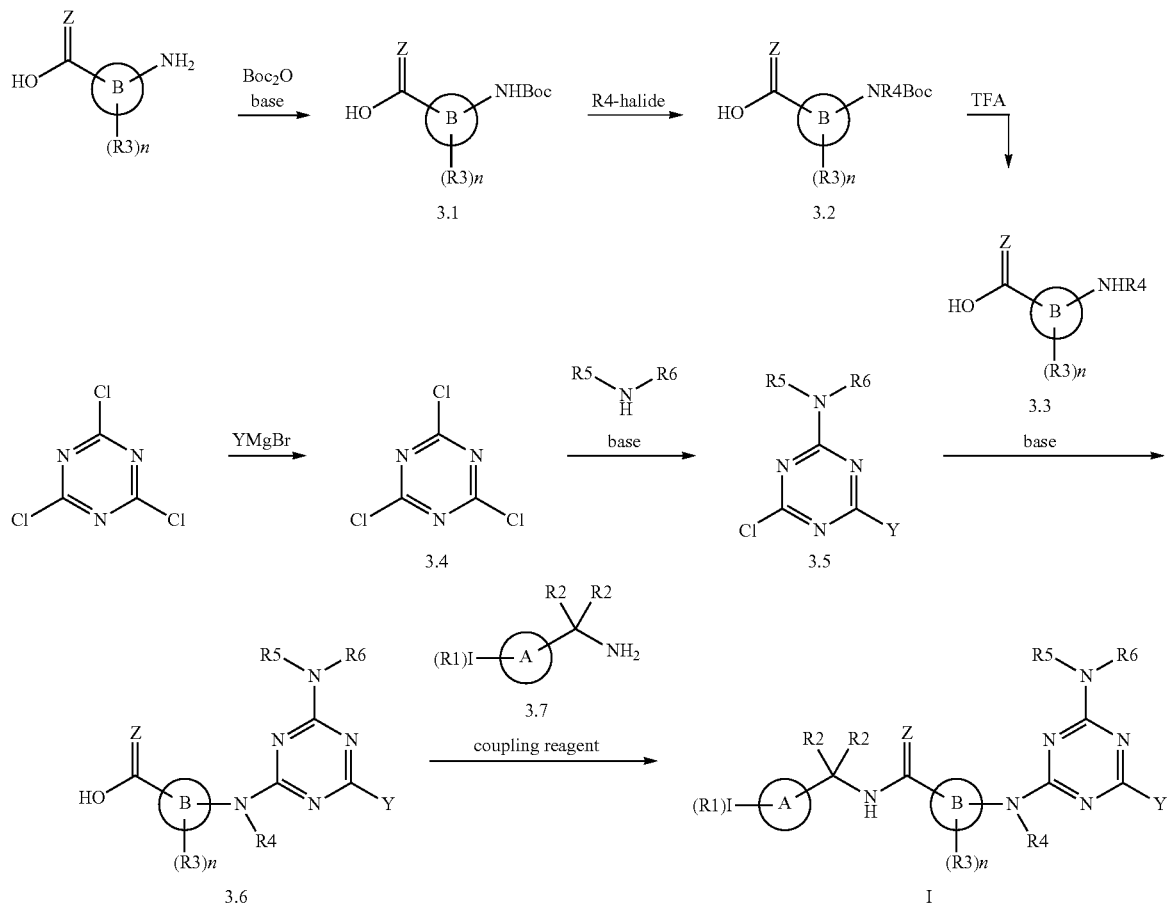

Scheme 3

Scheme 3 represents a general reaction scheme for preparing certain compounds according to Formula I. Boc-protected amino acid 3.1 can be obtained by treatment of the corresponding amino acid (commercially available or made from commercially available starting materials using methods known to those skilled in the art) with Boc$_2$O and a base (such as NaOH) in a solvent (such as 1,4-dioxane and water) at temperatures between 0 and 50° C. When R4 is to be R41 or R42, alkylation of boc-protected amino acid 3.1 using R4-halide (commercially available or made from commercially available starting materials using methods known to those skilled in the art) and a base (such as NaH) in a solvent (such as DMF) at temperatures between 0 and 50° C. provides boc-protected amino acid 3.2. Subsequent hydrolysis of the in the art) and a base (such as NaOH or Hünig's base) in a solvent (such as MeCN and water) at temperatures between 25 and 50° C. Resulting intermediate 3.5 can be reacted with excess amino acid 3.3 at elevated temperature (60 to 90° C.) in a solvent (such as MeCN and water) to afford carboxylic acid 3.6. Intermediate 3.6 can be treated with amine 3.7 (commercially available or made from commercially available starting materials using methods known to those skilled in the art) and a coupling reagent (such as EDCl or BOP) in a solvent (such as DMF) at room temperature to yield compounds according to Formula I wherein Y is R7, R8, R9, R10, or R11.

Scheme 4

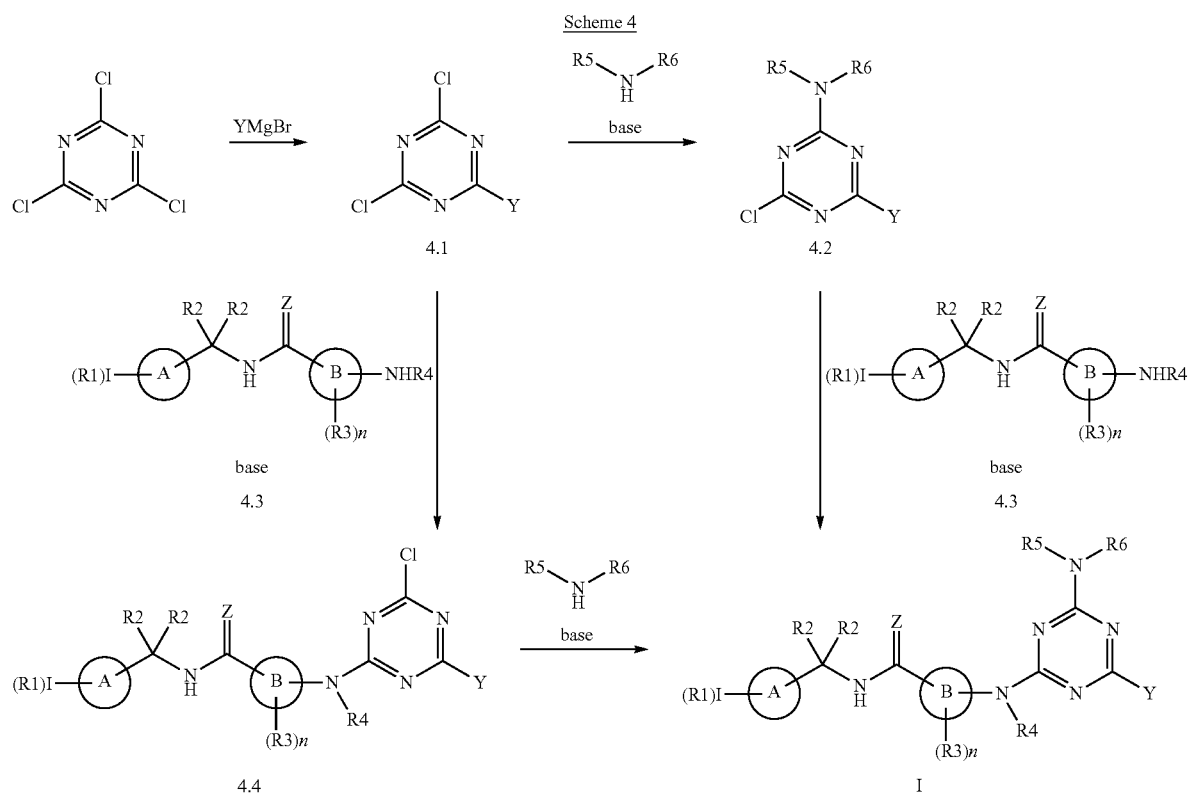

Scheme 4 represents a general reaction scheme for preparing certain compounds according to Formula I. 2,4-Dichlorotriazine 4.1 can be synthesized by addition of 1 equivalent of the appropriate Grignard reagent (commercially available or made from commercially available starting materials using methods known to those skilled in the art) to cyanuric chloride (commercially available) at 0° C. in a solvent (such as THF). Intermediates 4.1 can be treated with 1 equivalent of amide 4.3 (depicted above as intermediate 1.5) and a base (such as NaOH or Hünig's base) in a solvent (such as MeCN and water) at temperatures between 25 and 50° C. to afford mono-chlorotriazine 4.4. Intermediate 4.4 can be treated with excess HNR5R6 (commercially available or made from commercially available starting materials using methods known to those skilled in the art) and a base (such as NaOH or Hünig's base) in a solvent (such as MeCN and water) at elevated temperature (60 to 80° C.) to provide compounds according to Formula I wherein Y is R7, R8, R9, R10, or R11.

Alternatively, intermediate 4.1 can be treated with 1 equivalent of HNR5R6 (commercially available or made from commercially available starting materials using methods known to those skilled in the art) and a base (such as NaOH or Hünig's base) in a solvent (such as MeCN and water) at temperatures between 25 and 50° C. to afford mono-chlorotriazine 4.2. Intermediate 4.2 can be treated with excess amide 4.3 and a base (such as NaOH or Hünig's base) in a solvent (such as MeCN and water) at elevated temperature (60 to 80° C.) to provide compounds according to Formula I wherein Y is R7, R8, R9, R10, or R11.

Scheme 5

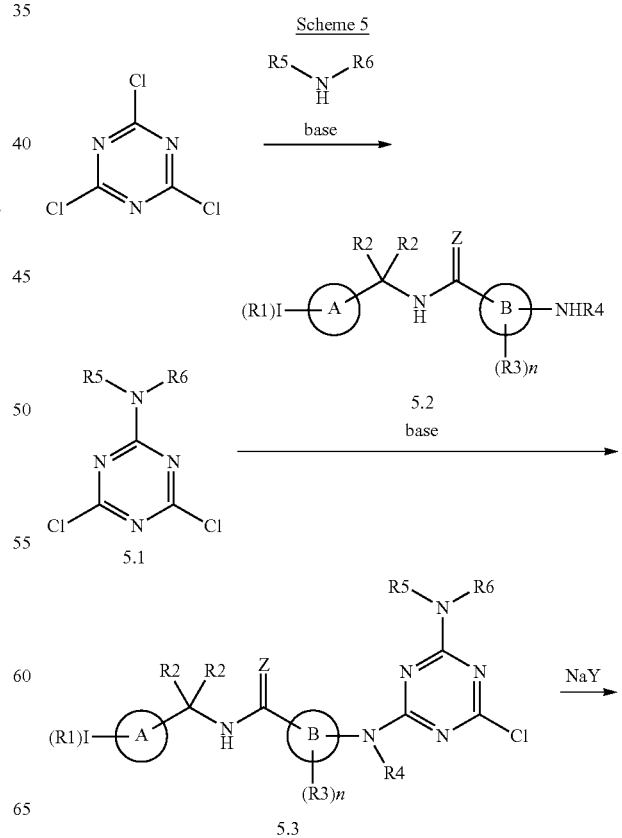

-continued

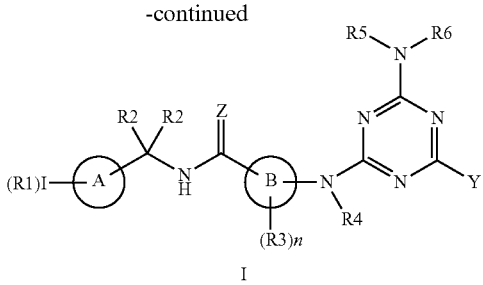

Scheme 5 represents a general reaction scheme for preparing certain compounds according to Formula I. Dichlorotriazine 5.1 can be synthesized by treatment of cyanuric chloride (commercially available) with 1 equivalent of HNR5R6 (commercially available or made from commercially available starting materials using methods known to those skilled in the art) and a base (such as NaOH or Hünig's base) in a solvent (such as MeCN and water) at 0° C. Subsequent addition of 1 equivalent of amide 5.2 (depicted above as intermediate 1.5) and a base (such as NaOH or Hünig's base) in a solvent (such as MeCN and water) at temperatures between 25 and 50° C. affords mono-chlorotriazine 5.3. Intermediate 5.3 may then be treated with excess NaY (commercially available or made from commercially available starting materials using methods known to those skilled in the art) to provide compounds according to Formula I wherein Y is R12.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Intermediate 1 cis-4-amino-N-{[2-(trifluoromethyl)phenyl]methyl}cyclohexanecarboxamide

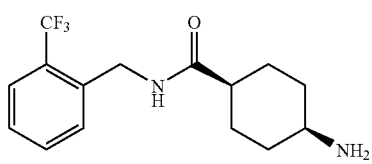

Step 1: cis-4-({[(1,1-dimethylethyl)oxy]carbonyl}amino)cyclohexanecarboxylic acid

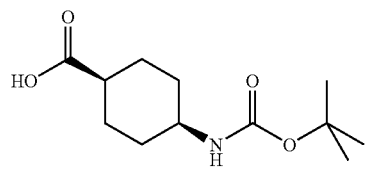

To a flask charged with cis-4-aminocyclohexanecarboxylic acid (4.3 g, 30 mmol, 1.0 equiv), 1,4-dioxane (36 mL) was added. The suspension was cooled to 0° C., and 1.0 N sodium hydroxide (72 mL, 72 mmol, 2.4 equiv) was added over 5 min. The solution was stirred for 20 min at 0° C. A solution of bis(1,1-dimethylethyl) dicarbonate (7.87 g, 36.0 mmol, 1.1 equiv) in 1,4-dioxane (36 ml) was added over 5 min. The reaction was allowed to warm to room temperature and stirring was continued overnight. The reaction was cooled to 0° C. and acidified (to ~pH 4) with 1.5 M potassium hydrogen sulfate. The desired product was extracted with ethyl acetate (3×), dried with sodium sulfate, filtered and concentrated under reduced pressure to afford 6.55 g (90%) of the title compound. MS (ES+): m/e 265.9 [M+Na]⁺.

Step 2: 1,1-dimethylethyl{cis-4-[({[2-(trifluoromethyl)phenyl]methyl}amino)carbonyl]cyclohexyl}carbamate

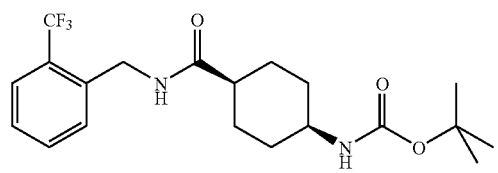

To a solution of cis-4-({[(1,1-dimethylethyl)oxy]carbonyl}amino)cyclohexanecarboxylic acid (3.0 g, 12 mmol, 1.0 equiv) and 1-[2-(trifluoromethyl)phenyl]methanamine (1.9 mL, 14 mmol, 1.0 equiv) in CH₂Cl₂ (82 mL) at room temperature, DMAP (301 mg, 2.47 mmol, 0.2 equiv) was added. EDC (2.95 g, 15.4 mmol, 1.25 equiv), and diisopropylethylamine (DIEA, 2.7 ml, 15 mmol, 1.25 equiv) were added. Stirring was continued overnight at room temperature. The solution was diluted with CH₂Cl₂ (100 ml), washed with saturated sodium bicarbonate (200 mL), water (200 mL), and brine (200 mL). The CH₂Cl₂ extracts were dried with MgSO₄, filtered, and concentrated under reduced pressure to yield the title compound. MS (ES+): m/e 400.8 [M+Na]⁺.

Step 3: cis-4-amino-N-{[2-(trifluoromethyl)phenyl]methyl}cyclohexanecarboxamide

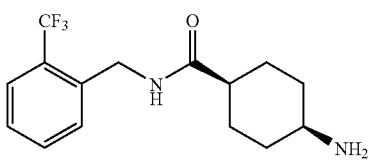

To a solution of 1,1-dimethylethyl {cis-4-[({[2-(trifluoromethyl)phenyl]methyl}amino)carbonyl]cyclohexyl}carbamate in CH₂Cl₂ (40 ml) at 0° C., a premixed solution of CH₂Cl₂ (10 ml) and TFA (10 ml) was added. The reaction mixture was stirred at 0° C. for 10 min. The reaction was warmed to room temperature and stirring was continued for 2 h. The solvent was next removed under reduced pressure to yield 2.83 g (69% over 2 steps) of the title compound. MS ES+): m/e 301.1 [M+H]+.

Alternatively, Intermediate 1 can be Synthesized Using the Following Procedure

Step 1: cis-4-({[(1,1-dimethylethyl)oxy]carbonyl}amino)cyclohexanecarboxylic acid

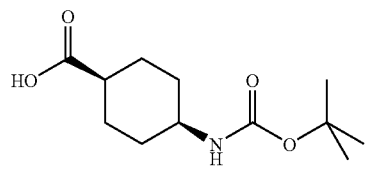

A 250 mL round-bottom flask charged with argon was equipped with a magnetic stir bar. cis-4-Aminocyclohexanecarboxylic acid (9.27 g, 64.7 mmol), isopropanol (83 mL) and 1 N NaOH (70.6 mL, 70.6 mmol) were added to the flask at room temperature. After all of the solid was dissolved, bis(tert-butyl) dicarbonate (15.54 g, 71.2 mmol) was added, the mixture was maintained at room temperature for 21 h. The crude mixture was washed with hexanes (3×100 mL). Afterwards, 100 mL of 1 N HCl was added to the aqueous layer and the mixture was extracted with ethyl acetate (300 mL). The organic phase was dried over Na₂SO₄, filtered and concentrated to give 12.85 g of cis-4-({[(1,1-dimethylethyl)oxy]carbonyl}amino)cyclohexane carboxylic acid (82%) as an off-white solid.

Step 2: 1,1-dimethylethyl{cis-4-[({[2(trifluoromethyl)phenyl]methyl}amino)carbonyl]cyclohexyl}carbamate

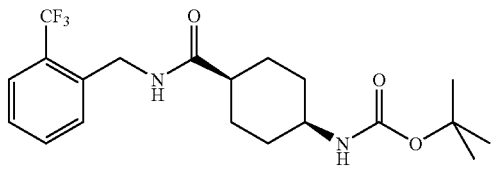

To a 250 mL round-bottom flask charged with argon was added cis-4-({[(1,1-dimethylethyl)oxy]carbonyl}amino)cyclohexanecarboxylic acid (15.54 g, 63.9 mmol), 2-(trifluoromethyl)benzylamine (8.95 mL, 63.9 mmol) and 100 mL of DMF. Triethylamine (26.7 mL, 192 mmol) was added, and the solution was allowed to stir for several minutes. Next, a separate solution of 1H-1,2,3-benzotriazol-1-yloxy-tris(dimethylamino)-phosphonium hexafluorophosphate (BOP reagent, 28.3 g, 63.9 mmol) dissolved in 60 mL of DMF was added to the mixture at room temperature. The reaction mixture stirred for 2 h and then poured into a vigorously stirring mixture of saturated sodium bicarbonate and (1:1, 1.6 L). This resulted in the precipitation of the desired product as an off-white solid. The solid was recovered by vacuum filtration and was dried for 24 h under vacuum to give 24.88 g of 1,1-dimethylethyl{cis-4-[({[2(trifluoromethyl)phenyl] methyl}amino)carbonyl]cyclohexyl}carbamate (62.1 mmol, 97%). MS (ES) m/e 401 [M+H]+.

Step 3: cis-4-amino-N-{[2-(trifluoromethyl)phenyl]methyl}cyclohexanecarboxamide

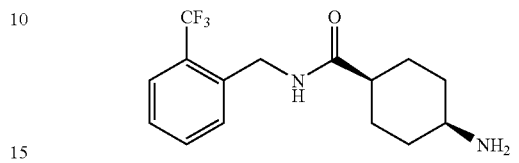

A 500 mL round bottom flask equipped with a magnetic stir bar was charged with 1,1-dimethylethyl{cis-4-[({[2(trifluoromethyl)phenyl]methyl}amino)carbonyl]cyclohexyl}carbamate (24.88 g, 62.1 mmol) and dichloromethane (100 mL). Trifluoroacetic acid (100 mL) was added slowly, and the reaction mixture was stirred at room temperature for 1 h. The volatile components were removed by rotary evaporation, and the crude oil was dissolved in ethyl acetate and washed with saturated sodium bicarbonate solution (3×200 mL). The organic phase was dried over Na₂SO₄, filtered and concentrated to give 18.3 g of the title compound (98%) as an off-white solid. MS (ES) m/e 301 [M+H]+.

Intermediate 2 cis-4-amino-N-({2-[(trifluoromethyl)oxy]phenyl}methyl)cyclohexanecarboxamide

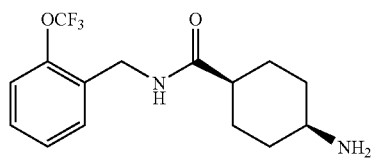

Intermediate 2 was prepared using the general procedure described above in the synthesis of Intermediate 1 substituting 2-[(trifluoromethyl)oxy]benzylamine for 2-(trifluoromethyl)benzylamine. MS (ES+): [M+H]+.

Intermediate 3

N-[4-(aminomethyl)-3-chlorophenyl]methanesulfonamide

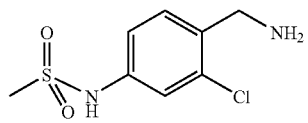

Step 1:
N-(3-chloro-4-cyanophenyl)methanesulfonamide

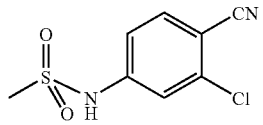

To a solution of 4-amino-2-chlorobenzonitrile (5 g, 32.8 mmol) and pyridine (3.18 mL, 39.3 mmol) in Dichloromethane (DCM) (75 mL) was added methanesulfonyl chloride (4.50 g, 39.3 mmol) slowly at 0° C. under the $N_2$. After addition, the mixture was warmed to room temperature and stirred overnight. The reaction mixture was treated with 50 mL of 2N NaOH. The layers were separated. The aqueous layer was acidified with conc.HCl to pH=2, which resulted in the precipitation of product. The solids were filtered, washed with water, and dried to give the desired product as a white solid (7.0 g, 93%). MS (ES+): m/e 230.8 $[M+H]^+$.

Step 2: N-[4-(aminomethyl)-3-chlorophenyl]methanesulfonamide

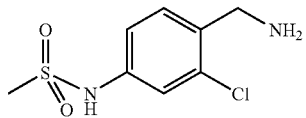

In a three-neck round-bottom flask containing a 0° C. solution of LiAlH₄ (2M in THF) (26.0 mL, 52.0 mmol) was added iodine (6.60 g, 26.0 mmol) in THF (20 mL) dropwise under $N_2$. After addition, the mixture was stirred for 30 min at 0° C. N-(3-chloro-4-cyanophenyl)methanesulfonamide (4 g, 17.34 mmol) in THF (20 mL) was then added dropwise. After addition, the reaction mixture was warmed to room temperature and stirred for 1 h, during which time precipitate crashed out of the solution. The reaction mixture was filtered, and the cake washed with cold THF. The cake was carefully transferred to a beaker which contained 60 mL of THF. The mixture was acidified to pH=2 with 6N HCl with constant stirring at 0° C. The layers were separated and the aqueous layer was washed with DCM (30 mL). The aqueous layer was concentrated by rotary evaporation. The resulting solids were washed with cold MeOH to give a yellow solid. The mother liquid was subjected to the same workup (2×). The combined crops were collected and dried to give the title compound as the HCl salt (4.2 g, 89%). MS (ES+): m/e 234.7 $[M+H]^+$.

Intermediate 4

[4-(aminomethyl)-3-chlorophenyl]dimethylamine

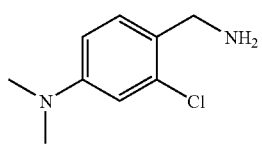

Step 1: 2-chloro-4-(dimethylamino)benzonitrile

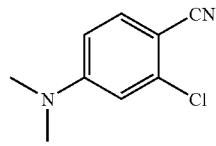

A mixture of 4-amino-2-chlorobenzonitrile (1 g, 6.55 mmol), iodomethane (7.44 g, 52.4 mmol) and cesium carbonate (4.27 g, 13.11 mmol) in acetonitrile (10 mL) were heated to 100° C. in a sealed-tube. After stirring overnight, water (15 mL) was added to the mixture, followed by EtOAc (25 mL). The organic layer was separated and the aqueous re-extracted with EtOAc (25 mL). The organics were dried over $Na_2SO_4$ and evacuated. Column chromatography (EtOAc/Hexanes=0-40%) afforded the desired product as a white solid (0.76 g, 64%). MS (ES+): m/e 180.8 $[M+H]^+$.

Step 2:
[4-(aminomethyl)-3-chlorophenyl]dimethylamine

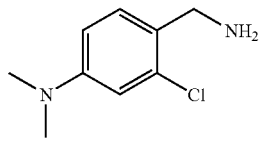

To a solution of 2-chloro-4-(dimethylamino)benzonitrile (0.76 g, 4.21 mmol) in THF (5 mL) was added 1M LiAlH₄/I₂ in THF (8.41 ml, 8.41 mmol, as prepared in Step 2 of Intermediate 3). The mixture was stirred for 10 min, at which time LCMS indicated the formation of the desired product. Water (15 mL) was added to the mixture, which was acidified to pH=2 with 6N HCl. The aqueous layer was separated and washed with $Et_2O$ (2×25 mL). The aqueous layer was then basified with 6N NaOH, and extracted with $Et_2O$ (3×30 mL). The organics were dried over $Na_2SO_4$. The ether layer was evacuated to ⅓ volume at which time 8 mL of 1M HCl in ether solution was added. After stirring for 10 minutes, solids precipitated from solution. The solids were filtered, washed with ether and dried to afford the title compound (1.0 g, 92%) as a light yellow solid. MS (ES+): m/e 185.0 $[M+H]^+$.

Intermediate 5

{[4-(methyloxy)-2-(trifluoromethyl)phenyl]methyl}amine

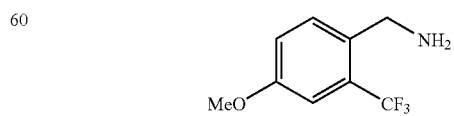

To a mixture of 4-(methyloxy)-2-(trifluoromethyl)benzaldehyde (14 g, 65 mmol, 1.0 equiv), aqueous $NH_3$ (25-28%, 370 mL, 5.20 mol, 80 equiv), and MeOH (300 mL) was added Raney-Ni (3.8 g, 65 mmol, 1.0 equiv). The flask was fitted with a hydrogen balloon, and the mixture was stirred for 7 days at room temperature. The reaction mixture was filtered through a celite cake, and the filtrate was concentrated. The residue was purified by HPLC to afford 9 g (64%) of the title compound as the trifluoroacetate salt. MS (ES+): m/e 206 [M+H]$^+$. $^1$H NMR (400 MHz, DMSO-D6) ☐7.6 (d, 1H), 7.3 (d, 1H), 7.2 (s, 1H), 4.1 (s, 2H), 3.8 (s, 3H)

Intermediate 6

4-(aminomethyl)-3-chlorobenzonitrile

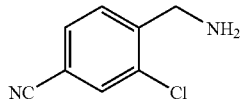

Step 1: 4-(bromomethyl)-3-chlorobenzonitrile

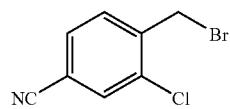

A mixture of 3-chloro-4-methylbenzonitrile (7.5 g, 50 mmol, 1.0 equiv), N-bromosuccinimide (9.14 g, 52 mmol, 1.1 equiv), and azobisisobutyronitrile (AIBN, 0.82 g, 5 mmol, 0.1 equiv) in carbon tetrachloride was heated to reflux temperature for 25 h. Water (50 mL) was added, and the product was extracted with CH$_2$Cl$_2$. The organic layers were washed with water, dried with MgSO$_4$, and evaporated to provide 11.3 g of the title compound. This material was used in the next step without purification.

Step 2: 4-(aminomethyl)-3-chlorobenzonitrile

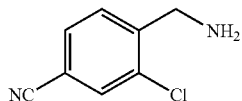

To a mixture of 4-(bromomethyl)-3-chlorobenzonitrile (11 g, 49 mmol, 1.0 equiv) and 6 M NH$_3$ in methanol (200 mL) was stirred at 18° C. for 17 h. Aqueous HCl (1 M, 200 mL) was added, and the water layer was washed with ethyl acetate. The aqueous phase was adjusted to pH 9-10 with 1 M NaOH and extracted with ethyl acetate. The organic layer was washed with water, dried with magnesium sulfate, and concentrated. The residue was purified on silica gel to afford 2.71 g of the title compound. MS (ES+): m/e 167.0 [M+H]$^+$.

Intermediate 7

{[4-(trifluoromethyl)-3-pyridinyl]methyl}amine

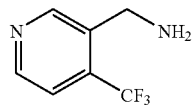

To a mixture of 4-(trifluoromethyl)-3-pyridinecarbonitrile (9.5 g, 55 mmol, 1.0 equiv) and 5 M NH$_3$ in methanol (600 mL, 3.0 mol, 54 equiv) was added Raney-Ni (3.0 g, 52 mmol, 0.95 equiv). The flask was fitted with a hydrogen balloon, and the mixture was stirred for 16 h. The reaction mixture was filtered, and the filtrate was concentrated. The residue was purified by HPLC to afford 10.5 g (47%) of the title compound as the bis-trifluoroacetate salt. MS (ES+): m/e 177.1 [M+H]$^+$.

Intermediate 8 cis-4-amino-N-({2-chloro-4-[(methylsulfonyl)amino]phenyl}methyl)cyclohexanecarboxamide

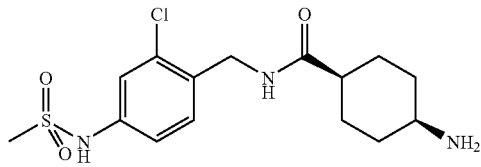

Intermediate 8 was prepared using the general procedure described above in the synthesis of Intermediate 1 substituting N-[4-(aminomethyl)-3-chlorophenyl]methanesulfonamide for 2-(trifluoromethyl)benzylamine. MS (ES+): m/e 359.9 [M+H]$^+$.

Intermediate 9 cis-4-amino-N-{[4-(methyloxy)-2-(trifluoromethyl)phenyl]methyl}cyclohexanecarboxamide

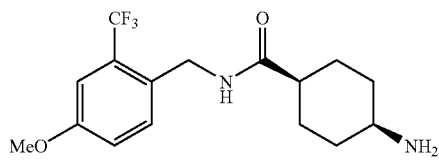

Intermediate 9 was prepared using the general procedure described above in the synthesis of Intermediate 1 substituting 1-[4-(methyloxy)-2-(trifluoromethyl)phenyl]methanamine for 2-(trifluoromethyl)benzylamine. MS (ES+): m/e 331.0 [M+H]⁺.

Intermediate 10 cis-4-amino-N-{[4-cyano-2-(trifluoromethyl)phenyl]methyl}cyclohexanecarboxamide

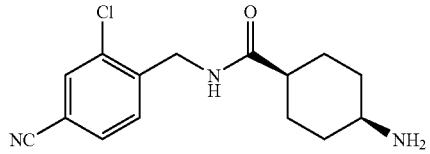

Intermediate 10 was prepared using the general procedure described above in the synthesis of Intermediate 1 substituting 4-(aminomethyl)-3-chlorobenzonitrile for 2-(trifluoromethyl)benzylamine. MS (ES+): m/e 292.0 [M+H]⁺.

Intermediate 11 cis-4-amino-N-{[4-(trifluoromethyl)-3-pyridinyl]methyl}cyclohexanecarboxamide

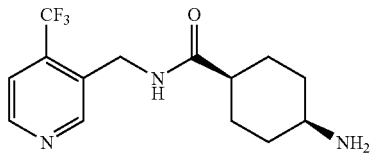

Intermediate 11 was prepared using the general procedure described above in the synthesis of Intermediate 1 substituting 1-[4-(trifluoromethyl)-3-pyridinyl]methanamine for 2-(trifluoromethyl)benzylamine. MS (ES+): 302.0 [M+H]⁺.

Intermediate 12 cis-4-{[4-chloro-6-(methylamino)-1,3,5-triazin-2-yl]amino}-N-{[2-(trifluoromethyl)phenyl]methyl}cyclohexanecarboxamide

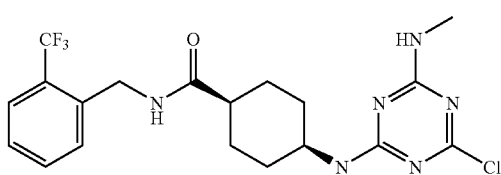

Step 1: cis-4-[(4,6-dichloro-1,3,5-triazin-2-yl)amino]-N-{[2-(trifluoromethyl)phenyl]methyl}cyclohexanecarboxamide

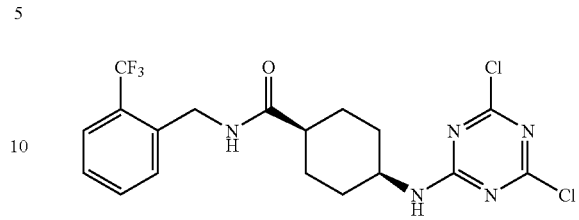

To a solution of 2,4,6-chloro-1,3,5-triazine (307 mg, 1.66 mmol, 1.00 equiv) in CH₂Cl₂ (6 mL) at −50° C., a premixed solution of diisopropylethylamine (DIEA, 1.45 ml, 8.30 mmol, 5.00 equiv) and Intermediate 1 (500 mg, 1.66 mmol, 1.00 equiv) in CH₂Cl₂ (3 mL) was added. The reaction was allowed to warm to room temperature and stirred for 3 h. The title compound was obtained and carried forward without workup or purification. MS (ES+): m/e 449.7 [M+H]⁺.

Step 2: cis-4-{[4-({2-[(phenylmethyl)thio]ethyl}amino)-1,3,5-triazin-2-yl]amino}-N-{[2-(trifluoromethyl)phenyl]methyl}cyclohexanecarboxamide

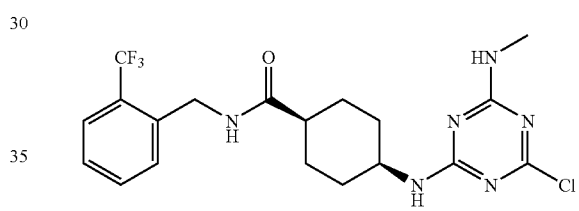

A premixed solution of diisopropylethylamine (DIEA, 0.872 mL, 4.98 mmol, 3 equiv) and methylamine (0.830 mL, 1.66 mmol, 1 equiv) in CH₂Cl₂ (3 mL) was added dropwise to the crude reaction mixture obtained in Step 1. The mixture was stirred for 3 h. The volatile components were removed under reduced pressure yielding 695 mg (94%) of the title compound. A portion of this material was purified via reverse-phase HPLC purification, and the remainder was used without purification. MS (ES+): m/e 443.9 [M+H]⁺.

Intermediate 13

2,4-dichloro-6-methyl-1,3,5-triazine

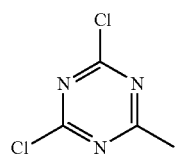

To a solution of 2,4,6-trichloro-1,3,5-triazine (20 g, 108 mmol, 1.0 equiv) in THF (8 mL) at −10° C., methylmagnesium bromide (45 ml, 135 mmol, 1.25 equiv) was added dropwise. The reaction mixture was allowed to warm to room temperature and was stirred for 2 h. The mixture was poured onto ice-water and stirred for an additional hour. The product was extracted with ethyl acetate, washed with brine, dried with sodium sulfate, filtered, and concentrated under reduced pressure to afford 14 g of the title compound. The crude product was carried forward in the next step. MS (ES+): m/e 186.1 [M+Na]$^+$.

Intermediate 14

{[2-chloro-4-(1H-tetrazol-5-yl)phenyl]methyl}amine

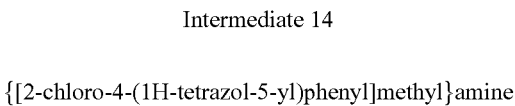

To a solution of Intermediate 6 (0.1 g, 0.600 mmol) and trimethylsilyl azide (0.159 ml, 1.200 mmol) in toluene (5 mL) was added dibutyltin oxide (0.015 g, 0.060 mmol). The mixture was stirred overnight at 100° C., at which time LCMS showed that the reaction to be complete. The reaction mixture was vacuum filtered. The filter cake was washed with cold MeOH, and dried to give the title compound as a light-brown solid (0.08 g, 63.6%). MS (ES+): m/e 210.0 [M+H]$^+$.

Intermediate 15

3-amino-N-{[2-(trifluoromethyl)phenyl]methyl}cyclohexanecarboxamide

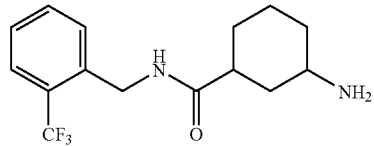

Intermediate 15 was prepared using the general procedure described above in the synthesis of Example 28 (Step 2) substituting 2-(trifluoromethyl)benzylamine for 2,4-dichlorobenzylamine. MS (ES+): m/e 301.1 [M+H]$^+$.

Intermediate 16 cis-4-(methylamino)cyclohexanecarboxylic acid

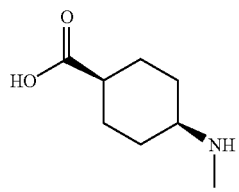

Step 1: cis-4-[{[(1,1-dimethylethyl)oxy]carbonyl}(methyl)amino]cyclohexanecarboxylic acid

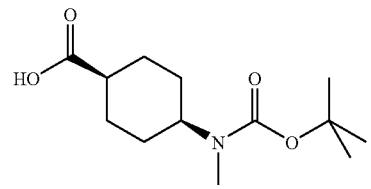

To a suspension of NaH (1.0 g, 41 mmol, 2.5 equiv) in DMF (30 mL) at −10° C. was added cis-4-({[(1,1-dimethylethyl)oxy]carbonyl}amino)cyclohexanecarboxylic acid (4.0 g, 16 mmol, 1.0 equiv). The reaction mixture was allowed to warm to room temperature and then was stirred for 1 h. The mixture was again cooled to −10° C., and MeI (25 g, 260 mmol, 16 equiv) was added dropwise. The cold bath was removed, and the reaction mixture was stirred for 3 h at room temperature. The mixture was poured onto ice, and then NaOH (1.5 g) was added to hydrolyze any undesired methyl ester that formed. This solution was stirred for another 4 hours. The aqueous layer was washed with ethyl acetate and concentrated under reduced pressure to remove the DMF. The resulting residue was diluted with water, and the pH was adjusted to ~3-4. The desired product precipitated as a white solid which was collected by filtration (2.5 g).

Step 3: cis-4-(methylamino)cyclohexanecarboxylic acid

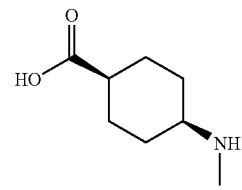

A solution of cis-4-[{[(1,1-dimethylethyl)oxy]carbonyl}(methyl)amino]cyclohexane carboxylic acid (2.5 g, 16 mmol, 1.0 equiv) and 1 M HCl in dioxane (15 mL) was heated to reflux for 4 h. The solvent was removed under reduced pressure to afford 1.3 g of the title compound. This material was used without purification.

Intermediate 17 cis-4-amino-N-[(2,4-dichlorophenyl)methyl]cyclohexanecarboxamide

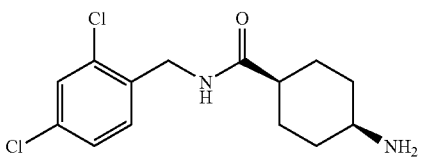

Intermediate 17 was prepared using the general procedure described above in the synthesis of Intermediate 1 substituting [(2,4-dichlorophenyl)methyl]amine for 2-(trifluoromethyl)benzylamine. MS (ES+): m/e 303.0 [M+H]+.

Intermediate 18

3-amino-N-({2-[(trifluoromethyl)oxy]phenyl}methyl)cyclohexanecarboxamide

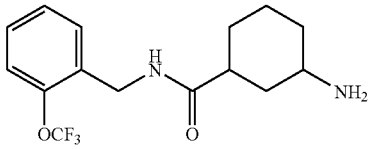

Intermediate 18 was prepared using the general procedure described above in the synthesis of Intermediate 15 substituting 2-[(trifluoromethyl)oxy]benzylamine for 2-(trifluoromethyl)benzylamine. MS (ES+): m/e 317.1 [M+H]+.

Intermediate 19

Preparation of 3-{[4-methyl-6-(methylamino)-1,3,5-triazin-2-yl]amino}cyclohexanecarboxylic acid

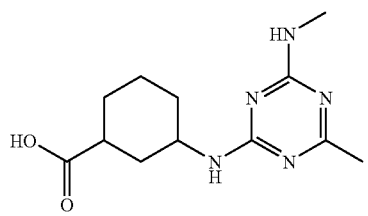

To a mixture of 2,4-dichloro-6-methyl-1,3,5-triazine (2.291 g, 13.97 mmol) and methylamine (6.98 ml, 13.97 mmol) was added 1N NaOH dropwise in order to maintain a pH of 10. The reaction was stirred for 30 minutes. Next, 3 aminocyclohexane-carboxylic acid (2.0 g, 13.97 mmol) was added in one portion, and 1N NaOH was added dropwise in order to maintain a pH of 10. The reaction was heated to 70° C. overnight. The reaction was cooled and purified directly by preparative HPLC. MS (ES+): m/e 266.2 [M+H]+. $^1$H NMR (400 MHz, DMSO-D6) ☐ 9.0-8.5 (bm, 2H), 3.9 (bs, 1H), 2.9 (m, 2H), 2.3 (s, 3H), 2.2 (s, 3H), 1.9-1.7 (bm, 4H), 1.4-1.1 (bm, 4H)

Intermediate 20: 1-{4-bromo-2-[(trifluoromethyl)oxy]phenyl}methanamine

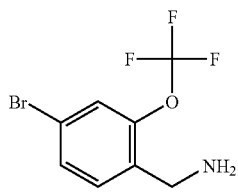

Step 1: 4-bromo-2-[(trifluoromethyl)oxy]benzaldehyde

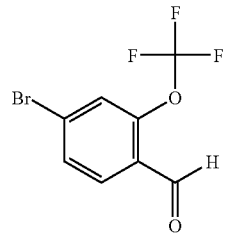

5-bromo-2-iodophenyl trifluoromethyl ether (500 mg, 1.37 mmol) was dissolved in 10 mL of anhydrous THF and cooled to −70° C. Then, n-butyllithium (0.55 mL of a 2.5 M solution, 1.37 mmol) was added dropwise over the course of 30 minutes. DMF (0.19 mL, 2.74 mmol) was added and the reaction was stirred for 30 minutes at −70° C. and then allowed to warm to 0° C. and stir for three hours. The reaction was quenched with 5 mL of saturated ammonium chloride solution and extracted with ethyl acetate. The organic layer was washed with water, dried over magnesium sulfate, filtered, and concentrated to provide 4-bromo-2-[(trifluoromethyl)oxy]benzaldehyde (100 mg, 0.37 mmol, 27%) as a yellow solid. $^1$H NMR (400 MHz, DMSO-D6) ☐ 10.1 (s, 1H), 7.9 (s, 3H)

Step 2: 1-{4-bromo-2-[(trifluoromethyl)oxy]phenyl}methanamine

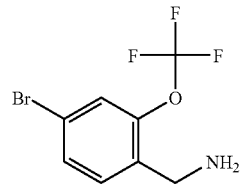

4-bromo-2-[(trifluoromethyl)oxy]benzaldehyde (3 g, 11.2 mmol) was dissolved in 100 mL of a 5M solution of ammonia in methanol and stirred overnight, after which the reaction mixture was treated with sodium borohydride (858 mg, 22.5 mmol) and stirred at room temperature for four days. The reaction was quenched by the addition of 20 mL of water and stirred for 30 minutes. The volatiles were removed and the residue was extracted with methylene chloride (3×20 mL). The methylene chloride was evaporated to give a yellow oil which was purified by preparative HPLC to provide the TFA salt of 1-{4-bromo-2-[(trifluoromethyl)oxy]phenyl}methanamine (900 mg, 3.3 mmol, 29%) as a white solid. MS (ES) m/e 270, 272 [M+H]+. 1H NMR (400 MHz, DMSO-D6) ☐ 8.5 (bs, 2H), 7.8 (d, 1H), 7.7 (s, 1H), 7.6 (d, 1H), 4.1 (bs, 2H)

Intermediate 21:
4-(aminomethyl)-3-(trifluoromethyl)benzonitrile

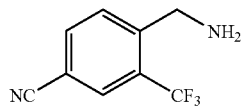

Step 1:
4-(bromomethyl)-3-(trifluoromethyl)benzonitrile

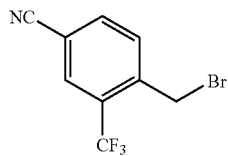

4-methyl-3-(trifluoromethyl)benzonitrile (10 g, 54 mmol) was dissolved in 200 mL of carbon tetrachloride and treated with N-bromosuccinimide (10.5 g, 59 mmol) and benzoyl peroxide (1.3 g, 0.54 mmol). The reaction mixture was heated to reflux temperature and stirred for one week. Then, 80 mL of water was added and the layers were separated. The aqueous layer was extracted with methylene chloride (2×50 mL). The combined organic layers were washed with water (2×50 mL), dried over magnesium sulfate, and concentrated to provide 4-(bromomethyl)-3-(trifluoromethyl)benzonitrile (14 g, 53 mmol) as a yellow oil which was used in the next step without further purification.

Step 2:
4-(aminomethyl)-3-(trifluoromethyl)benzonitrile

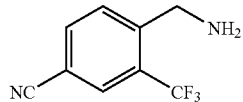

4-(bromomethyl)-3-(trifluoromethyl)benzonitrile (14 g) was dissolved in 500 mL of a solution of 5M ammonia in methanol and stirred for 24 hours at room temperature. The solvent was removed under vacuum to provide a yellow solid which was dissolved in 1M HCl and extracted with diethyl ether (3×30 mL). The aqueous layer was then adjusted to a pH of 9-10 with 1M NaOH and extracted with dichloromethane (3×80 mL). This provided 4-(aminomethyl)-3-(trifluoromethyl)benzonitrile (4.7 g, 23 mmol, 43%) as a yellow solid.

MS (ES) m/e 201 [M+H]+. 1H NMR (400 MHz, DMSO-D6) ☐ 8.2 (s, 1H), 8.15 (d, 1H), 8.0 (d, 1H), 3.9 (s, 2H)

Example 1 cis-4-{[4-(methylamino)-6-(3-pyridinyl)-1,3,5-triazin-2-yl]amino}-N-{[2-(trifluoromethyl)phenyl]methyl}cyclohexanecarboxamide

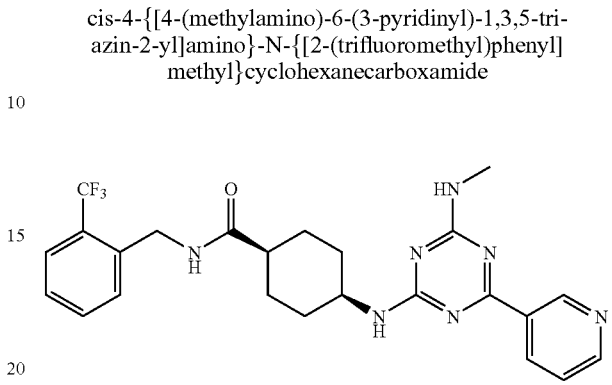

A microwave vial was charged with PdCl$_2$(dppf)$_2$ (27.7 mg, 0.0339 mmol, 0.2 equiv) and 3-pyridinylboronic acid (52.0 mg, 0.423 mmol, 2.5 equiv). A premixed solution of THF (2.1 mL) and Intermediate 13 (75 mg, 0.17 mmol, 1.0 equiv) was added, followed by 0.6 M aqueous potassium carbonate (2.8 mL, 1.7 mmol, 10 equiv). The reaction was heated via microwave reactor for 20 min at 150° C. The reaction was diluted with water (5 mL) and extracted three times with ethyl acetate (5 mL). The ethyl acetate extracts were combined, dried with Na$_2$SO$_4$, filtered, and concentrated under reduced pressure. The residue was purified via reverse-phase HPLC to afford 7.2 mg (8.8%) of the title compound. MS (ES+): m/e 486.1 [M+H]+.

Example 2 cis-4-{[4-(methylamino)-6-phenyl-1,3,5-triazin-2-yl]amino}-N-{[2-(trifluoromethyl)phenyl]methyl}cyclohexanecarboxamide A microwave vial was charged with palladium (II) acetate (0.38 mg, 0.0017 mmol, 0.01 equiv), tricyclohexylphosphine (0.95 mg, 0.0034 mmol, 0.02 equiv), and phenyl boronic acid (30.9 mg, 0.253 mmol, 1.5 equiv). A solution of 1,4-dioxane (0.86 mL) and Intermediate 1 (75 mg, 0.17 mmol, 1 equiv) was added, followed by a solution of water (0.13 mL) and potassium phosphate tribasic (71.7 mg, 0.338 mmol, 2 equiv). The reaction was heated via microwave reactor for 20 min at 150° C. The reaction was diluted with water (5 mL) and extracted three times with ethyl acetate (5 mL). The ethyl acetate extracts were combined, dried with Na$_2$SO$_4$, filtered, and concentrated under reduced pressure. The residue was purified via reverse-phase HPLC purification to afford 4.3 mg (5.3%) of the title compound. MS (ES+): m/e 485.1 [M+H]+.

Alternatively, Example 2 may be Prepared According to the Procedure Below

Example 2 cis-4-{[4-(methylamino)-6-phenyl-1,3,5-triazin-2-yl]amino}-N-{[2-(trifluoromethyl)phenyl]methyl}cyclohexanecarboxamide

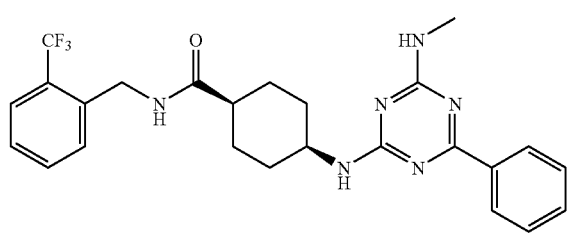

Step 1: 2,4-dichloro-6-phenyl-1,3,5-triazine

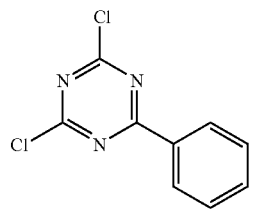

Phenylmagnesium bromide (97.6 ml of a 1.0 M solution in THF, 97.6 mmol, 1.0 equiv) was added dropwise to a THF (8 mL) solution of cyanuric chloride (18.0 g, 97.6 mmol, 1.0 equiv) at 0° C. The reaction mixture was stirred at room temperature for 1 h and was poured onto ice and stirred for 30 min. The product was extracted with ethyl acetate, and the combined organic layers were washed with (sat.) sodium chloride, dried (Na$_2$SO$_4$), filtered, and concentrated under reduced pressure to afford 16 g the title compound. The crude product was carried forward without purification.

Step 2: 4-chloro-N-methyl-6-phenyl-1,3,5-triazin-2-amine

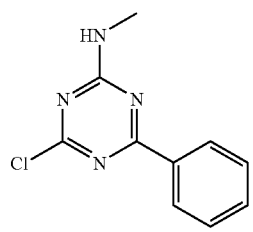

To a cooled (0° C.) solution of 2,4-dichloro-6-phenyl-1,3,5-triazine (16.0 g, 70.8 mmol, 1.00 equiv) dissolved in 1:1 CH$_3$CN:H$_2$O (80 mL) was added NH$_2$Me (8.00 g, 27.5% solution in H$_2$O, 70.8 mmol, 1.00 equiv). The solution was treated with 1 N NaOH to maintain a pH of 9-10 and stirred for 15 min. The resulting suspension was diluted with water and filtered to provide 12 g of crude product. A portion of this material (8 g) was purified by reverse-phase HPLC to afford 3.6 g of the title compound. MS (ES+): m/e 221.1 [M+H]+.

Step 3: cis-4-{[4-(methylamino)-6-phenyl-1,3,5-triazin-2-yl]amino}-N-{[2-(trifluoromethyl)phenyl]methyl}cyclohexanecarboxamide

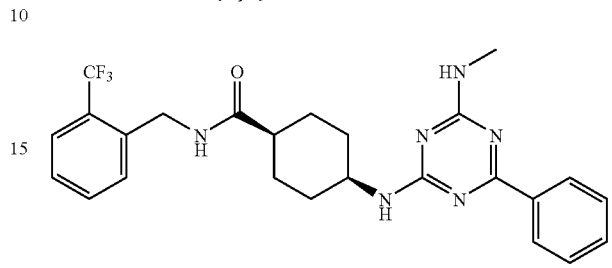

To a mixture of Intermediate 1 (2.04 g, 6.80 mmol) and diisopropylethylamine (3.55 mL, 20.4 mmol) in acetonitrile (100 mL) was added 4-chloro-N-methyl-6-phenyl-1,3,5-triazin-2-amine (1.5 g, 6.8 mmol). The mixture was heated at reflux temperature for 18 h. The solvent was evaporated, and the residue was dissolved in DMF, acidified with TFA, and purified by reverse-phase HPLC (Phenomenex, 90 mL/min, 20%-85% MeCN/water with 0.1% TFA, 20 min, UV detection at 214 nm) to afford the title compound (2.05 g, 99.7% purity, 50.2% yield) as the TFA salt. MS (ES+): m/e 485.1 [M+H]+. Impure HPLC fractions were combined and repurified via HPLC to obtain additional product (0.6 g, >99% purity, 14.8% yield). MS (ES+): m/e 485.1 [M+H]+.

Example 3 cis-4-{[4-(methylamino)-6-(3-thienyl)-1,3,5-triazin-2-yl]amino}-N-{[2-(trifluoromethyl)phenyl]methyl}cyclohexanecarboxamide

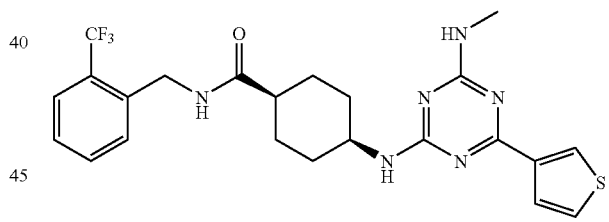

Example 3 was prepared using the general procedure described above in Example 2 substituting 3-thienylboronic acid for phenylboronic acid. MS (ES+): m/e 491.0 [M+H]+.

Example 4 cis-4-{[4-[4-(1,1-dimethylethyl)phenyl]-6-(methylamino)-1,3,5-triazin-2-yl]amino}-N-{[2-(trifluoromethyl)phenyl]methyl}cyclohexanecarboxamide

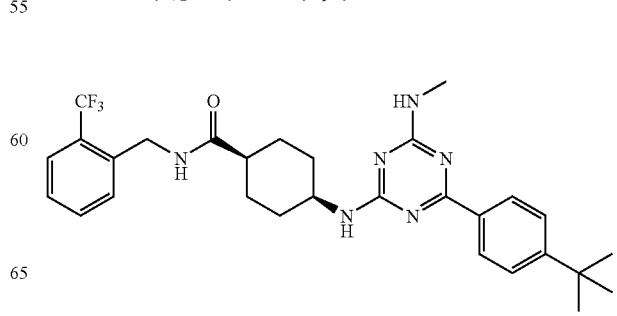

Example 4 was prepared using the general procedure described above in Example 2 substituting [4-(1,1-dimethylethyl)phenyl]boronic acid for phenylboronic acid. MS (ES+): m/e 541.1 [M+H]$^+$.

Example 5 cis-4-{[4-(2-fluorophenyl)-6-(methylamino)-1,3,5-triazin-2-yl]amino}-N-{[2-(trifluoromethyl)phenyl]methyl}cyclohexanecarboxamide

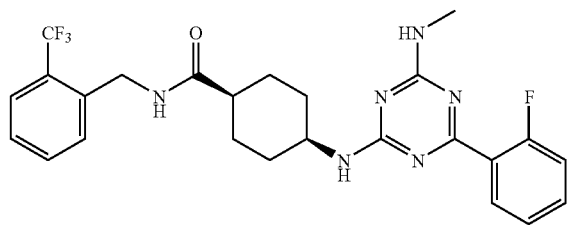

Example 5 was prepared using the general procedure described above in Example 2 substituting 2-fluorophenylboronic acid for phenylboronic acid. MS (ES+): m/e 503.0 [M+H]$^+$.

Example 6 cis-4-{[4-(4-cyanophenyl)-6-(methylamino)-1,3,5-triazin-2-yl]amino}-N-{[2-(trifluoromethyl)phenyl]methyl}cyclohexanecarboxamide

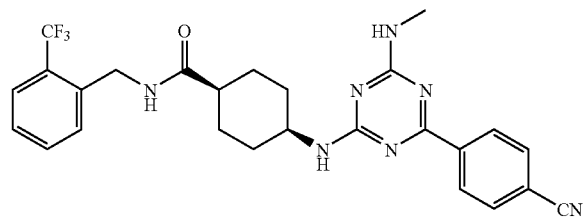

Example 6 was prepared using the general procedure described above in Example 2 substituting 4-cyanophenylboronic acid for phenylboronic acid. MS (ES+): m/e 510.0 [M+H]$^+$.

Example 7 cis-4-({4-(methylamino)-6-[4-(methylsulfonyl)phenyl]-1,3,5-triazin-2-yl}amino)-N-({2-[(trifluoromethyl)oxy]phenyl}methyl)cyclohexanecarboxamide

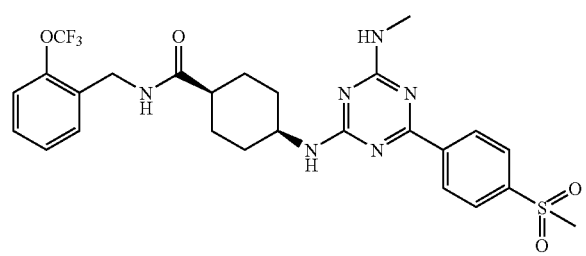

Example 7 was prepared using the general procedure described above in Example 2 substituting Intermediate 2 for Intermediate 1 and [4-(methylsulfonyl)phenyl]boronic acid for phenylboronic acid. MS (ES+): m/e 579.0 [M+H]$^+$.

Example 8 cis-4-{[4-(methylamino)-6-(3-pyridinyl)-1,3,5-triazin-2-yl]amino}-N-({2-[(trifluoromethyl)oxy]phenyl}methyl)cyclohexanecarboxamide

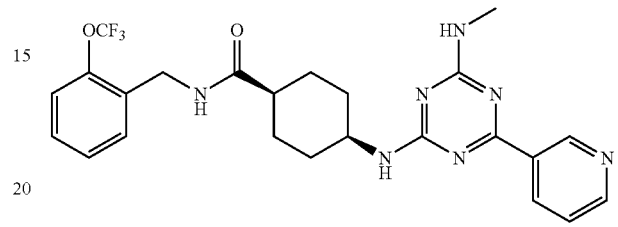

Example 8 was prepared using the general procedure described above in Example 1 substituting Intermediate 2 for Intermediate 1. MS (ES+): m/e 502.0 [M+H]$^+$.

Example 9 cis-4-({4-(methylamino)-6-[4-(trifluoromethyl)phenyl]-1,3,5-triazin-2-yl}amino)-N-({2-[(trifluoromethyl)oxy]phenyl}methyl)cyclohexanecarboxamide

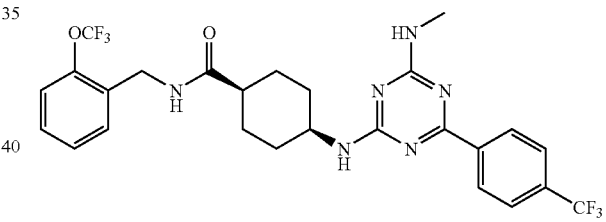

Example 9 was prepared using the general procedure described above in Example 2 substituting Intermediate 2 for Intermediate 1 and [4-(trifluoromethyl)phenyl]boronic acid for phenylboronic acid. MS (ES+): m/e 569.0 [M+H]$^+$.

Example 10

3-{4-(methylamino)-6-[(cis-4-{[({2-[(trifluoromethyl)oxy]phenyl}methyl)amino]carbonyl}cyclohexyl)amino]-1,3,5-triazin-2-yl}benzoic acid

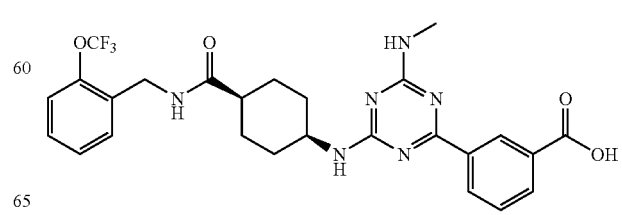

Example 10 was prepared using the general procedure described above in Example 2 substituting Intermediate 2 for Intermediate 1 and 3-(dihydroxyboranyl)benzoic acid for phenylboronic acid. MS (ES+): m/e 545.0 [M+H]+.

Example 11

3-[4-(methylamino)-6-({cis-4-[({[4-(methyloxy)-2-(trifluoromethyl)phenyl]methyl}amino)carbonyl]cyclohexyl}amino)-1,3,5-triazin-2-yl]benzoic acid

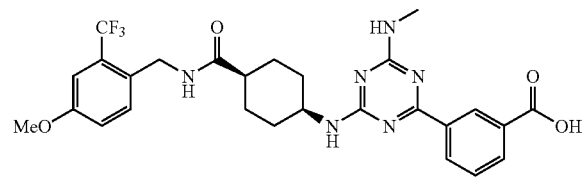

Example 11 was prepared using the general procedure described above in Example 2 substituting Intermediate 9 for Intermediate 1 and 3-(dihydroxyboranyl)benzoic acid for phenylboronic acid. MS (ES+): m/e 559.0 [M+H]+.

Example 12 cis-4-({4-(methylamino)-6-[4-(trifluoromethyl)phenyl]-1,3,5-triazin-2-yl}amino)-N-{[4-(methyloxy)-2-(trifluoromethyl)phenyl]methyl}cyclohexanecarboxamide

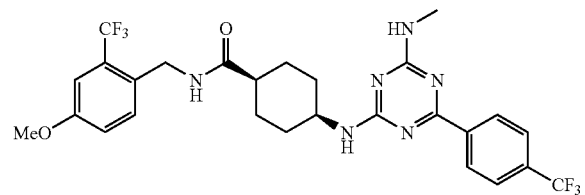

Example 12 was prepared using the general procedure described above in Example 2 substituting Intermediate 9 for Intermediate 1 and [4-(trifluoromethyl)phenyl]boronic acid for phenylboronic acid. MS (ES+): m/e 583.0 [M+H]+.

Example 13 cis-4-{[4-(methylamino)-6-(3-pyridinyl)-1,3,5-triazin-2-yl]amino}-N-{[4-(methyloxy)-2-(trifluoromethyl)phenyl]methyl}cyclohexanecarboxamide

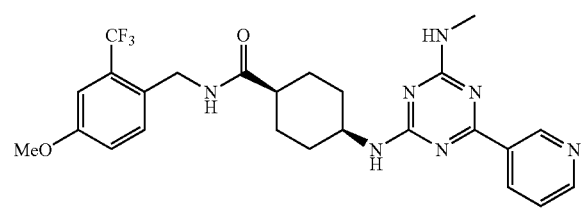

Example 13 was prepared using the general procedure described above in Example 1 substituting Intermediate 9 for Intermediate 1. MS (ES+): m/e 516.0 [M+H]+.

Example 14 cis-4-({4-(methylamino)-6-[4-(methylsulfonyl)phenyl]-1,3,5-triazin-2-yl}amino)-N-{[4-(methyloxy)-2-(trifluoromethyl)phenyl]methyl}cyclohexanecarboxamide

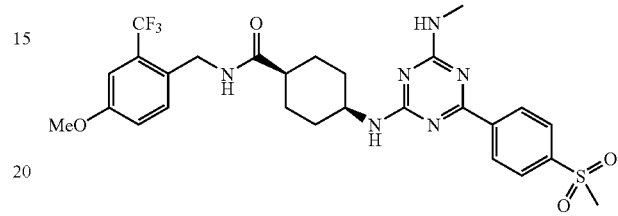

Example 12 was prepared using the general procedure described above in Example 2 substituting Intermediate 9 for Intermediate 1 and [4-(methylsulfonyl)phenyl]boronic acid for phenylboronic acid. MS (ES+): m/e 593.0 [M+H]+.

Example 15

3-[4-(methylamino)-6-({cis-4-[({[4-(trifluoromethyl)-3-pyridinyl]methyl}amino)carbonyl]cyclohexyl}amino)-1,3,5-triazin-2-yl]benzoic acid

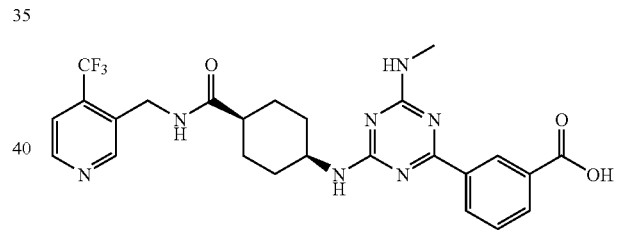

Example 15 was prepared using the general procedure described above in Example 2 substituting Intermediate 11 for Intermediate 1 and 3-(dihydroxyboranyl)benzoic acid for phenylboronic acid. MS (ES+): m/e 530.1 [M+H]+.

Example 16 cis-4-({4-(methylamino)-6-[4-(trifluoromethyl)phenyl]-1,3,5-triazin-2-yl}amino)-N-{[4-(trifluoromethyl)-3-pyridinyl]methyl}cyclohexanecarboxamide

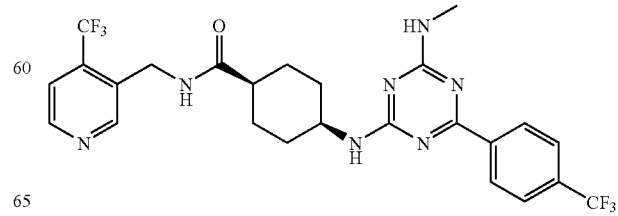

Example 16 was prepared using the general procedure described above in Example 2 substituting Intermediate 11 for Intermediate 1 and [4-(trifluoromethyl)phenyl]boronic acid for phenylboronic acid. MS (ES+): m/e 534.0 [M+H]$^+$.

Example 17 cis-4-{[4-(methylamino)-6-(3-pyridinyl)-1,3,5-triazin-2-yl]amino}-N-{[4-(trifluoromethyl)-3-pyridinyl]methyl}cyclohexanecarboxamide

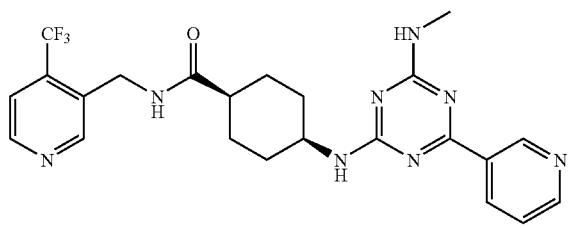

Example 13 was prepared using the general procedure described above in Example 1 substituting Intermediate 11 for Intermediate 1. MS (ES+): m/e 487.0 [M+H]$^+$.

Example 18 cis-4-({4-(methylamino)-6-[4-(methylsulfonyl)phenyl]-1,3,5-triazin-2-yl}amino)-N-{[4-(trifluoromethyl)-3-pyridinyl]methyl}cyclohexanecarboxamide

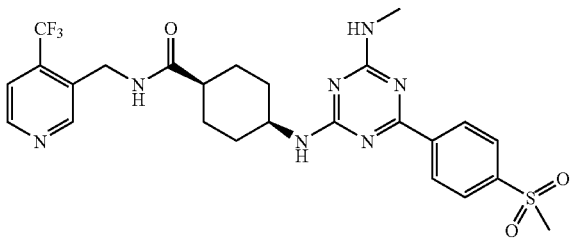

Example 18 was prepared using the general procedure described above in Example 2 substituting Intermediate 11 for Intermediate 1 and [4-(methylsulfonyl)phenyl]boronic acid for phenylboronic acid. MS (ES+): m/e 564.0 [M+H]$^+$.

Example 19

3-[4-{[cis-4-({[(2-chloro-4-cyanophenyl)methyl]amino}carbonyl)cyclohexyl]amino}-6-(methylamino)-1,3,5-triazin-2-yl]benzoic acid

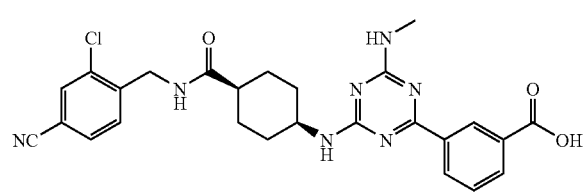

Example 19 was prepared using the general procedure described above in Example 2 substituting Intermediate 10 for Intermediate 1 and 3-(dihydroxyboranyl)benzoic acid for phenylboronic acid. MS (ES+): m/e 520.2 [M+H]$^+$.

Example 20 cis-N-[(2-chloro-4-cyanophenyl)methyl]-4-{[4-(methylamino)-6-(3-pyridinyl)-1,3,5-triazin-2-yl]amino}cyclohexanecarboxamide

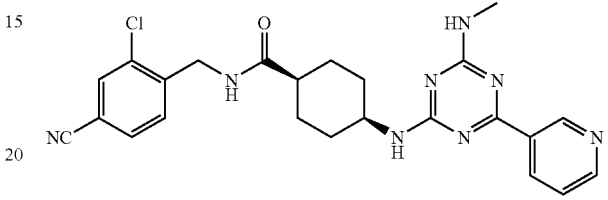

Example 20 was prepared using the general procedure described above in Example 1 substituting Intermediate 10 for Intermediate 1. MS (ES+): m/e 477.0 [M+H]$^+$.

Example 21 cis-4-({4[(2-hydroxyethyl)amino]-6-methyl-1,3,5-triazin-2-yl}amino)-N-{[2-(trifluoromethyl)phenyl]methyl}cyclohexanecarboxamide

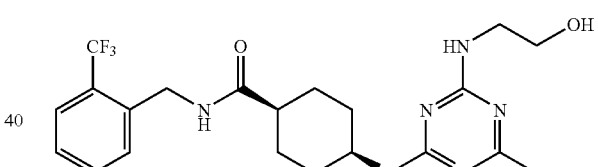

Step 1: cis-4-[(4-chloro-6-methyl-1,3,5-triazin-2-yl)amino]-N-{[2-(trifluoromethyl)phenyl]methyl}cyclohexanecarboxamide

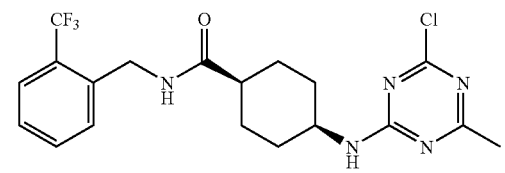

To a solution of cis-4-amino-N-{[2-(trifluoromethyl)phenyl]methyl}cyclohexanecarboxamide (90 mg, 0.30 mmol, 1.0 equiv) in acetonitrile (12 ml) at room temperature, Intermediate 13 (49 mg, 0.30 mmol, 1.0 equiv) and diisopropylethylamine (DIEA, 35 mgs, 0.30 mmol, 1.0 equiv) were added. The reaction was stirred for 3 h at room temperature. The solvent was removed under reduced pressure, and the residue was purified on silica gel using 25% ethyl acetate/ petroleum ether to afford 100 mgs of a yellow solid (78% yield). MS (ES+): m/e 428.1 [M+H]+.

Step 2: cis-4-({4-[(2-hydroxyethyl)amino]-6-methyl-1,3,5-triazin-2-yl}amino)-N-{[2-(trifluoromethyl)phenyl]methyl}cyclohexanecarboxamide

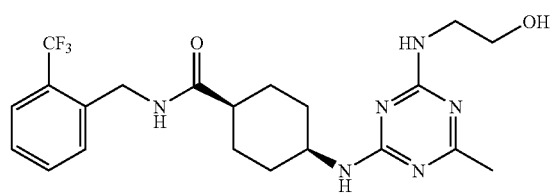

A mixture of cis-4-[(4-chloro-6-methyl-1,3,5-triazin-2-yl)amino]-N-{[2-(trifluoromethyl)phenyl]methyl}cyclohexanecarboxamide (70 mgs, 0.16 mmol, 1.0 equiv), 2-aminoethanol (15 mgs, 0.25 mmol, 1.5 equiv), and potassium carbonate (34 mgs, 0.25 mmol, 1.0 equiv) in acetonitrile (3 ml) was heated to reflux for 16 h. The solvent was removed under reduced pressure, and the residue was extracted with CH$_2$Cl$_2$ and washed with water. The organic layer was dried over sodium sulfate and concentrated. The residue was purified via reverse-phase HPLC purification to afford the title compound. MS (ES+): m/e 453.3 [M+H]+.

Example 22 cis-4-{[4-methyl-6-(4-methyl-1-piperazinyl)-1,3,5-triazin-2-yl]amino}-N-{[2-(trifluoromethyl)phenyl]methyl}cyclohexanecarboxamide

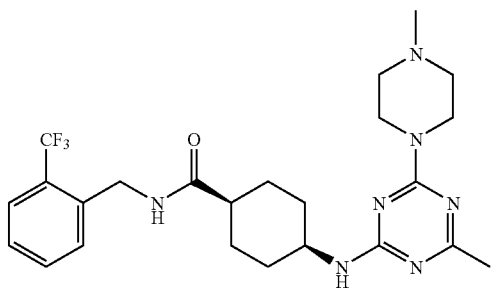

Example 22 was prepared using the general procedure described above in Example 21 substituting N-methylpiperazine for 2-aminoethanol in Step 2. MS (ES+): m/e 492.4 [M+H]+.

Example 23 cis-4-({4-methyl-6-[(phenylmethyl)amino]-1,3,5-triazin-2-yl}amino)-N-{[2-(trifluoromethyl)phenyl]methyl}cyclohexanecarboxamide

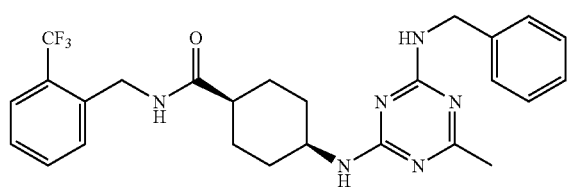

Example 23 was prepared using the general procedure described above in Example 21 substituting benzylamine for 2-aminoethanol in Step 2. MS (ES+): m/e 499.3 [M+H]+.

Example 24 cis-4-[(4-methyl-6-{[2-(methyloxy)ethyl]amino}-1,3,5-triazin-2-yl)amino]-N-{[2-(trifluoromethyl)phenyl]methyl}cyclohexanecarboxamide

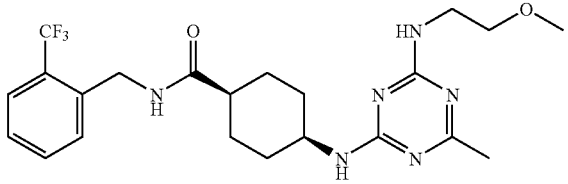

Example 24 was prepared using the general procedure described above in Example 21 substituting 2-(methyloxy)ethanamine for 2-aminoethanol in Step 2. MS (ES+): m/e 467.3 [M+H]+.

Example 25 cis-4-{[4-(dimethylamino)-6-methyl-1,3,5-triazin-2-yl]amino}-N-{[2-(trifluoromethyl)phenyl]methyl}cyclohexanecarboxamide

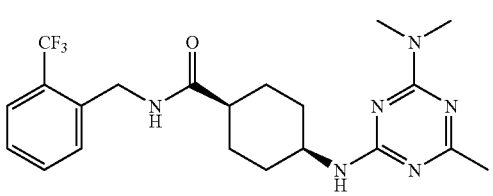

Example 25 was prepared using the general procedure described above in Example 21 substituting dimethylamine for 2-aminoethanol in Step 2. MS (ES+): m/e 437.3 [M+H]+.

Example 26 cis-4-{[4-methyl-6-(1-piperidinyl)-1,3,5-triazin-2-yl]amino}-N-{[2-(trifluoromethyl)phenyl]methyl}cyclohexanecarboxamide

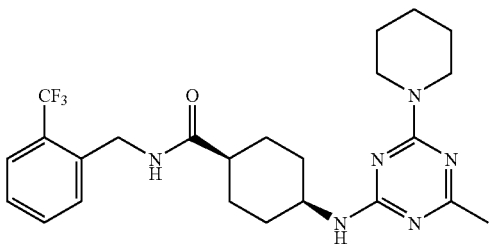

Example 26 was prepared using the general procedure described above in Example 21 substituting piperidine for 2-aminoethanol in Step 2. MS (ES+): m/e 477.3 [M+H]⁺.

Example 27 cis-4-[(4-amino-6-methyl-1,3,5-triazin-2-yl)amino]-N-{[2-(trifluoromethyl)phenyl]methyl}cyclohexanecarboxamide

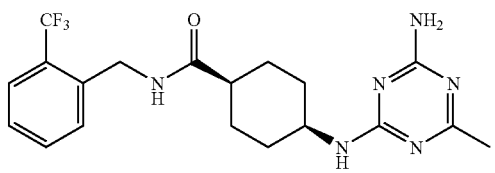

Example 27 was prepared using the general procedure described above in Example 21 substituting ammonia for 2-aminoethanol in step 2. MS (ES+): m/e 409.3 [M+H]⁺.

Example 28

N-[(2,4-dichlorophenyl)methyl]-3-{[4-methyl-6-(methylamino)-1,3,5-triazin-2-yl]amino}cyclohexanecarboxamide

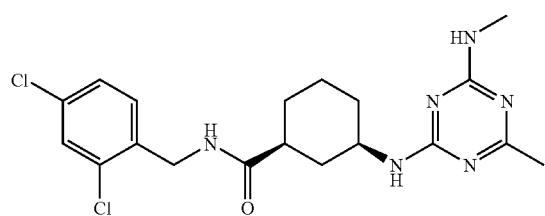

Step 1: 4-chloro-N-6-dimethyl-1,3,5-triazin-2-amine

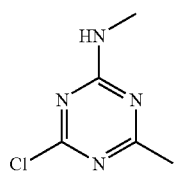

To a solution of Intermediate 13 (500 mg, 3.07 mmol) in CH₃CN/H₂O (15 mL) was added a solution of 25-30% methylamine (300 uL, 3.07 mmol) in water. The mixture was cooled to 0° C., and the pH was adjusted to 9-10 with 1 M NaOH. The pH was maintained at 9-10 for 0.5 h. The reaction progress was monitored by LCMS, and the mixture was used in the next step without workup.

Step 2: 3-{[4-methyl-6-(methylamino)-1,3,5-triazin-2-yl]amino}cyclohexanecarboxylic acid

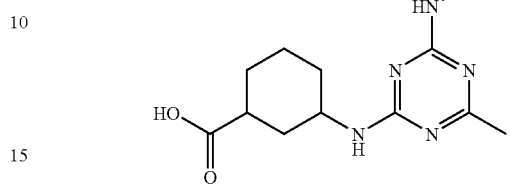

To a mixture of 4-chloro-N-6-dimethyl-1,3,5-triazin-2-amine (485 mg, 3.07 mmol) was added 3-aminocyclohexanecarboxylic acid (527 mg, 3.68 mmol) at 0° C. The mixture was allowed to warm to rt. The pH was maintained between 9 and 10 for 3 h. The mixture was concentrated and the product was purified by HPLC to afford 0.6 g (2.26 mmol, 74% yield) of the desired product as a white solid. MS (ES+): m/e 266.2 [M+H]⁺.

Step 3: cis-N-[(2,4-dichlorophenyl)methyl]-3-{[4-methyl-6-(methylamino)-1,3,5-triazin-2-yl]amino}cyclohexanecarboxamide

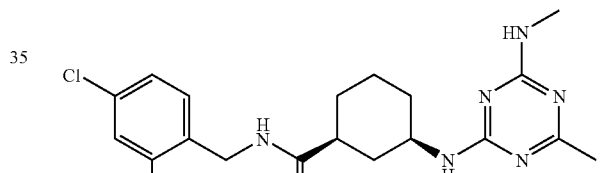

To a solution of 3-{[4-methyl-6-(methylamino)-1,3,5-triazin-2-yl]amino}cyclohexanecarboxylic acid (100 mg, 0.377 mmol) was added [(2,4-dichlorophenyl)methyl]amine (82 mg, 0.47 mmol), DMAP (10 mg, 0.08 mmol) and EDCl (108 mg, 0.56 mmol). The mixture was stirred at room temperature for 4 h. The mixture was filtered and the filtrate concentrated. The crude product was purified by HPLC to provide 55 mg (0.13 mmol, 35% yield) of the desired material as a single major racemic diastereomer. MS (ES+): m/e 423.0 [M+H]⁺.

Alternatively Example 28 can be Prepared by the Following Method

Step 1: 3-({[(1,1-dimethylethyl)oxy]carbonyl}amino)cyclohexanecarboxylic acid

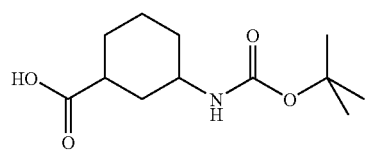

To a suspension of 3-aminocyclohexanecarboxylic acid (10 g, 69.8 mmol) in 1,4-Dioxane (100.0 mL) was added 1N NaOH (41.9 ml, 105 mmol). After stirring for 10 minutes, the mixture turned to a clear solution and bis(1,1-dimethylethyl) dicarbonate (21.08 ml, 91 mmol) was added to the reaction. The reaction was stirred at room temperature overnight. The resulting solids were vacuum filtered and then redissolved in water (150 mL). The aqueous material was made acidic (pH 4) with 3N HCl, and then extracted (2×100 mL) with DCM. The organics were dried over $Na_2SO_4$ and evacuated to yield the title compound as a white powder (17.0 g, 100%).

Step 2: 3-amino-N-[(2,4-dichlorophenyl)methyl] cyclohexanecarboxamide

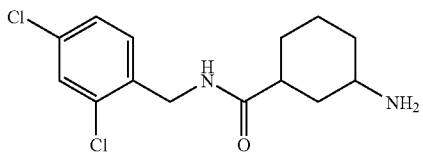

To a solution of 3-({[(1,1-dimethylethyl)oxy] carbonyl}amino)cyclohexanecarboxylic acid (10.0 g, 41.1 mmol) in DMF (200 mL) was added DIEA (10.77 mL, 61.7 mmol), followed by 2,4-dichlorobenzylamine (5.53 mL, 41.1 mmol) and BOP (18.18 g, 41.1 mmol). The reaction was stirred overnight at room temperature. Saturated $NaHCO_3$ (300 mL) was added to the reaction which affected a white precipitate to form after 10 minutes. The precipitate was vacuum filtered, washed with water, and dried. The solids were suspended in DCM (50 mL) and treated with TFA (10 mL). After stirring for 2 hours, the reaction was cooled to 0° C., basified with 6N NaOH to pH 10, and then extracted with DCM (3×100 mL). The organics were dried ($Na_2SO_4$) and evacuated to afford Intermediate 14 (6.2 g, 50%) as a white solid. MS (ES+): m/e 301.0 [M]$^+$.

Step 3: cis-N-[(2,4-dichlorophenyl)methyl]-3-{[4-methyl-6-(methylamino)-1,3,5-triazin-2-yl] amino}cyclohexanecarboxamide

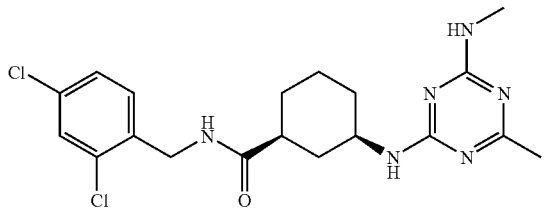

To a mixture of 3-amino-N-[(2,4-dichlorophenyl)methyl] cyclohexanecarboxamide (5.00 g, 16.60 mmol) in Tetrahydrofuran (THF) (207 mL) was added Intermediate 13 (2.72 g, 16.60 mmol). DIEA (3.62 ml, 20.75 mmol) was then added dropwise. The reaction was stirred at room temperature for 30 minutes, at which point LCMS showed the desired intermediate. Next, methylamine (41.5 ml, 83 mmol) was added to the reaction, which was heated to 45° C. and stirred overnight. LCMS showed conversion to the desired product. The reaction was evacuated and then granulated in acetonitrile (100 mL). The solids were filtered and dried to afford the freebase as a white solid. The solids were dissolved in DMSO and TFA and subjected to reverse-phase HPLC purification to afford the title compound (2.0 g, 22%) as a white solid. The relative stereochemistry of the major isomer was determined to be cis by 2D NMR. MS (ES+): m/e 423.0 [M+H]$^+$.

Example 29 cis-3-{[4-methyl-6-(methylamino)-1,3,5-triazin-2-yl] amino}-N-{[2-(trifluoromethyl)phenyl] methyl}cyclohexanecarboxamide

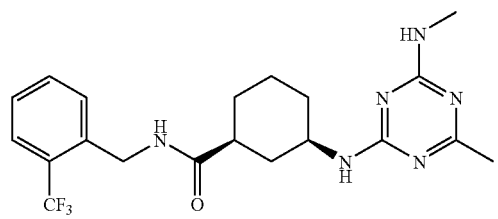

Example 29 was prepared using the general procedure described above in Example 28 substituting 1-[2-(trifluoromethyl)phenyl]methanamine for [(2,4-dichlorophenyl)methyl] amine in Step 3. MS (ES+): m/e 423.1 [M+H]$^+$.

Example 30 cis-3-{[4-methyl-6-(methylamino)-1,3,5-triazin-2-yl] amino}-N-({2-[(trifluoromethyl)oxy]phenyl}methyl) cyclohexanecarboxamide

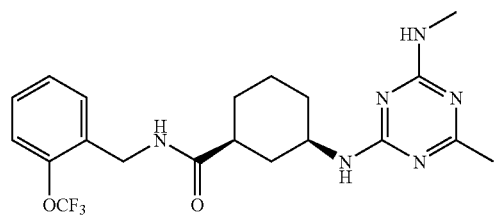

Example 30 was prepared using the general procedure described above in Example 28 substituting 1-{2-[(trifluoromethyl)oxy]phenyl}methanamine for [(2,4-dichlorophenyl)methyl]amine in Step 3. MS (ES+): m/e 439.1 [M+H]$^+$.

Example 31 cis-N-{[4-chloro-2-(trifluoromethyl)phenyl]methyl}-3-{[4-methyl-6-(methylamino)-1,3,5-triazin-2-yl] amino}cyclohexanecarboxamide

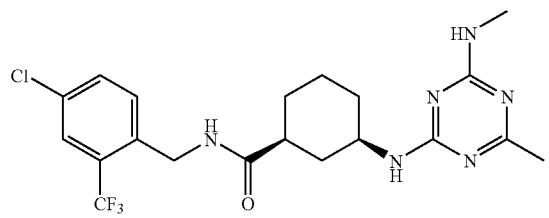

Example 31 was prepared using the general procedure described above in Example 28 substituting 1-[4-chloro-2-(trifluoromethyl)phenyl]methanamine for [(2,4-dichlorophenyl)methyl]amine in Step 3. MS (ES+): m/e 457.3 [M+H]+.

Example 32

(cis)-N-({2-chloro-4-[(methylsulfonyl)amino]phenyl}methyl)-3-{[4-methyl-6-(methylamino)-1,3,5-triazin-2-yl]amino}cyclohexanecarboxamide

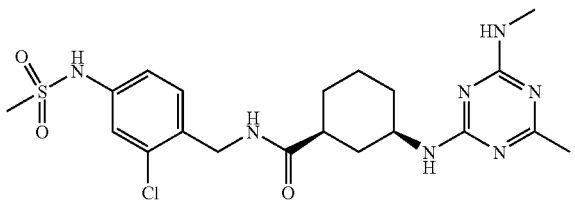

Example 32 was prepared using the general procedure described above in Example 28 substituting Intermediate 3 for [(2,4-dichlorophenyl)methyl]amine in Step 3. MS (ES+): m/e 482.0 [M+H]+.

Example 33

(cis)-N-{[2-chloro-4-(dimethylamino)phenyl]methyl}-3-{[4-methyl-6-(methylamino)-1,3,5-triazin-2-yl]amino}cyclohexanecarboxamide

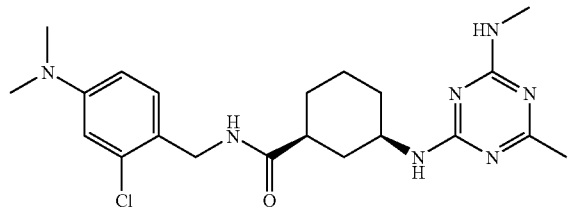

Example 33 was prepared using the general procedure described above in Example 28 substituting Intermediate 4 for [(2,4-dichlorophenyl)methyl]amine in Step 3. MS (ES+): m/e 432.0 [M+H]+.

Example 34

(cis)-N-[(2-chloro-4-cyanophenyl)methyl]-3-{[4-methyl-6-(methylamino)-1,3,5-triazin-2-yl]amino}cyclohexanecarboxamide

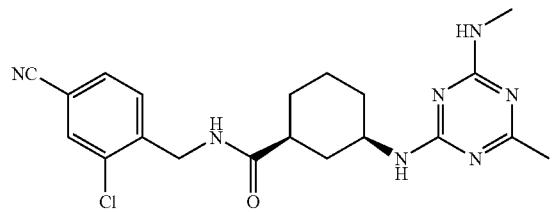

Example 34 was prepared using the general procedure described above in Example 28 substituting Intermediate 6 for [(2,4-dichlorophenyl)methyl]amine in Step 3. MS (ES+): m/e 366.0 [M+H]+.

Example 35

(cis)-N-{[2-chloro-4-(1H-tetrazol-5-yl)phenyl]methyl}-3-{[4-methyl-6-(methylamino)-1,3,5-triazin-2-yl]amino}cyclohexanecarboxamide

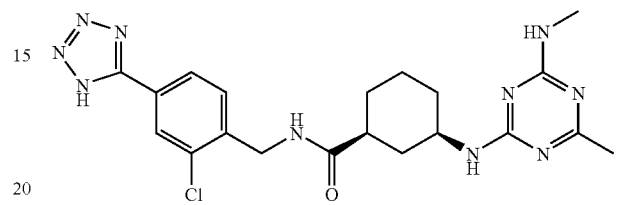

Example 35 was prepared using the general procedure described above in Example 28 substituting Intermediate 14 for [(2,4-dichlorophenyl)methyl]amine in Step 3. MS (ES+): m/e 457.1 [M+H]+.

Example 36

(cis)-3-{[4-methyl-6-(methylamino)-1,3,5-triazin-2-yl]amino}-N-{[3-(trifluoromethyl)-4-pyridinyl]methyl}cyclohexanecarboxamide

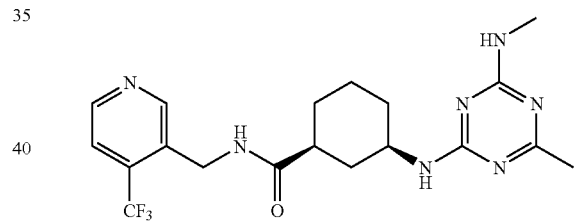

Example 36 was prepared using the general procedure described above in Example 28 substituting Intermediate 7 for [(2,4-dichlorophenyl)methyl]amine in Step 3. MS (ES+): m/e 424.0 [M+H]+.

Example 37

(cis)-3-{[4-(2-fluorophenyl)-6-(methylamino)-1,3,5-triazin-2-yl]amino}-N-{[2-(trifluoromethyl)phenyl]methyl}cyclohexanecarboxamide

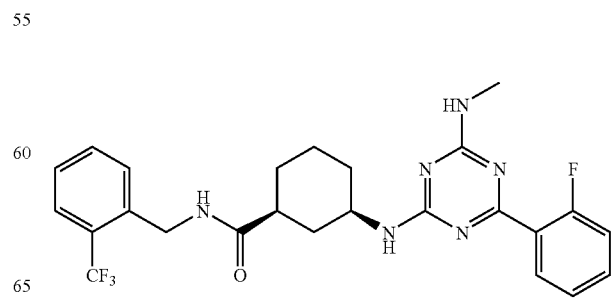

Example 37 was prepared using the general procedure described above in Example 2 substituting Intermediate 15 for Intermediate 1 and 2-fluorophenylboronic acid for phenylboronic acid. MS (ES+): m/e 503.0 [M+H]+.

Example 38

(cis)-3-{[4-(4-fluorophenyl)-6-(methylamino)-1,3,5-triazin-2-yl]amino}-N-{[2-(trifluoromethyl)phenyl]methyl}cyclohexanecarboxamide

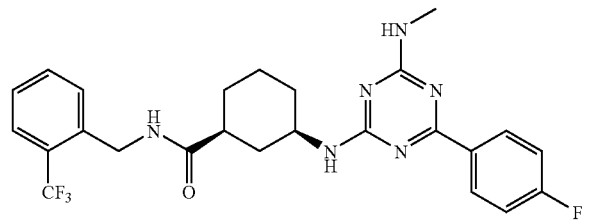

Example 38 was prepared using the general procedure described above in Example 2 substituting Intermediate 15 for Intermediate 1 and 4-fluorophenylboronic acid for phenylboronic acid. MS (ES+): m/e 503.0 [M+H]+.

Example 39

(cis)-3-{[4-(4-cyanophenyl)-6-(methylamino)-1,3,5-triazin-2-yl]amino}-N-{[2-(trifluoromethyl)phenyl]methyl}cyclohexanecarboxamide

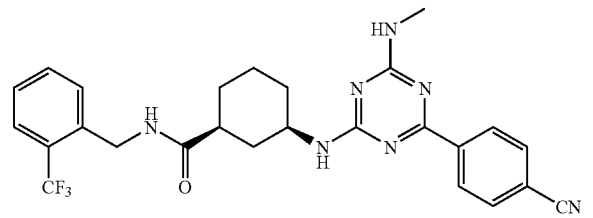

Example 39 was prepared using the general procedure described above in Example 2 substituting Intermediate 15 for Intermediate 1 and 4-cyanophenylboronic acid for phenylboronic acid. MS (ES+): m/e 510.0 [M+H]+.

Example 40

(cis)-4-{[4-methyl-6-(methylamino)-1,3,5-triazin-2-yl]amino}-N-{[2-(trifluoromethyl)phenyl]methyl}cyclohexanecarboxamide

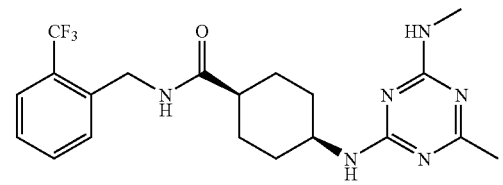

Example 40 was prepared using the general procedure described above in Example 28 substituting cis-4-aminocyclohexanecarboxylic acid for 3-aminocyclohexanecarboxylic acid in Step 2 and 1-[2-(trifluoromethyl)phenyl]methanamine for [(2,4-dichlorophenyl)methyl]amine in Step 3. MS (ES+): m/e 423.1 [M+H]+.

Example 41 cis-4-{[4-methyl-6-(methylamino)-1,3,5-triazin-2-yl]amino}-N-({2-[(trifluoromethyl)oxy]phenyl}methyl)cyclohexanecarboxamide

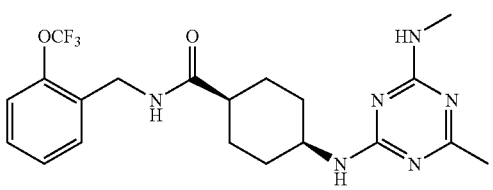

Example 41 was prepared using the general procedure described above in Example 28 substituting cis-4-aminocyclohexanecarboxylic acid for 3-aminocyclohexanecarboxylic acid in Step 2 and 1-{2-[(trifluoromethyl)oxy]phenyl}methanamine for [(2,4-dichlorophenyl)methyl]amine in Step 3. MS (ES+): m/e 439.1 [M+H]+.

Example 42 cis-N-[(2,4-dichlorophenyl)methyl]-4-{[4-methyl-6-(methylamino)-1,3,5-triazin-2-yl]amino}cyclohexanecarboxamide

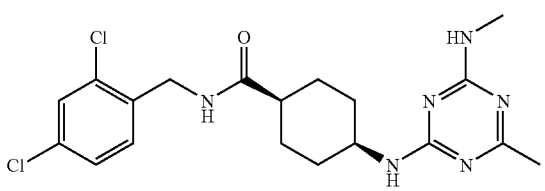

Example 42 was prepared using the general procedure described above in Example 28 substituting cis-4-aminocyclohexanecarboxylic acid for 3-aminocyclohexanecarboxylic acid in Step 2. MS (ES+): m/e 423.0 [M+H]+.

Example 43 cis-N-{[4-chloro-2-(trifluoromethyl)phenyl]methyl}-4-{[4-methyl-6-(methylamino)-1,3,5-triazin-2-yl]amino}cyclohexanecarboxamide

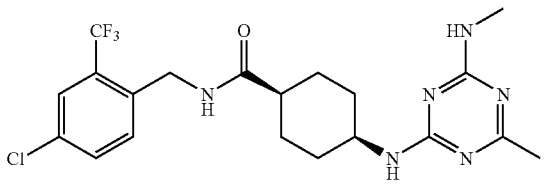

Example 43 was prepared using the general procedure described above in Example 28 substituting cis-4-aminocyclohexanecarboxylic acid for 3-aminocyclohexanecarboxylic acid in Step 2 and 1-[4-chloro-2-(trifluoromethyl)phenyl]methanamine for [(2,4-dichlorophenyl)methyl]amine in Step 3. MS (ES+): m/e 457.3 [M+H]⁺.

Example 44 cis-4-{[4-methyl-6-(methylamino)-1,3,5-triazin-2-yl]amino}-N-({2-[(trifluoromethyl)thio]phenyl}methyl)cyclohexanecarboxamide

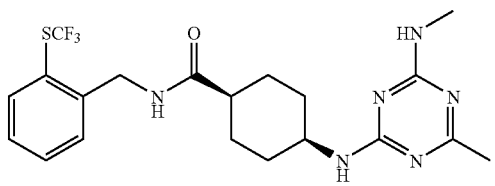

Example 44 was prepared using the general procedure described above in Example 28 substituting cis-4-aminocyclohexanecarboxylic acid for 3-aminocyclohexanecarboxylic acid in Step 2 and 1-{2-[(trifluoromethyl)thio]phenyl}methanamine for [(2,4-dichlorophenyl)methyl]amine in Step 3. MS (ES+): m/e 455.0 [M+H]⁺.

Example 45 trans-4-{[4-methyl-6-(methylamino)-1,3,5-triazin-2-yl]amino}-N-{[2-(trifluoromethyl)phenyl]methyl}cyclohexanecarboxamide

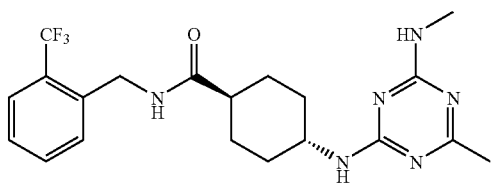

Example 44 was prepared using the general procedure described above in Example 28 substituting trans-4-aminocyclohexanecarboxylic acid for 3-aminocyclohexanecarboxylic acid in Step 2 and 1-[2-(trifluoromethyl)phenyl]methanamine for [(2,4-dichlorophenyl)methyl]amine in Step 3. MS (ES+): m/e 423.1 [M+H]⁺.

Example 46 trans-4-{[4-methyl-6-(methylamino)-1,3,5-triazin-2-yl]amino}-N-({2-[(trifluoromethyl)oxy]phenyl}methyl)cyclohexanecarboxamide

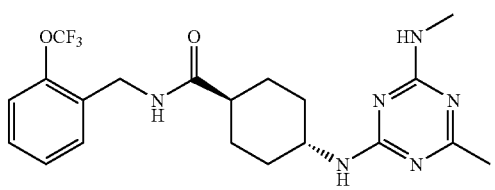

Example 46 was prepared using the general procedure described above in Example 28 substituting trans-4-aminocyclohexanecarboxylic acid for 3-aminocyclohexanecarboxylic acid in Step 2 and 1-{2-[(trifluoromethyl)oxy]phenyl}methanamine for [(2,4-dichlorophenyl)methyl]amine in Step 3. MS (ES+): m/e 439.1 [M+H]⁺.

Example 47 trans-N-[(2,4-dichlorophenyl)methyl]-4-{[4-methyl-6-(methylamino)-1,3,5-triazin-2-yl]amino}cyclohexanecarboxamide

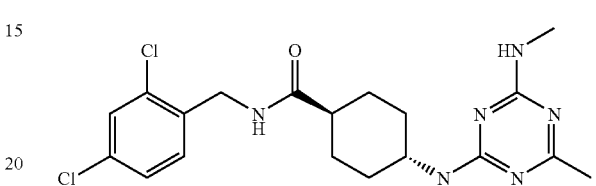

Example 47 was prepared using the general procedure described above in Example 28 substituting trans-4-aminocyclohexanecarboxylic acid for 3-aminocyclohexanecarboxylic acid in Step 2. MS (ES+): m/e 423.0 [M+H]⁺.

Example 48 trans-N-{[4-chloro-2-(trifluoromethyl)phenyl]methyl}-4-{[4-methyl-6-(methylamino)-1,3,5-triazin-2-yl]amino}cyclohexanecarboxamide

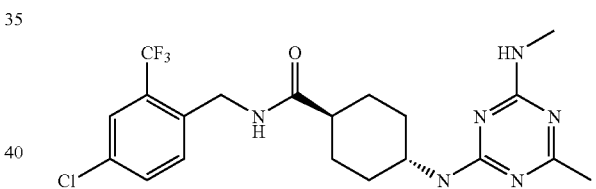

Example 48 was prepared using the general procedure described above in Example 12 substituting trans-4-aminocyclohexanecarboxylic acid for 3-aminocyclohexanecarboxylic acid in Step 2 and 1-[4-chloro-2-(trifluoromethyl)phenyl]methanamine for [(2,4-dichlorophenyl)methyl]amine in Step 3. MS (ES+): m/e 457.3 [M+H]⁺.

Example 49 cis-4-{methyl[4-methyl-6-(methylamino)-1,3,5-triazin-2-yl]amino}-N-{[2-(trifluoromethyl)phenyl]methyl}cyclohexanecarboxamide

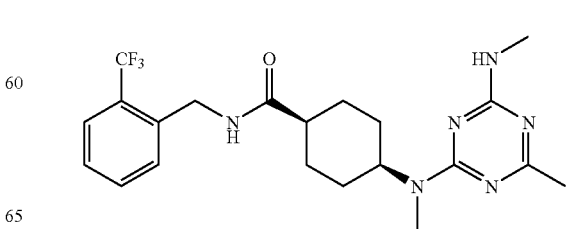

Example 49 was prepared using the general procedure described above in Example 28 substituting Intermediate 16 for 3-aminocyclohexanecarboxylic acid in Step 2 and 1-[2-(trifluoromethyl)phenyl]methanamine for [(2,4-dichlorophenyl)methyl]amine in Step 3. MS (ES+): m/e 437.1 [M+H]⁺.

Example 50 cis-4-{methyl[4-methyl-6-(methylamino)-1,3,5-triazin-2-yl]amino}-N-({2-[(trifluoromethyl)oxy]phenyl}methyl)cyclohexanecarboxamide

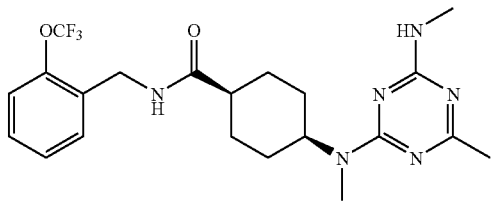

Example 50 was prepared using the general procedure described above in Example 28 substituting Intermediate 16 for 3-aminocyclohexanecarboxylic acid in Step 2 and 1-{2-[(trifluoromethyl)oxy]phenyl}methanamine for [(2,4-dichlorophenyl)methyl]amine in Step 3. MS (ES+): m/e 453.1 [M+H]⁺.

Example 51 cis-N-[(2,4-dichlorophenyl)methyl]-4-{methyl[4-methyl-6-(methylamino)-1,3,5-triazin-2-yl]amino}cyclohexanecarboxamide

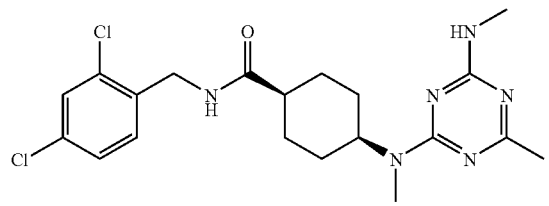

Example 51 was prepared using the general procedure described above in Example 28 substituting Intermediate 16 for 3-aminocyclohexanecarboxylic acid in Step 2. MS (ES+): m/e 437.0 [M+H]⁺.

Example 52 cis-N-{[4-chloro-2-(trifluoromethyl)phenyl]methyl}-4-{methyl[4-methyl-6-(methylamino)-1,3,5-triazin-2-yl]amino}cyclohexanecarboxamide

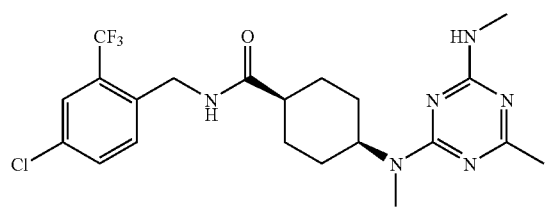

Example 52 was prepared using the general procedure described above in Example 28 substituting Intermediate 16 for 3-aminocyclohexanecarboxylic acid in Step 2 and 1-[4-chloro-2-(trifluoromethyl)phenyl]methanamine for [(2,4-dichlorophenyl)methyl]amine in Step 3. MS (ES+): m/e 471.0 [M+H]⁺.

Example 53 trans-4-{[4-(methylamino)-6-phenyl-1,3,5-triazin-2-yl]amino}-N-{[2-(trifluoromethyl)phenyl]methyl}cyclohexanecarboxamide

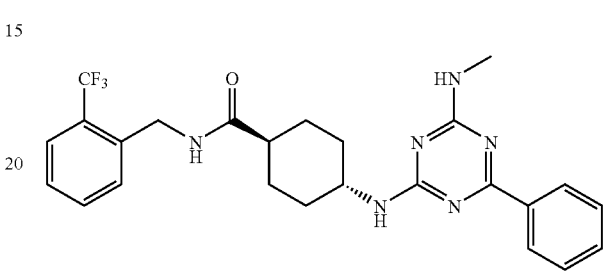

Step 1: trans-4-{[4-(methylamino)-6-phenyl-1,3,5-triazin-2-yl]amino}cyclohexanecarboxylic acid

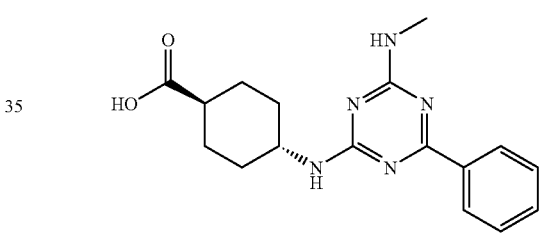

To a mixture of 4-chloro-N-methyl-6-phenyl-1,3,5-triazin-2-amine (1.0 g, 4.5 mmol) in $CH_3CN:H_2O$ (1:1, 5 mL) was added trans-4-aminocyclohexanecarboxylic acid (973 mgs, 6.80 mmol). The solution was treated with 1 N NaOH to maintain a pH of 9-10 and stirred at 80° C. for 36 h. The resulting mixture was diluted with water and filtered to provide the crude product, which was purified by HPLC to afford 300 mg (20% yield) of the desired product. MS (ES+): m/e 328.2 [M+H]⁺.

Step 2: trans-4-{[4-(methylamino)-6-phenyl-1,3,5-triazin-2-yl]amino}-N-{[2-(trifluoromethyl)phenyl]methyl}cyclohexanecarboxamide

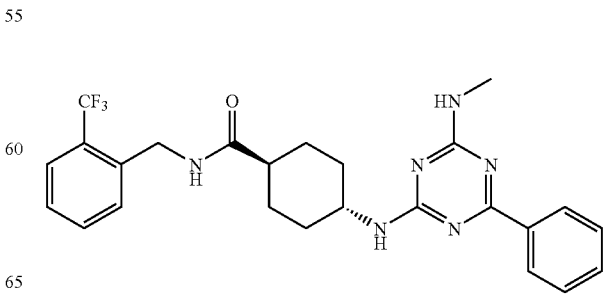

To a solution of trans-4-{[4-(methylamino)-6-phenyl-1,3,5-triazin-2-yl]amino}cyclohexanecarboxylic acid (40 mg, 0.12 mmol) was added 1-[2-(trifluoromethyl)phenyl]methanamine (22 mg, 0.12 mmol), EDCl (24 mg, 0.12 mmol), HOBt (17 mgs, 0.12 mmol), and N-methylmorpholine (13 mg, 0.12 mmol). The mixture was stirred at rt for 20 h. The solvent was removed under vacuum, and the resulting residue was purified by HPLC to provide 20 mg (34% yield) of the desired material. MS (ES+): m/e 485.3 [M+H]+.

Example 54 trans-4-{[4-(methylamino)-6-phenyl-1,3,5-triazin-2-yl]amino}-N-({2-[(trifluoromethyl)oxy]phenyl}methyl)cyclohexanecarboxamide

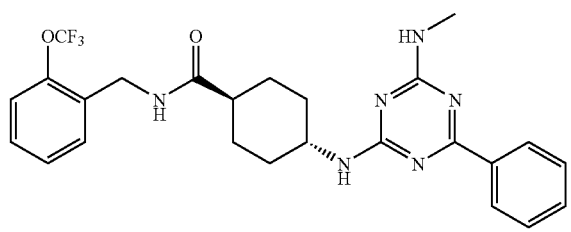

Example 54 was prepared using the general procedure described above in Example 53 substituting 1-{2-[(trifluoromethyl)oxy]phenyl}methanamine for 1-[2-(trifluoromethyl)phenyl]methanamine in Step 2. MS (ES+): m/e 501.1 [M+H]+.

Example 55 trans-N-[(2,4-dichlorophenyl)methyl]-4-{[4-(methylamino)-6-phenyl-1,3,5-triazin-2-yl]amino}cyclohexanecarboxamide

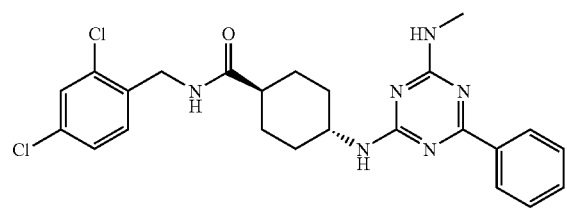

Example 55 was prepared using the general procedure described above in Example 53 substituting [(2,4-dichlorophenyl)methyl]amine for 1-[2-(trifluoromethyl)phenyl]methanamine in Step 2. MS (ES+): m/e 485.2 [M+H]+.

Example 56 trans-N-{[4-chloro-2-(trifluoromethyl)phenyl]methyl}-4-{[4-(methylamino)-6-phenyl-1,3,5-triazin-2-yl]amino}cyclohexanecarboxamide

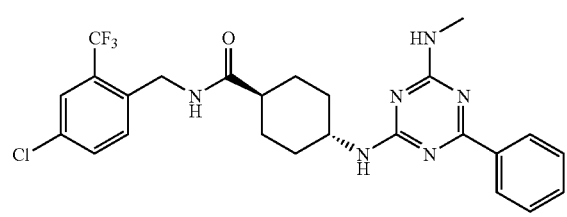

Example 56 was prepared using the general procedure described above in Example 53 substituting 1-[4-chloro-2-(trifluoromethyl)phenyl]methanamine for 1-[2-(trifluoromethyl)phenyl]methanamine in Step 2. MS (ES+): m/e 519.3 [M+H]+.

Example 57 cis-4-{methyl[4-(methylamino)-6-phenyl-1,3,5-triazin-2-yl]amino}-N-{[2-(trifluoromethyl)phenyl]methyl}cyclohexanecarboxamide

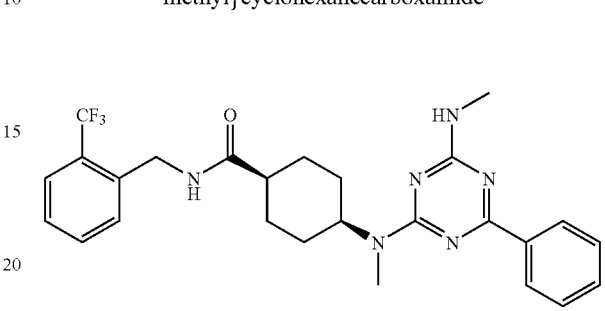

Example 57 was prepared using the general procedure described above in Example 53 substituting Intermediate 16 for trans-4-aminocyclohexanecarboxylic acid in Step 1. MS (ES+): m/e 499.3 [M+H]+.

Example 58 cis-4-{methyl[4-(methylamino)-6-phenyl-1,3,5-triazin-2-yl]amino}-N-({2-[(trifluoromethyl)oxy]phenyl}methyl)cyclohexanecarboxamide

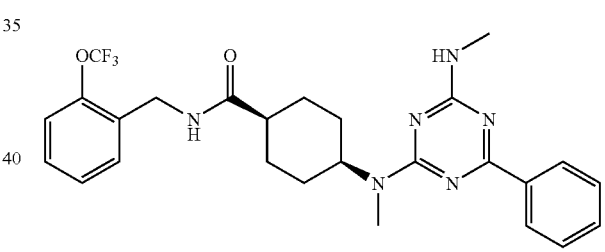

Example 58 was prepared using the general procedure described above in Example 53 substituting Intermediate 16 for trans-4-aminocyclohexanecarboxylic acid in Step 1 and 1-{2-[(trifluoromethyl)oxy]phenyl}methanamine for 1-[2-(trifluoromethyl)phenyl]methanamine in Step 2. MS (ES+): m/e 515.3 [M+H]+.

Example 59 cis-N-[(2,4-dichlorophenyl)methyl]-4-{methyl[4-(methylamino)-6-phenyl-1,3,5-triazin-2-yl]amino}cyclohexanecarboxamide

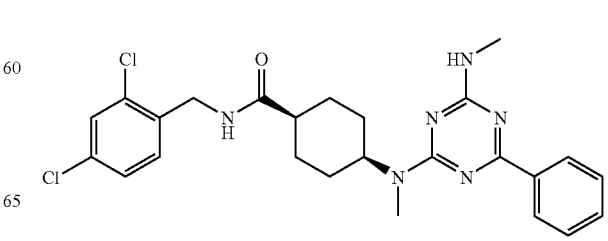

Example 59 was prepared using the general procedure described above in Example 53 substituting Intermediate 16 for trans-4-aminocyclohexanecarboxylic acid in Step 1 and [(2,4-dichlorophenyl)methyl]amine for 1-[2-(trifluoromethyl)phenyl]methanamine in Step 2. MS (ES+): m/e 499.0 [M+H]⁺.

Example 60 cis-N-{[4-chloro-2-(trifluoromethyl)phenyl]methyl}-4-{methyl[4-(methylamino)-6-phenyl-1,3,5-triazin-2-yl]amino}cyclohexanecarboxamide

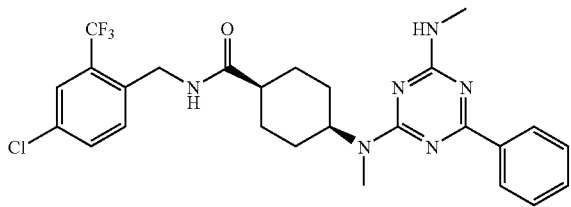

Example 60 was prepared using the general procedure described above in Example 53 substituting Intermediate 16 for trans-4-aminocyclohexanecarboxylic acid in Step 1 and 1-[4-chloro-2-(trifluoromethyl)phenyl]methanamine for 1-[2-(trifluoromethyl)phenyl]methanamine in Step 2. MS (ES+): m/e 533.1 [M+H]⁺.

Example 61

3-{[4-(methylamino)-6-phenyl-1,3,5-triazin-2-yl]amino}-N-{[2-trifluoromethyl)phenyl]methyl}cyclohexanecarboxamide

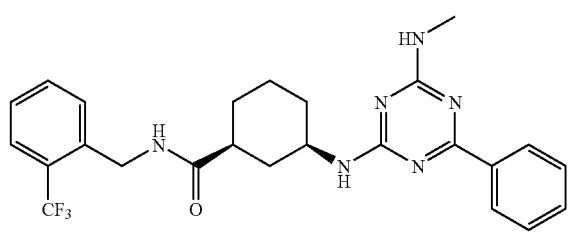

Example 61 was prepared using the general procedure described above in Example 53 substituting 3-aminocyclohexanecarboxylic acid for trans-4-aminocyclohexanecarboxylic acid in Step 1. MS (ES+): m/e 485.3 [M+H]⁺.

Example 62

3-{[4-(methylamino)-6-phenyl-1,3,5-triazin-2-yl]amino}-N-({2-[(trifluoromethyl)oxy]phenyl}methyl)cyclohexanecarboxamide

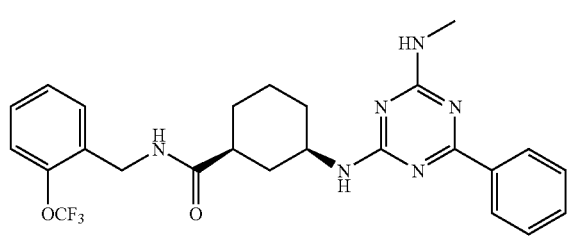

Example 62 was prepared using the general procedure described above in Example 53 substituting 3-aminocyclohexanecarboxylic acid for trans-4-aminocyclohexanecarboxylic acid in Step 1 and 1-{2-[(trifluoromethyl)oxy]phenyl}methanamine for 1-[2-(trifluoromethyl)phenyl]methanamine in Step 2. MS (ES+): m/e 501.1 [M+H]⁺.

Example 63

N-[(2,4-dichlorophenyl)methyl]-3-{[4-(methylamino)-6-phenyl-1,3,5-triazin-2-yl]amino}cyclohexanecarboxamide

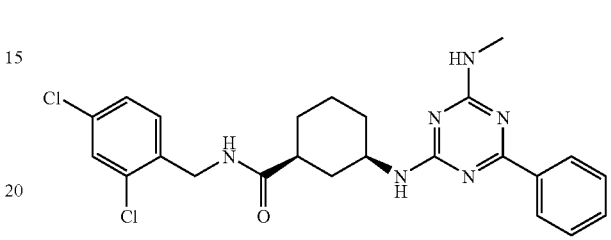

Example 63 was prepared using the general procedure described above in Example 53 substituting 3-aminocyclohexanecarboxylic acid for trans-4-aminocyclohexanecarboxylic acid in Step 1 and [(2,4-dichlorophenyl)methyl]amine for 1-[2-(trifluoromethyl)phenyl]methanamine in Step 2. MS (ES+): m/e 485.2 [M+H]⁺.

Example 64

N-{[4-chloro-2-(trifluoromethyl)phenyl]methyl}-3-{[4-methyl-6-(methylamino)-1,3,5-triazin-2-yl]amino}cyclohexanecarboxamide

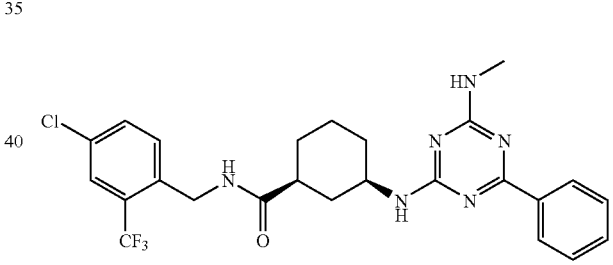

Example 64 was prepared using the general procedure described above in Example 53 substituting 3-aminocyclohexanecarboxylic acid for trans-4-aminocyclohexanecarboxylic acid in Step 1 and 1-[4-chloro-2-(trifluoromethyl)phenyl]methanamine for 1-[2-(trifluoromethyl)phenyl]methanamine in Step 2. MS (ES+): m/e 519.3 [M+H]⁺.

Example 65 cis-N-[(2,4-dichlorophenyl)methyl]-4-{[4-(methylamino)-6-phenyl-1,3,5-triazin-2-yl]amino}cyclohexanecarboxamide

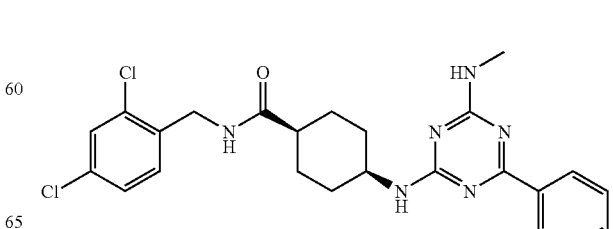

Example 65 was prepared using the general procedure described above in Example 53 substituting cis-4-aminocyclohexanecarboxylic acid for trans-4-aminocyclohexanecarboxylic acid in Step 1 and [(2,4-dichlorophenyl)methyl]amine for 1-[2-(trifluoromethyl)phenyl]methanamine in Step 2. MS (ES+): m/e 485.0 [M+H]$^+$.

Example 66

4-{[({cis-4-[(4-(methylthio)-6-{[(2R)-2-phenylpropyl]amino}-1,3,5-triazin-2-yl)amino]cyclohexyl}carbonyl)amino]methyl}benzoic acid

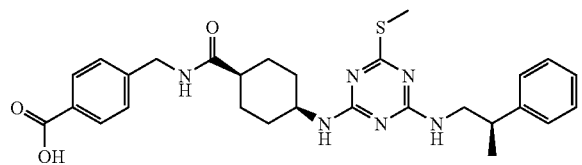

a) Preparation of 4,6-dichloro-N-[(2R)-2-phenylpropyl]-1,3,5-triazin-2-amine

To a suspension of cyanuric chloride (677 mg, 3.67 mmol, 1.00 equiv) in 1:1 CH$_3$CN:H$_2$O (6.1 mL) at 0° C. was added a solution of (2R)-2-phenyl-1-propanamine (0.52 mL, 3.7 mmol, 1.0 equiv) in THF (1.8 mL). The reaction mixture was treated with 1 N NaOH to maintain a pH of 9-10 and stirred for 10 min at 0° C. The resulting suspension was used in the next step without workup or purification. MS (ES+): m/e 282.9 [M+H]$^+$.

b) Preparation of Methyl 4-({[[(cis-4-aminocyclohexyl)carbonyl]amino}methyl)benzoate Using the general procedure described above in step b of Example 1 substituting the appropriate starting materials, the title compound was prepared. MS (ES+): m/e 291.0 [M+H]$^+$.

c) Preparation of methyl 4-{[({cis-4-[(4-chloro-6-{[(2R)-2-phenylpropyl]amino}-1,3,5-triazin-2-yl)amino]cyclohexyl}carbonyl)amino]methyl}benzoate Methyl 4-({[(cis-4-aminocyclohexyl)carbonyl]amino}methyl)benzoate (1.48 g, 3.67 mmol, 1.00 equiv) was added to the suspension prepared in step a. The resulting mixture was heated to 40° C. and treated with 1 N NaOH to maintain a pH of 9-10. The reaction mixture was stirred for 30 min and then used immediately in the next step without workup or purification. MS (ES+): m/e 537.1 [M+H]$^+$.

d) Preparation of 4-{[({cis-4-[(4-(methylthio)-6-{[(2R)-2-phenylpropyl]amino}-1,3,5-triazin-2-yl)amino]cyclohexyl}carbonyl)amino]methyl}benzoic acid To ⅕ of the crude reaction mixture (by volume) prepared in step c, was added NaSMe (51.4 mgs, 7.34 mmol, 10.0 equiv). The resulting mixture was heated to 50° C. for 1 hour. The final solution was purified by reverse-phase HPLC (Sunfire, 25-40% CH$_3$CN, H$_2$O, 0.1% TFA, 12 min) to afford 27.9 mg of the title compound. MS (ES+): m/e 535.2 [M+H]$^+$.

Example 67 cis-N-({4-bromo-2-[(trifluoromethyl)oxy]phenyl}methyl)-3-{[4-methyl-6-(methylamino)-1,3,5-triazin-2-yl]amino}cyclohexanecarboxamide

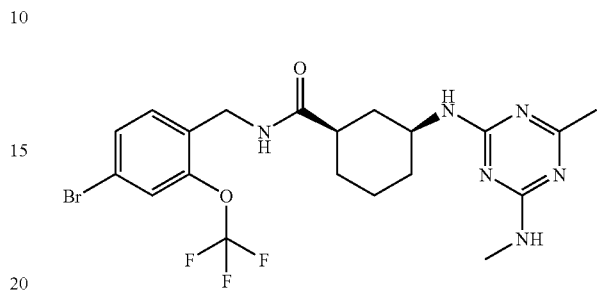

A mixture of ({4-bromo-2-[(trifluoromethyl)oxy]phenyl}methyl)amine (0.4 g, 1.041 mmol), 3-{[4-methyl-6-(methylamino)-1,3,5-triazin-2-yl]amino}cyclohexanecarboxylic acid (0.276 g, 1.041 mmol), 1H-1,2,3-benzotriazol-1-yloxy-tris(dimethylamino)-phosphonium hexafluorophosphate (BOP reagent, 0.507 g, 1.146 mmol) and diisopropylethylamine (0.364 ml, 2.083 mmol) in N,N-Dimethylformamide (DMF) (5 ml) was stirred overnight at RT. The reaction mixture was treated with water which caused a precipitate to form. The precipitate was filtered and washed with water, and dried to give N-({4-bromo-2-[(trifluoromethyl)oxy]phenyl}methyl)-3-{[4-methyl-6-(methylamino)-1,3,5-triazin-2-yl]amino}cyclohexanecarboxamide (0.35 g, 0.543 mmol, 53%) as an off-white solid. MS (ES) m/e 517, 519 [M+H]$^+$.

Example 68 cis-3-{[4-methyl-6-(methylamino)-1,3,5-triazin-2-yl]amino}-N-({4-(4-morpholinyl)-2-[(trifluoromethyl)oxy]phenyl}methyl)cyclohexanecarboxamide

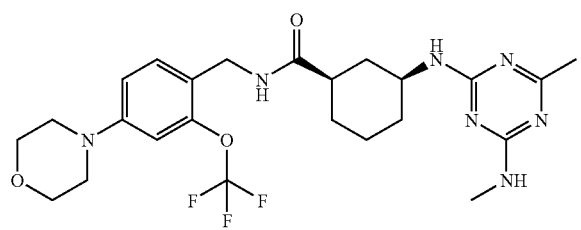

A mixture of N-({4-bromo-2-[(trifluoromethyl)oxy]phenyl}methyl)-3-{[4-methyl-6-(methylamino)-1,3,5-triazin-2-yl]amino}cyclohexanecarboxamide (60 mg, 0.116 mmol), morpholine (20.21 mg, 0.232 mmol), Pd$_2$(dba)$_3$ (5.31 mg, 5.80 μmol), BINAP (5.42 mg, 8.70 μmol) and cesium carbonate (76 mg, 0.232 mmol) in 1,4-Dioxane (2 ml) was irradiated via microwave reactor for 20 min at 170° C. The crude reaction mixture was passed through a 2 gram SCX ion-exchange column. The column was flushed with MeOH, then it was flushed with 2N NH$_3$ in MeOH. The NH$_3$ solution was collected and the solvent was evacuated to give a residue which was purified by preparative HPLC, resulting in 3-{[4- methyl-6-(methylamino)-1,3,5-triazin-2-yl]amino}-N-({4-(4-morpholinyl)-2-[(trifluoromethyl)oxy]phenyl}methyl)cyclohexanecarboxamide (15 mg, 0.022 mmol, 19%). MS (ES) m/e 524 [M+H]+.

Example 69 cis-3-{[4-methyl-6-(methylamino)-1,3,5-triazin-2-yl]amino}-N-({4-(1-piperidinyl)-2-[(trifluoromethyl)oxy]phenyl}methyl)cyclohexanecarboxamide

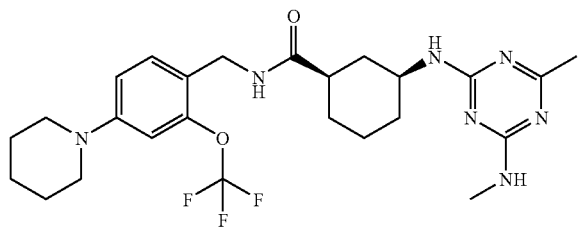

Example 69 was prepared using the general procedure described above in Example 68 substituting piperidine for morpholine. MS (ES+): m/e 522 [M+H]+.

Example 70 cis-3-{[4-methyl-6-(methylamino)-1,3,5-triazin-2-yl]amino}-N-({4-(1-pyrrolidinyl)-2-[(trifluoromethyl)oxy]phenyl}methyl)cyclohexanecarboxamide

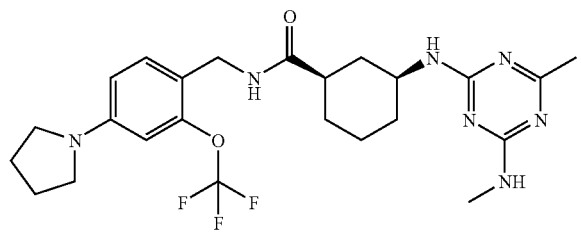

Example 70 was prepared using the general procedure described above in Example 68 substituting pyrrolidine for morpholine. MS (ES+): m/e 508 [M+H]+.

Example 71 cis-N-{[2-chloro-4-(1-piperidinyl)phenyl]methyl}-3-{[4-methyl-6-(methylamino)-1,3,5-triazin-2-yl]amino}cyclohexanecarboxamide

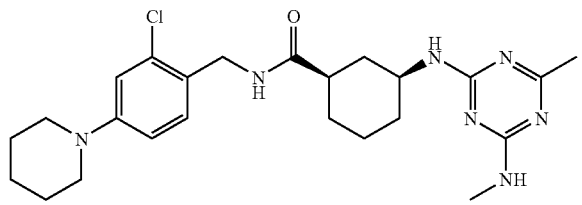

a) 1-(4-bromo-2-chlorophenyl)methanamine

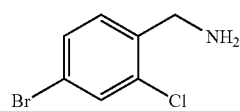

To a solution of 4-bromo-2-chlorobenzonitrile (2 g, 9.24 mmol) in Tetrahydrofuran (THF) (10 ml) was added aluminum hydride (37.0 ml, 18.48 mmol) in THF. The reaction mixture was acidified with 1N HCl to pH=4. The mixture was washed with ether (2×50 ml). The aqueous layer was separated and it was adjusted with 1N NaOH to pH=10. The mixture was extracted with ether. The organic layer was separated and dried over $Na_2SO_4$. The solvent was evacuated to give 1-(4-bromo-2-chlorophenyl)methanamine (1.8 g, 8.2 mmol, 88%). MS (ES+): m/e 220, 222 [M+H]+.

b) N-[(4-bromo-2-chlorophenyl)methyl]-3-{[4-methyl-6-(methylamino)-1,3,5-triazin-2-yl]amino}cyclohexanecarboxamide

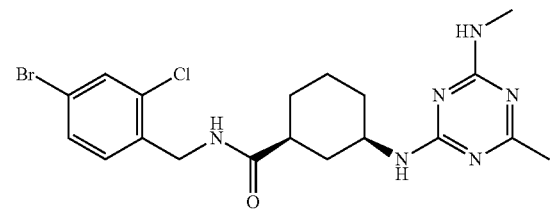

To a solution of 3-{[4-methyl-6-(methylamino)-1,3,5-triazin-2-yl]amino}cyclohexanecarboxylic acid (0.324 g, 0.855 mmol) in N,N-Dimethylformamide (DMF) (25 ml) was added diisopropylethylamine (0.329 ml, 1.881 mmol) followed by 1-(4-bromo-2-chlorophenyl)methanamine (0.286 g, 0.855 mmol) and 1H-1,2,3-benzotriazol-1-yloxy-tris(dimethylamino)-phosphonium hexafluorophosphate (BOP reagent, 0.416 g, 0.940 mmol). The reaction was stirred at room temperature for 3 hours. Saturated $NaHCO_3$ was added to the reaction, at which time white solids precipitated from solution. The solids were filtered, washed with acetonitrile, and dried to provide N-[(4-bromo-2-chlorophenyl)methyl]-3-{[4-methyl-6-(methylamino)-1,3,5-triazin-2-yl]amino}cyclohexanecarboxamide (160 mg, 0.34 mmol, 40%). MS (ES+): m/e 467, 469 [M+H]+.

c) cis-N-{[2-chloro-4-(1-piperidinyl)phenyl]methyl}-3-{[4-methyl-6-(methylamino)-1,3,5-triazin-2-yl]amino}cyclohexanecarboxamide

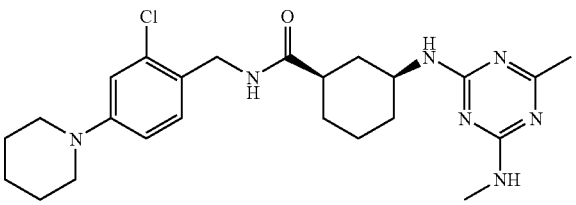

In a microwave reaction vessel was added cesium carbonate (0.049 g, 0.150 mmol) under nitrogen. Next, Pd$_2$(dba)$_3$ (4.89 mg, 5.34 µmol), BINAP (4.99 mg, 8.02 µmol), N-[(4-bromo-2-chlorophenyl)methyl]-3-{[4-methyl-6-(methylamino)-1,3,5-triazin-2-yl]amino}cyclohexanecarboxamide (0.050 g, 0.107 mmol) and piperidine (10.58 µl, 0.107 mmol) were then added to the reaction vial. Toluene (4.00 ml) was added and the reaction was heated to 100° C. for 16 hours. LCMS showed the formation of the desired product and the consumption of the starting materials. The reaction was cooled, the solvent was removed under vacuum, and the residue was purified by preparative HPLC to provide cis-N-{[2-chloro-4-(1-piperidinyl)phenyl]methyl}-3-{[4-methyl-6-(methylamino)-1,3,5-triazin-2-yl]amino}cyclohexanecarboxamide (19 mg, 0.032 mmol, 30%). MS (ES+): m/e 472, 474 [M+H]$^+$.

Example 72

(cis)-3-{[4-methyl-6-(methylamino)-1,3,5-triazin-2-yl]amino}-N-{[4-(methyloxy)-2-(trifluoromethyl)phenyl]methyl}cyclohexanecarboxamide

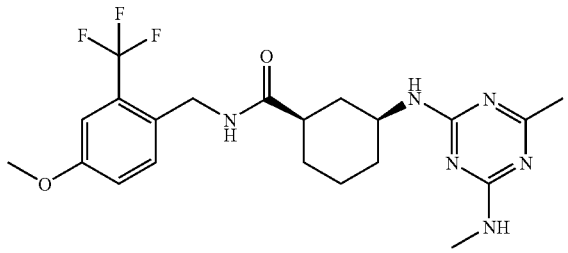

To a solution of 3-{[4-methyl-6-(methylamino)-1,3,5-triazin-2-yl]amino}cyclohexanecarboxylic acid (0.100 g, 0.377 mmol) in N,N-Dimethylformamide (DMF) (5 ml) was added ({[4-(methyloxy)-2-(trifluoromethyl)phenyl]methyl}amine (0.132 g, 0.415 mmol), followed by diisopropylethylamine (0.197 ml, 1.131 mmol) and 1H-1,2,3-benzotriazol-1-yloxy-tris(dimethylamino)-phosphonium hexafluorophosphate (BOP reagent, 0.183 g, 0.415 mmol). The reaction was stirred at room temperature for 4 hours and then purified by preparative HPLC to provide (cis)-3-{[4-methyl-6-(methylamino)-1,3,5-triazin-2-yl]amino}-N-{[4-(methyloxy)-2-(trifluoromethyl)phenyl]methyl}cyclohexanecarboxamide (31 mg, 0.06 mmol, 16%). MS (ES+): m/e 453 [M+H]$^+$.

Example 73

(cis)-N-{[4-fluoro-2-(trifluoromethyl)phenyl]methyl}-3-{[4-methyl-6-(methylamino)-1,3,5-triazin-2-yl]amino}cyclohexanecarboxamide

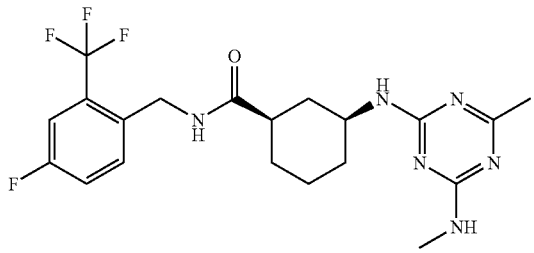

To a solution of 3-{[4-methyl-6-(methylamino)-1,3,5-triazin-2-yl]amino}cyclohexanecarboxylic acid (0.100 g, 0.264 mmol) in N,N-Dimethylformamide (DMF) (4 ml) was added ({[4-fluoro-2-(trifluoromethyl)phenyl]methyl}amine (0.051 g, 0.264 mmol) followed by diisopropylethylamine (0.101 ml, 0.580 mmol) and 1H-1,2,3-benzotriazol-1-yloxy-tris(dimethylamino)-phosphonium hexafluorophosphate (BOP reagent, 0.128 g, 0.290 mmol). The reaction was stirred at room temperature for 4 hours and then purified by preparative HPLC to provide (cis)-N-{[4-fluoro-2-(trifluoromethyl)phenyl]methyl}-3-{[4-methyl-6-(methylamino)-1,3,5-triazin-2-yl]amino}cyclohexanecarboxamide (82 mg, 0.148 mmol, 56%). MS (ES) m/e 441 [M+H]$^+$. $^1$H NMR (400 MHz, DMSO-D6) ☐ 7.6 (bs, 1H), 6.8 (m, 1H), 6.7 (m, 1H), 6.5 (m, 1H), 3.8 (m, 2H), 3.3 (m, 1H), 2.2 (s, 3H), 2.2-2.1 (m, 1H), 1.7-1.6 (bm, 1H), 1.5 (s, 3H), 1.3-1.1 (bm, 4H), 0.8-0.5 (bm, 4H)

Example 74

(cis)-N-{[4-cyano-2-(trifluoromethyl)phenyl]methyl}-3-{[4-methyl-6-(methylamino)-1,3,5-triazin-2-yl]amino}cyclohexanecarboxamide

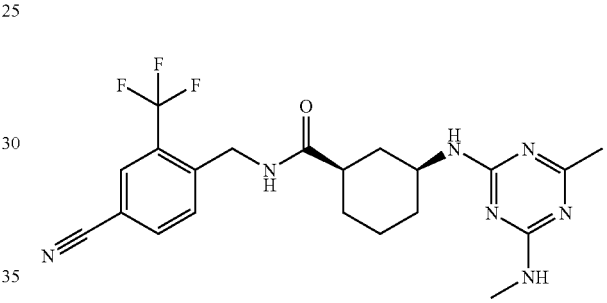

To a solution of 3-{[4-methyl-6-(methylamino)-1,3,5-triazin-2-yl]amino}cyclohexanecarboxylic acid (0.100 g, 0.264 mmol) in N,N-Dimethylformamide (DMF) (4 ml) was added 4-(aminomethyl)-3-(trifluoromethyl)benzonitrile (0.053 g, 0.264 mmol) followed by diisopropylethylamine (0.101 ml, 0.580 mmol) and 1H-1,2,3-benzotriazol-1-yloxy-tris(dimethylamino)-phosphonium hexafluorophosphate (BOP reagent, 0.128 g, 0.290 mmol). The reaction was stirred at room temperature for 4 hours and then purified by preparative HPLC to provide (cis)-N-{[4-cyano-2-(trifluoromethyl)phenyl]methyl}-3-{[4-methyl-6-(methylamino)-1,3,5-triazin-2-yl]amino}cyclohexanecarboxamide (83 mg, 0.148 mmol, 56%). MS (ES) m/e 448 [M+H]$^+$. $^1$H NMR (400 MHz, DMSO-D6) ☐ 7.8 (bs, 1H), 7.3 (bs, 1H), 7.2 (m, 1H), 6.9 (m, 1H), 3.8 (bs, 2H), 3.3 (bm, 1H), 2.2 (bm, 4H), 1.8-1.5 (bm, 4H), 1.3-1.1 (bm, 4H), 0.8-0.5 (bm, 4H)

As used above, the phrase "using the general procedure described above" indicates that the procedure used employs similar, but not necessarily identical, reaction conditions to those referred to.

Biological Activity

The compounds according to Formula I are sEH inhibitors. The compounds according to Formula I, therefore, are useful in the treatment of hypertension and other conditions involving sEH activity. As stated above, mEH provides an important detoxification pathway in mammals. Compounds that exhibit pharmacological selectivity for sEH over mEH therefore are desirable in the methods of treatment described below. Accordingly, in one embodiment the invention is directed to a compound according to Formula I wherein the compound exhibits a selectivity ratio equal to or greater than 10:1 for sEH over mEH. In another embodiment the invention is directed to a compound according to Formula I wherein the compound exhibits a selectivity ratio equal to or greater than 100:1 for sEH over mEH. In another embodiment the invention is directed to a compound according to Formula I wherein the compound exhibits a selectivity ratio equal to or greater than 1000:1 for sEH over mEH.

The biological activity of the compounds according to Formula I can be determined using any suitable assay for determining the activity of a candidate compound as an sEH and/or mEH inhibitor, as well as suitable tissue and/or in vivo models.

In Vitro Fluorescence Assay

Inhibition of Soluble Expoxide Hydrolase (sEH) activity is measured in a fluorescent assay based upon the format described by Wolf et al. (Analytical Biochemistry Vol. 355 (2006) pp. 71-80). In the presence of sEH, PHOME ((3-Phenyl-oxiranyl)-acetic acid cyano-(6-methoxy-naphthalen-2-yl)-methyl ester), is hydrolyzed to a diol which goes through an intramolecular cyclization and the release and decomposition of cyanohydrin (products=cyanide and 6-methoxy-2-naphthaldehyde). Production of 6-methoxy-2-naphthaldehyde is monitored at excitation of 360 nm and an emission of 465 nm.

The assay is used in a quenched assay format by sequentially adding enzyme (5 uL; 200 pM sEH in 25 mM Hepes at pH 7.0, 0.01% CHAPS (w/v), 0.005% Casein (w/v); 10 minute ambient pre-incubation after addition) then PHOME substrate (5 ul; 10 uM PHOME substrate in 25 mM Hepes at pH 7.0, 0.01% CHAPS (w/v), 0.005% Casein (w/v)) to a 384 well assay plate (Greiner 784076) pre-stamped with 25-100 mL compound at the desired concentration. The reaction is incubated for 30 minutes at room temperature, then quenched by the addition of stop solution (5 uL; 10 mM ZnSO4 in 25 mM Hepes at pH 7.0, 0.01% CHAPS (w/v), 0.005% Casein (w/v)). Microtiter plates are centrifuged after each addition for 30 seconds at 500 rpm. The fluorescence is measured on an EnVision plate reader platform (Perkin Elmer) using a 360 nm excitation filter, 465 nm emission filter, and 400 nm dichroic filter.

Compounds are first prepared in neat DMSO at a concentration of 10 mM, then diluted as required to achieve the desired assay concentration. For inhibition curves, compounds are diluted using a three fold serial dilution and tested at 11 concentrations (e.g. 50 µM-0.8 nM or 25 µM-0.42 nM or 2.5 µM to 42 pM). Curves are analysed using ActivityBase and XLfit, and results are expressed as $pIC_{50}$ values.

Cell-Based sEH Inhibitor Assay

Cell based sEH inhibition is measured using the 14, 15-DHET immunoassay ELISA kit available from Detroit R&D (Cat. No. DH1), according to the following procedure:

HEK293 cells (BioCat ID 80556) are transduced by sEH BacMam virus to increase sEH expression (other cell lines may be suitable) as follows: One day before the experiment, 1.5 million HEK293 cells (BioCat ID 80556) are seated in 3 ml of DMEM/F12 (with L-Glutamine, with 15 mM HEPES, pH7.30, from Media Prep Lab), with 10% fetal bovine serum (from SAFC Biosciences, Cat. No. 12176-1000M), no antibiotic, in a 25 cm$^2$ flask (from Corning Incorporated, Cat. No. 430639) and 30 µL sEH BacMam virus is added. The cells are gently mixed then incubated at 37° C., 5% $CO_2$, for 24 hours.

The cells are trypsinized to release them from the growth flask, washed once with PBS, then re-suspended in 5 mL DMEM/F12 without phenol red (from Media Prep lab).

Cell density should be approximately $3*10^5$ cells/mL (=300 cells/µL), counted using the Cedex AS[20] (from Innovatis).

The cells are then diluted in DMEM/F12 to 5.1 cells/µL, and 98 µL/well (=500 cells/well) of this cell suspension is transferred to an assay plate (96 well, clear polystyrene, flat bottom, from Whatman, Cat. No. 7701-1350).

2 µL of the diluted test compound is then added to the cells in the assay plate. The reaction plate is shaken gently and incubated at room temperature for 30 min, after which 10 µL of substrate solution is added (substrate solution is prepared by diluting 1.24 □L of 14, 15-EET from Cayman Chemical, Cat. No. 50651 with 8.24 µL DMEM/F12). The assay plate is then incubated for one hour at room temperature.

After the 1 hour reaction, the reaction mixture is diluted 3 fold with provided sample dilution buffer (ex. Add 220 µL to the 110 µL reaction mixture), mixed well, and spun for 5 min at 500 rpm.

100 µL of the diluted reaction mixture is then transferred from the reaction plates to the ELISA plates, and the ELISA is performed according to the instructions provided in the kit.

IC50s and pIC50s are then calculated. The IC50 can be calculated directly using the 14, 15-DHET concentration or using the % inhibition [% inhibition=100*(1−(sample DHET−0 cell DHET)/(500 cells DHET−0 cell DHET)].

Compounds are first prepared in neat DMSO at a concentration of 0.5 mM, then diluted as required to achieve the desired assay concentration. For inhibition curves, compounds are diluted using a three fold serial dilution and tested at 9 concentrations (e.g. 10 µM-1.5 nM). Curves are analysed using ActivityBase and XLfit, and results are expressed as pIC50 values.

Biological Activity Results

All of the compounds exemplified above were tested for activity as sEH inhibitors. Where the assay for a particular compound had been performed two or more times, the following conclusion regarding their activities is based on the average of individual experiments. All exemplified compounds were found to have an IC50 in the range of 0.1 and 10,000 nM.

Methods of Use

Methods of Use

The compounds of the invention inhibit the sEH enzyme and can be useful in the treatment of conditions wherein the underlying pathology is (at least in part) attributable to sEH involvement or in conditions wherein sEH inhibition offers some clinical benefit even though the underlying pathology is not (even in part) attributable to sEH involvement. Examples of such conditions include hypertension, organ failure/damage (including heart failure, renal failure, and liver failure), cardiac and renal fibrosis, peripheral vascular disease (including ischemic limb disease, intermittent claudication, endothelial dysfunction, erectile dysfunction, Raynaud's disease, and diabetic vasculopathies e.g. retinopathy), atherothrombotic disorders (including coronary artery disease, coronary vasospasm, angina, stroke, myocardial ischemia, myocardial infarction, and hyperlipidemia), metabolic disorders (including diabetes), and inflammatory disorders (including arthritis, inflammatory pain, overactive bladder, asthma, and COPD). Accordingly, in another aspect the invention is directed to methods of treating such conditions.

Essential hypertension is commonly associated with the development of significant end organ damage such as renal, endothelial, myocardial, and erectile dysfunction. Such conditions occur "secondary" to the elevated systemic arterial blood pressure. Secondary conditions may be prevented by treatment of the underlying ("primary") cause. Accordingly, in another aspect the invention is directed to methods of preventing such secondary conditions.

Heart failure is a complex heterogenous disorder characterized by reduced cardiac output, resulting in the inability of the heart to meet perfusion demands of the body. Cardiac proinflammatory cytokine recruitment and maladaptive cardiac hypertrophy, fibrosis and apoptosis/necrosis are factors associated with the progression of heart failure. Compounds of the invention are directed to methods of treating such conditions.

In addition, sEH is indirectly involved in the regulation of platelet function through its effect on EETs. Drugs that inhibit platelet aggregation are believed to decrease the risk of atherthrombotic events, such as myocardial infarction and stroke, in patients with established cardiovascular atherosclerotic disease. Accordingly, in another aspect the invention is directed to methods of preventing atherothrombotic events, such as myocardial infarction and stroke in patients with a history of recent myocardial infarction, stroke, transient ischemic attacks, unstable angina, or atherosclerosis.

The methods of treating and the methods of preventing described above comprise administering a safe and effective amount of a compound of the invention to a patient in need thereof.

As used herein, "treatment" in reference to a condition means: (1) the amelioration or prevention of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to significantly induce a positive modification in the condition to be treated but low enough to avoid serious side effects (at a reasonable benefit/risk ratio) within the scope of sound medical judgment. A safe and effective amount of a compound of the invention will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, but can nevertheless be determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the amount administered and the duration such regimens are administered, for a compound of the invention depend on the condition being treated, the severity of the condition being treated, the age and physical condition of the patient being treated, the medical history of the patient to be treated, the nature of concurrent therapy, the particular route of administration chosen, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Typical daily dosages range from 1 mg to 1000 mg.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein a safe and effective amount of a compound of the invention can be extracted and then given to the patient such as with powders, syrups, and solutions for injection. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds. Conversely, the pharmaceutical compositions of the invention typically contain more than one pharmaceutically-acceptable excipient. However, in certain embodiments, the pharmaceutical compositions of the invention contain one pharmaceutically-acceptable excipient.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when comingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excepient or excepients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

What is claimed is:

1. A compound or salt of Formula I

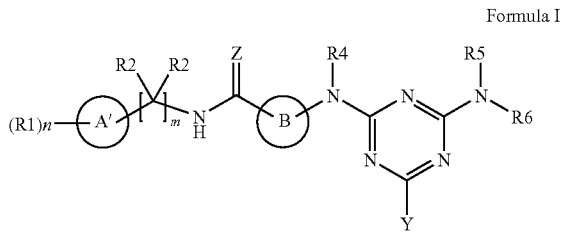

Formula I wherein:
A is phenyl, thiophenyl, or pyridyl;
R1 is $CF_3$, halo, $OCF_3$, CN, $OC_1$-$C_6$ alkyl, morpholino, $CO_2H$, or $N(CH_3)_2$;
R2 is H;
m is 1 or 2;
n is 1, 2, or 3;
B is cyclohexyl;
R4 is hydrogen;
Z is O;

Y is C1-C3 alkyl, phenyl, thiophenyl, or pyridyl; wherein the phenyl, thiophenyl or pyridyl may be substituted by —CO$_2$H, SO$_2$Me, CF$_3$, halo, or CN;
R5 is hydrogen or C1-C6 alkyl; and
R6 is hydrogen or C1-C6 alkyl.

2. A compound or salt of Formula I

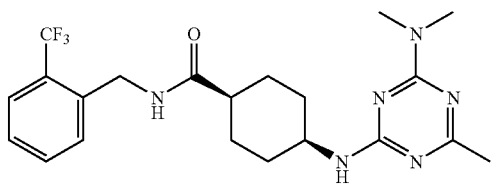

wherein:
A is phenyl;
R1 is CF$_3$, halo, OCF$_3$, CN, OC$_1$-C$_6$ alkyl, or morpholino;
R2 is H;
m is 1 or 2;
n is 1, or 2;
B is cyclohexyl;
R4 is hydrogen;
Z is O;
Y is methyl;
R5 is hydrogen; and
R6 is methyl.

3. A compound chosen from:
cis-4-{[4-(methylamino)-6-(3-pyridinyl)-1,3,5-triazin-2-yl]amino}-N-{[2-(trifluoromethyl)phenyl]methyl}cyclohexanecarboxamide;
cis-4-{[4-(methylamino)-6-phenyl-1,3,5-triazin-2-yl]amino}-N-{[2-(trifluoromethyl)phenyl]methyl}cyclohexanecarboxamide;
cis-4-{[4-(methylamino)-6-(3-thienyl)-1,3,5-triazin-2-yl]amino}-N-{[2-(trifluoromethyl)phenyl]methyl}cyclohexanecarboxamide;
cis-4-{[4-[4-(1,1-dimethylethyl)phenyl]-6-(methylamino)-1,3,5-triazin-2-yl]amino}-N-{[2-(trifluoromethyl)phenyl]methyl}cyclohexanecarboxamide;
cis-4-{[4-(2-fluorophenyl)-6-(methylamino)-1,3,5-triazin-2-yl]amino}-N-{[2-(trifluoromethyl)phenyl]methyl}cyclohexanecarboxamide;
cis-4-{[4-(4-cyanophenyl)-6-(methylamino)-1,3,5-triazin-2-yl]amino}-N-{[2-(trifluoromethyl)phenyl]methyl}cyclohexanecarboxamide;
cis-4-({4-(methylamino)-6-[4-(methylsulfonyl)phenyl]-1,3,5-triazin-2-yl}amino)-N-({2-[(trifluoromethyl)oxy]phenyl}methyl)cyclohexan;
cis-4-{[4-(methylamino)-6-(3-pyridinyl)-1,3,5-triazin-2-yl]amino}-N-({2-[(trifluoromethyl)oxy]phenyl}methyl)cyclohexanecarboxamide;
cis-4-({4-(methylamino)-6-[4-(trifluoromethyl)phenyl]-1,3,5-triazin-2-yl}amino)-N-({2-[(trifluoromethyl)oxy]phenyl}methyl)cyclohexanecarboxamide;
3-{4-(methylamino)-6-[(cis-4-{[({2-[(trifluoromethyl)oxy]phenyl}methyl)amino]carbonyl}cyclohexyl)amino]-1,3,5-triazin-2-yl}benzoic acid;
3-[4-(methylamino)-6-({cis-4-[({[4-(methyloxy)-2-(trifluoromethyl)phenyl]methyl}amino)carbonyl]cyclohexyl}amino)-1,3,5-triazin-2-yl]benzoic acid;
cis-4-({4-(methylamino)-6-[4-(trifluoromethyl)phenyl]-1,3,5-triazin-2-yl}amino)-N-{[4-(methyloxy)-2-(trifluoromethyl)phenyl]methyl}cyclohexanecarboxamide;
cis-4-{[4-(methylamino)-6-(3-pyridinyl)-1,3,5-triazin-2-yl]amino}-N-{[4-(methyloxy)-2-(trifluoromethyl)phenyl]methyl}cyclohexanecarboxamide;
cis-4-({4-(methylamino)-6-[4-(methylsulfonyl)phenyl]-1,3,5-triazin-2-yl}amino)-N-{[4-(methyloxy)-2-(trifluoromethyl)phenyl]methyl}cyclohexanecarboxamide;
3-[4-(methylamino)-6-({cis-4-[({[4-(trifluoromethyl)-3-pyridinyl]methyl}amino)carbonyl]cyclohexyl}amino)-1,3,5-triazin-2-yl]benzoic acid;
cis-4-({4-(methylamino)-6-[4-(trifluoromethyl)phenyl]-1,3,5-triazin-2-yl}amino)-N-{[4-(trifluoromethyl)-3-pyridinyl]methyl}cyclohexanecarboxamide;
cis-4-{[4-(methylamino)-6-(3-pyridinyl)-1,3,5-triazin-2-yl]amino}-N-{[4-(trifluoromethyl)-3-pyridinyl]methyl}cyclohexanecarboxamide;
cis-4-({4-(methylamino)-6-[4-(methylsulfonyl)phenyl]-1,3,5-triazin-2-yl}amino)-N-{[4-(trifluoromethyl)-3-pyridinyl]methyl}cyclohexanecarboxamide;
3-[4-{[cis-4-({[(2-chloro-4-cyanophenyl)methyl]amino}carbonyl)cyclohexyl]amino}-6-(methylamino)-1,3,5-triazin-2-yl]benzoic acid;
cis-N-[(2-chloro-4-cyanophenyl)methyl]-4-{[4-(methylamino)-6-(3-pyridinyl)-1,3,5-triazin-2-yl]amino}cyclohexanecarboxamide;
cis-4-({4-[(2-hydroxyethyl)amino]-6-methyl-1,3,5-triazin-2-yl}amino)-N-{[2-(trifluoromethyl)phenyl]methyl}cyclohexanecarboxamide;
cis-4-{[4-methyl-6-(4-methyl-1-piperazinyl)-1,3,5-triazin-2-yl]amino}-N-{[2-(trifluoromethyl)phenyl]methyl}cyclohexanecarboxamide;
cis-4-({4-methyl-6-[(phenylmethyl)amino]-1,3,5-triazin-2-yl}amino)-N-{[2-(trifluoromethyl)phenyl]methyl}cyclohexanecarboxamide;
cis-4-[(4-methyl-6-{[2-(methyloxy)ethyl]amino}-1,3,5-triazin-2-yl)amino]-N-{[2-(trifluoromethyl)phenyl]methyl}cyclohexanecarboxamide;
cis-4-{[4-(dimethylamino)-6-methyl-1,3,5-triazin-2-yl]amino}-N-{[2-(trifluoromethyl)phenyl]methyl}cyclohexanecarboxamide;
cis-4-{[4-methyl-6-(1-piperidinyl)-1,3,5-triazin-2-yl]amino}-N-{[2-(trifluoromethyl)phenyl]methyl}cyclohexanecarboxamide;
cis-4-[(4-amino-6-methyl-1,3,5-triazin-2-yl)amino]-N-{[2-(trifluoromethyl)phenyl]methyl}cyclohexanecarboxamide;
N-[(2,4-dichlorophenyl)methyl]-3-{[4-methyl-6-(methylamino)-1,3,5-triazin-2-yl]amino}cyclohexanecarboxamide;
cis-3-{[4-methyl-6-(methylamino)-1,3,5-triazin-2-yl]amino}-N-{[2-(trifluoromethyl)phenyl]methyl}cyclohexanecarboxamide;
cis-3-{[4-methyl-6-(methylamino)-1,3,5-triazin-2-yl]amino}-N-({2-[(trifluoromethyl)oxy]phenyl}methyl)cyclohexanecarboxamide;
cis-N-{[4-chloro-2-(trifluoromethyl)phenyl]methyl}-3-{[4-methyl-6-(methylamino)-1,3,5-triazin-2-yl]amino}cyclohexanecarboxamide;
(cis)-N-({2-chloro-4-[(methylsulfonyl)amino]phenyl}methyl)-3-{[4-methyl-6-(methylamino)-1,3,5-triazin-2-yl]amino}cyclohexanecarboxamide;
(cis)-N-{[2-chloro-4-(dimethylamino)phenyl]methyl}-3-{[4-methyl-6-(methylamino)-1,3,5-triazin-2-yl]amino}cyclohexanecarboxamide;
(cis)-N-[(2-chloro-4-cyanophenyl)methyl]-3-{[4-methyl-6-(methylamino)-1,3,5-triazin-2-yl]amino}cyclohexanecarboxamide;

(cis)-N-{[2-chloro-4-(1H-tetrazol-5-yl)phenyl]methyl}-3-{[4-methyl-6-(methylamino)-1,3,5-triazin-2-yl]amino}cyclohexanecarboxamide;
(cis)-3-{[4-methyl-6-(methylamino)-1,3,5-triazin-2-yl]amino}-N-{[3-(trifluoromethyl)-4-pyridinyl]methyl}cyclohexanecarboxamide;
(cis)-3-{[4-(2-fluorophenyl)-6-(methylamino)-1,3,5-triazin-2-yl]amino}-N-{[2-(trifluoromethyl)phenyl]methyl}cyclohexanecarboxamide;
(cis)-3-{[4-(4-fluorophenyl)-6-(methylamino)-1,3,5-triazin-2-yl]amino}-N-{[2-(trifluoromethyl)phenyl]methyl}cyclohexanecarboxamide;
(cis)-3-{[4-(4-cyanophenyl)-6-(methylamino)-1,3,5-triazin-2-yl]amino}-N-{[2-(trifluoromethyl)phenyl]methyl}cyclohexanecarboxamide;
(cis)-4-{[4-methyl-6-(methylamino)-1,3,5-triazin-2-yl]amino}-N-{[2-(trifluoromethyl)phenyl]methyl}cyclohexanecarboxamide;
cis-4-{[4-methyl-6-(methylamino)-1,3,5-triazin-2-yl]amino}-N-({2-[(trifluoromethyl)oxy]phenyl}methyl)cyclohexanecarboxamide;
cis-N-[(2,4-dichlorophenyl)methyl]-4-{[4-methyl-6-(methylamino)-1,3,5-triazin-2-yl]amino}cyclohexanecarboxamide cis-N-{[4-chloro-2-(trifluoromethyl)phenyl]methyl}-4-{[4-methyl-6-(methylamino)-1,3,5-triazin-2-yl]amino}cyclohexanecarboxamide;
cis-4-{[4-methyl-6-(methylamino)-1,3,5-triazin-2-yl]amino}-N-({2-[(trifluoromethyl)thio]phenyl}methyl)cyclohexanecarboxamide;
trans-4-{[4-methyl-6-(methylamino)-1,3,5-triazin-2-yl]amino}-N-{[2-(trifluoromethyl)phenyl]methyl}cyclohexanecarboxamide;
trans-4-{[4-methyl-6-(methylamino)-1,3,5-triazin-2-yl]amino}-N-({2-[(trifluoromethyl)oxy]phenyl}methyl)cyclohexanecarboxamide;
cis-4-{methyl[4-methyl-6-(methylamino)-1,3,5-triazin-2-yl]amino}-N-{[2-(trifluoromethyl)phenyl]methyl}cyclohexanecarboxamide;
cis-4-{methyl[4-methyl-6-(methylamino)-1,3,5-triazin-2-yl]amino}-N-({2-[(trifluoromethyl)oxy]phenyl}methyl)cyclohexanecarboxamide;
cis-N-[(2,4-dichlorophenyl)methyl]-4-{methyl[4-methyl-6-(methylamino)-1,3,5-triazin-2-yl]amino}cyclohexanecarboxamide;
cis-N-{[4-chloro-2-(trifluoromethyl)phenyl]methyl}-4-{methyl[4-methyl-6-(methylamino)-1,3,5-triazin-2-yl]amino}cyclohexanecarboxamide;
trans-4-{[4-(methylamino)-6-phenyl-1,3,5-triazin-2-yl]amino}-N-{[2-(trifluoromethyl)phenyl]methyl}cyclohexanecarboxamide;
trans-4-{[4-(methylamino)-6-phenyl-1,3,5-triazin-2-yl]amino}-N-({2-[(trifluoromethyl)oxy]phenyl}methyl)cyclohexanecarboxamide
trans-N-[(2,4-dichlorophenyl)methyl]-4-{[4-(methylamino)-6-phenyl-1,3,5-triazin-2-yl]amino}cyclohexanecarboxamide;
trans-N-{[4-chloro-2-(trifluoromethyl)phenyl]methyl}-4-{[4-(methylamino)-6-phenyl-1,3,5-triazin-2-yl]amino}cyclohexanecarboxamide;
cis-4-{methyl[4-(methylamino)-6-phenyl-1,3,5-triazin-2-yl]amino}-N-{[2-(trifluoromethyl)phenyl]methyl}cyclohexanecarboxamide;
cis-4-{methyl[4-(methylamino)-6-phenyl-1,3,5-triazin-2-yl]amino}-N-({2-[(trifluoromethyl)oxy]phenyl}methyl)cyclohexanecarboxamide;
cis-N-[(2,4-dichlorophenyl)methyl]-4-{methyl[4-(methylamino)-6-phenyl-1,3,5-triazin-2-yl]amino}cyclohexanecarboxamide;
cis-N-{[4-chloro-2-(trifluoromethyl)phenyl]methyl}-4-{methyl[4-(methylamino)-6-phenyl-1,3,5-triazin-2-yl]amino}cyclohexanecarboxamide;
3-{[4-(methylamino)-6-phenyl-1,3,5-triazin-2-yl]amino}-N-{[2-(trifluoromethyl)phenyl]methyl}cyclohexanecarboxamide;
3-{[4-(methylamino)-6-phenyl-1,3,5-triazin-2-yl]amino}-N-({2-[(trifluoromethyl)oxy]phenyl}methyl)cyclohexanecarboxamide;
N-[(2,4-dichlorophenyl)methyl]-3-{[4-(methylamino)-6-phenyl-1,3,5-triazin-2-yl]amino}cyclohexanecarboxamide;
N-{[4-chloro-2-(trifluoromethyl)phenyl]methyl}-3-{[4-methyl-6-(methylamino)-1,3,5-triazin-2-yl]amino}cyclohexanecarboxamide;
cis-N-[(2,4-dichlorophenyl)methyl]-4-{[4-(methylamino)-6-phenyl-1,3,5-triazin-2-yl]amino}cyclohexanecarboxamide;
4-{[({cis-4-[(4-(methylthio)-6-{[(2R)-2-phenylpropyl]amino}-1,3,5-triazin-2-yl)amino]cyclohexyl}carbonyl)amino]methyl}benzoic acid;
cis-N-({4-bromo-2-[(trifluoromethyl)oxy]phenyl}methyl)-3-{[4-methyl-6-(methylamino)-1,3,5-triazin-2-yl]amino}cyclohexanecarboxamide;
cis-3-{[4-methyl-6-(methylamino)-1,3,5-triazin-2-yl]amino}-N-({4-(4-morpholinyl)-2-[(trifluoromethyl)oxy]phenyl}methyl)cyclohexanecarboxamide;
cis-3-{[4-methyl-6-(methylamino)-1,3,5-triazin-2-yl]amino}-N-({4-(1-piperidinyl)-2-[(trifluoromethyl)oxy]phenyl}methyl)cyclohexanecarboxamide;
cis-3-{[4-methyl-6-(methylamino)-1,3,5-triazin-2-yl]amino}-N-({4-(1-pyrrolidinyl)-2-[(trifluoromethyl)oxy]phenyl}methyl)cyclohexanecarboxamide;
cis-N-{[2-chloro-4-(1-piperidinyl)phenyl]methyl}-3-{[4-methyl-6-(methylamino)-1,3,5-triazin-2-yl]amino}cyclohexanecarboxamide;
(cis)-3-{[4-methyl-6-(methylamino)-1,3,5-triazin-2-yl]amino}-N-{[4-(methyloxy)-2-(trifluoromethyl)phenyl]methyl}cyclohexanecarboxamide;
(cis)-N-{[4-fluoro-2-(trifluoromethyl)phenyl]methyl}-3-{[4-methyl-6-(methylamino)-1,3,5-triazin-2-yl]amino}cyclohexanecarboxamide; and
(cis)-N-{[4-cyano-2-(trifluoromethyl)phenyl]methyl}-3-{[4-methyl-6-(methylamino)-1,3,5-triazin-2-yl]amino}cyclohexanecarboxamide;
or a pharmaceutically acceptable salt thereof.

4. A pharmaceutical composition comprising a compound or salt according to claim 2 and one or more pharmaceutically-acceptable excipient.

5. A method for treating hypertension, heart failure, peripheral vascular disease, coronary artery disease, myocardial ischemia, and angina comprising administering a safe and effective amount of a compound or salt according to claim 2 to a human in need thereof.

6. A method for treating renal or liver failure comprising administering a safe and effective amount of a compound or salt according to claim 2 to a human in need thereof.

7. A method for treating COPD and asthma comprising administering a safe and effective amount of a compound or salt according to claim 2 to a human in need thereof.

8. A method for treating glucose intolerance, insulin insensitivity, diabetes and obesity comprising administering a safe and effective amount of a compound or salt according to claim 2 to a human in need thereof.

9. A method according to claim 5 wherein the compound is administered orally.

10. A method according to claim 5 wherein the compound is administered intravenously.

11. A method according to claim 5 wherein the compound is administered by inhalation.

12. A method according to claim 7 wherein the compound is administered orally.

13. A method according to claim 7 wherein the compound is administered intravenously.

14. A method according to claim 7 wherein the compound is administered by inhalation.

15. A pharmaceutical composition comprising a compound or salt according to claim 3 and one or more pharmaceutically-acceptable excipient.

16. A method for treating COPD and asthma comprising administering a safe and effective amount of a compound or salt according to claim 3 to a human in need thereof.

* * * * *